United States Patent
Parinder et al.

(10) Patent No.: US 11,866,475 B2
(45) Date of Patent: Jan. 9, 2024

(54) MODIFIED RNA ENCODING VEGF-A POLYPEPTIDES, FORMULATIONS, AND USES RELATING THERETO

(71) Applicant: MODERNATX, INC, Cambridge, MA (US)

(72) Inventors: Leif Karlsson Parinder, Mölndal (SE); Regina Desirée Fritsche Danielson, Mölndal (SE); Kenny Mikael Hansson, Mölndal (SE); Li Ming Gan, Mölndal (SE); Jonathan Clarke, Stockholm (SE); Ann-Charlotte Eva Egnell, Mölndal (SE); Kenneth Randall Chien, Stockholm (SE)

(73) Assignee: ModernaTX, Inc., Cambridge, MA (US)

( * ) Notice: Subject to any disclaimer, the term of this patent is extended or adjusted under 35 U.S.C. 154(b) by 760 days.

(21) Appl. No.: 16/305,224

(22) PCT Filed: Jun. 6, 2017

(86) PCT No.: PCT/US2017/036188
§ 371 (c)(1),
(2) Date: Nov. 28, 2018

(87) PCT Pub. No.: WO2017/214175
PCT Pub. Date: Dec. 14, 2017

(65) Prior Publication Data
US 2020/0407411 A1 Dec. 31, 2020

Related U.S. Application Data

(60) Provisional application No. 62/432,005, filed on Dec. 9, 2016, provisional application No. 62/411,091, filed on Oct. 21, 2016, provisional application No. 62/346,979, filed on Jun. 7, 2016.

(51) Int. Cl.
| | | |
|---|---|---|
| *C07K 14/515* | (2006.01) | |
| *A61K 38/18* | (2006.01) | |
| *A61K 31/712* | (2006.01) | |
| *A61P 9/10* | (2006.01) | |
| *A61P 17/02* | (2006.01) | |
| *A61P 13/12* | (2006.01) | |
| *A61P 9/04* | (2006.01) | |
| *A61K 9/00* | (2006.01) | |
| *A61K 47/12* | (2006.01) | |

(52) U.S. Cl.
CPC .......... *C07K 14/515* (2013.01); *A61K 9/0019* (2013.01); *A61K 9/0021* (2013.01); *A61K 31/712* (2013.01); *A61K 38/1866* (2013.01); *A61K 47/12* (2013.01); *A61P 9/10* (2018.01); *A61P 17/02* (2018.01)

(58) Field of Classification Search
CPC ............. C07K 14/515; A61K 38/1866; A61K 31/712; A61K 47/12
See application file for complete search history.

(56) References Cited

U.S. PATENT DOCUMENTS

| | | |
|---|---|---|
| 9,034,316 B2 | 5/2015 | Pecora et al. |
| 9,867,888 B2 | 1/2018 | Benenato |
| 9,868,691 B2 | 1/2018 | Benenato |
| 9,868,692 B2 | 1/2018 | Benenato |
| 9,868,693 B2 | 1/2018 | Benenato |
| 10,266,485 B2 | 4/2019 | Benenato |
| 10,442,756 B2 | 10/2019 | Benenato et al. |
| 2008/0171711 A1 | 7/2008 | Hoerr et al. |
| 2013/0156849 A1 | 6/2013 | de Fougerolles et al. |
| 2013/0259923 A1* | 10/2013 | Bancel ............... A61K 48/0066 424/450 |
| 2014/0073687 A1 | 3/2014 | Chien et al. |
| 2014/0275229 A1* | 9/2014 | Bancel ................ C12N 9/1051 435/193 |
| 2015/0246139 A1 | 9/2015 | Bancel et al. |
| 2016/0046685 A1 | 2/2016 | Nolta et al. |
| 2018/0002393 A1 | 1/2018 | Bancel et al. |
| 2020/0338004 A1 | 10/2020 | Hansson et al. |
| 2022/0226438 A1 | 7/2022 | Hansson et al. |

FOREIGN PATENT DOCUMENTS

| | | |
|---|---|---|
| CN | 102341498 A | 2/2012 |
| CN | 105451779 A | 3/2016 |
| JP | 2014-511694 | 5/2014 |
| KR | 10-1379364 | 3/2014 |
| RU | 2550959 | 5/2015 |
| WO | WO 2010/065671 A2 | 6/2010 |
| WO | WO 2011/069529 A1 | 6/2011 |
| WO | WO 2012/103985 | 8/2012 |
| WO | WO 2012/138453 | 10/2012 |
| WO | WO 2014/152211 A1 | 9/2014 |

(Continued)

OTHER PUBLICATIONS

Sultana et al (2017. Molecular Therapy. 25(6): 1306-1315).*
International search report for PCT/US2017/036188, issued by the Patent Cooperation Treaty, dated Nov. 23, 2017.
Lisa et al., "Double-stranded ribonucleic acid from carnation cryptic virus," Virology, Dec. 1, 1981, 115(2):410-13.
Probst et al., "Spontaneous cellular uptake of exogenous messenger RNA in vivo is nucleic acid-specific, saturable and ion dependent," Gene Therapy, May 3, 2007, 14(15):1175-80.
Zytkovicz et al., "Factors influencing the covalent binding of (±) 7-β,8-α-dihydroxy-9-α,10-α-epoxy-7,8,9,10-tetrahydrobenzo[a]pyrene to RNA," Molecular Pharmacology, Sep. 1984, 26(2):369-75.

(Continued)

*Primary Examiner* — Zachary C Howard
(74) *Attorney, Agent, or Firm* — Fish & Richardson P.C.

(57) ABSTRACT

The disclosure relates to modified RNA molecules encoding VEGF-A polypeptides and formulations comprising the modified RNA. Aspects of the disclosure further relate to preparations and uses of formulations comprising the modified RNA in treating subjects suffering from diseases responsive to VEGF-A therapy.

26 Claims, 53 Drawing Sheets

Figure 3A:
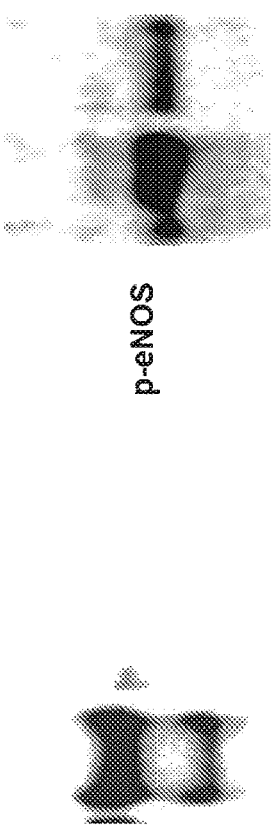

Specification includes a Sequence Listing.

(56) References Cited

FOREIGN PATENT DOCUMENTS

| WO | WO 2015/024667 A1 | 2/2015 |
| WO | WO 2015/107026 A1 | 7/2015 |
| WO | WO 2016/118725 | 7/2016 |
| WO | WO 2017/049245 | 3/2017 |
| WO | WO 2017/214175 | 12/2017 |
| WO | WO 2018/104540 | 6/2018 |
| WO | WO 2018/104874 | 6/2018 |
| WO | WO 2019/089818 | 5/2019 |

OTHER PUBLICATIONS

Carlsson, Leif, et al., "Biocompatible, Purified VEGF-A mRNA Improves Cardiac Function after Intracardiac Injection One Week Post-Myocardial Infarction in Swine," Apr. 2018, DOI: 10.1016/j.omtm.2018.04.003. (17 pages).

Chinese Office Action issued by the Chinese Patent Office in related Application No. CN 201780048447.8, dated Nov. 1, 2021. (26 pages).

Extended European search report pursuant to Rule 62, EPC, the European search report (R. 61 EPC) or the partial European search report/declaration of no search (R. 63 EPC) and the European search Opinion, issued in related International Application No. 21186195.0. (16 pages).

NCBI Predicted—Gorilla gorilla gorilla vascular endothelial growth factor A, transcript variant 1(VEGFA), mRNA-RefSeq ID, XM_004044088.1. (2 pages).

Sun, N., Ning, B., Hansson, K.M. et al., "Modified VEGF-A mRNA induces sustained multifaceted microvascular response and accelerates diabetic wound healing." *Sci Rep 8*, 17509 (2018). https://doi.org/10.1038/s41598-018-35570-6. (11 pages).

Adachi et al., "Determinants of Left Ventricular Systolic Function Improvement Following Coronary Artery Revascularization in Heart Failure Patients With Reduced Ejection Fraction (HFrEF)," Int. Heart J., Sep. 2016, 57(5):565-72.

International Preliminary Report on Patentability in International Application No. PCT/US2020/032241, dated Nov. 2, 2021, 10 pages.

International Preliminary Report on Patentability issued in International Application No. PCT/US2020/032126, dated Nov. 22, 2021, 12 pages.

International Search Report in International Application No. PCT/US2020/032126, dated Sep. 14, 2020, 8 pages.

Järveläinen et al., "Citrate-Saline-Formulated mRNA Delivery into the Heart Muscle with an Electromechanical Mapping and Injection Catheter Does Not Lead to Therapeutic Effects in a Porcine Chronic Myocardial Ischemia Model," Human Gene Therapy, Oct. 2021, 32(19-20), 1295-1307.

Minutti et al., "A Macrophage-Pericyte Axis Directs Tissue Restoration via Amphiregulin-Induced Transforming Growth Factor Beta Activation," Immunity, Mar. 2019, 50(3):645-654.

Mitrut et al., "Histopathological Aspects of the Myocardium in Dilated Cardiomyopathy,"Curr Health Sci J., 2018, 44(3):243-249.

Non-final Office Action issued in U.S. Appl. No. 16/760,406, dated Feb. 16, 2022, 35 pages.

Seferović et al., "Heart failure in cardiomyopathies: a position paper from the Heart Failure Association of the European Society of Cardiology," European Journal of Heart Failure, May 2019, 21(5):553-576.

Third Party Observation issued in International Application No. PCT/US2020/032126, dated May 22, 2021, 2 pages.

U.S. Patent and Trademark Office, *Bayer Cropscience LP v. Syngenta Limited*. Case IPR2017-01332, Apr. 2, 2018, pp. 1-7, (Year: 2018).

Weintraub et al., "Dilated cardiomyopathy," The Lancet, Jul. 2017, 390(10092):400-414.

Written Opinion of the International Searching Authority issued in International Application No. PCT/US2017/036188, dated Nov. 23, 2017, 12 pages.

Written Opinion of the International Searching Authority issued in International Application No. PCT/US2020/032126, dated Sep. 14, 2020, 11 pages.

Anttila et al., "Synthetic mRNA Encoding VEGF-A in Patients Undergoing Coronary Artery Bypass Grafting: Design of a Phase 2a Clinical Trial," Molecular Therapy Methods & Clinical Development, Sep. 2020, 18:464-472.

Businesswire [online], "AstraZeneca and Moderna Announce Filing of First Clinical Trial Application in Messenger RNA Therapeutics Collaboration," Jul. 26, 2016, retrieved on Nov. 8, 2021, retrieved from URL<https://www.businesswire.com/news/home/20160726005317/en/AstraZeneca-Moderna-Announce-Filing-Clinical-Trial-Application>, 2 pages.

Chein et al., "Synthetic Chemically Modified mRNA (modRNA): Toward a New Technology Platform for Cardiovascular Biology and Medicine," Cold Spring Har. Perspect. Med., Oct. 2014, 5(1):1-9.

Coelho et al., "Safety and Efficacy of RNAi Therapy for Transthyretin Amyloidosis," N. Eng. J. Med., Aug. 2013, 369(9):819-829.

Hansson, "VEGF-A modified mRNA in diabetic wound healing and future treatment opportunities," Presentation at 4th International mRNA Health Conference, Boston, Nov. 1, 2016, 11 pages.

International Preliminary Report on Patentability in International Application No. PCT/US2017/036188, dated Dec. 11, 2018, 13 pages.

International Preliminary Report on Patentability in International Application No. PCT/US2018/058541, dated May 20, 2020, 6 pages.

International Search Report in International Application No. PCT/US2018/058541, dated Feb. 12, 2019, 4 pages.

International Search Report in International Application No. PCT/US2020/032241, dated Sep. 9, 2020, 7 pages.

Kaczmarek et al., "Advances in the delivery of RNA therapeutics: from concept to clinical reality," Genome Med., Jun. 2017, 9:60:1-16.

Liu et al., "Driving vascular endothelial cell fate of human multipotent Isl1+ heart progenitors with VEGF modified mRNA," Cell Research, Oct. 2013, 23(10):1172-1186.

Mullard, "mRNA-based drug approaches Phase I milestone," Nature Reviews Drug Discovery, Sep. 2016, 15(9):595.

Rudin et al., "Delivery of a Liposomal c-raf-1 Antisense Oligonucleotide by Weekly Bolus Dosing in Patients with Advanced Solid Tumors: A Phase I Study," Clin. Cancer Res., Nov. 2004, 10(21):7244-7251.

Science [online], "What mRNA is Good For, And What It Maybe Isn't," Jun. 29, 2021, retrieved on Sep. 1, 2021, retrieved from URL <https://www.science/org/content/blog-post/what-mrna-good-and-what-it-maybe-isnt-t>, 14 pages.

United States Court of Appeals for the Federal Circuit, "In re James F. Crish and Richard L. Eckert." Case 04/1075, U.S. Appl. No. 08/822,509, decided, Dec. 21, 2004, 13 pages.

Written Opinion of the International Searching Authority issued in International Application No. PCT/US2020/032241, dated Sep. 9, 2020, 9 pages.

Xue et al., "Lipid-Based Nanocarriers for RNA Delivery," Curr. Pharm Des., Nov. 2015, 21(22):3140-3147.

Zangi et al., "Modified mRNA directs the fate of heart progenitor cells and induces vascular regeneration after myocardial infarction," Nature Biotechnology, Oct. 2012, 31(10):898-911.

Zhang et al., "Implications of pharmacokinetic behavior of lipoplex for its inflammatory toxicity," Adv. Drug Deliv. Rev., Apr. 2005, 57(5):689-698.

\* cited by examiner

FIG. 1A

5'-Cap | 5'-UTR | Start | Coding Region | Stop | 3'-UTR | Poly (A) tail

5'                                                                    3'

FIG. 1B

5' $^{7Me}G_{ppp}G_{2'OMe}$GGAAAUAAGAGAGAAAAAGAAGAGUAAGAAGAAAUAUAAGAGCCACCAUGAACUUUCUGCUGUCUUG
GGUGCAUUGGAGGGAGCCUUGCUGCUCUACCUCCAAGCCUGCCAAGGUCCAAGGCUGCACCAUGCCAAGCAGAAG
GAGGAGGGCAGAAUCAUCUUCCAGGAGUUCAAGGAUGAGUCAGCGCUACUGCAUCCAACUGCCAUCGAG
ACCCUGGUGGACAUCUUCCAGGAGUACCCUGAUGAGAUCGAGUACAUCAAGCCAUCCUGUGUGCCCUGAU
GCGAUGCGGGGGGAUCAAGAGGGCUGCAAUGACCACCAUGAGAGAGUCCAACAACAAGACCAUGCAG
AUUAUGCGGGGGAUCAAAGAGAUAAGAGCAAGAGCAAGAAAAUCCCUGGGCCUUGCUCAGAGCGGAGAAGCAUUGUUUGUA
AGACCAAAGAGAUAAGAGCAAGAGCAAGAAAAUCCCUGGGCCUUGCUCAGAGCGGAGAAGCAUUGUUUGUA
CAAGAUCCGCAGACGUGUAAUGAGCUCAAAACACAGACUGCAAAAUCCCUGCAAAAUGAGCUUGAGUUAAAC
GAACGUUACUUGCAAGCUGAGUAGACAAGGCUGGAUAAUAAGGCUGGAGGCAAGGCCUGCAUGCCUUCUGCCCC
UUGGGCCCUCCCCAGCCCUCCCCGUACCCCGGGUCUUUGAAUAAAGUCUGAGUGGG
CGGCAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAUCUAG$_{OH}$3'

Where:
A, C, G & U = AMP, CMP, GMP & N1-methyl-pseudoUMP, respectively
Me = methyl
p = inorganic phosphate

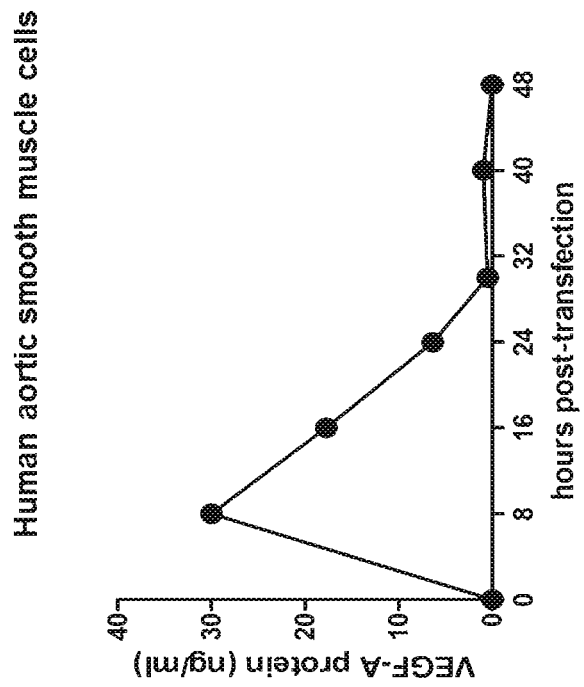
FIG. 2A
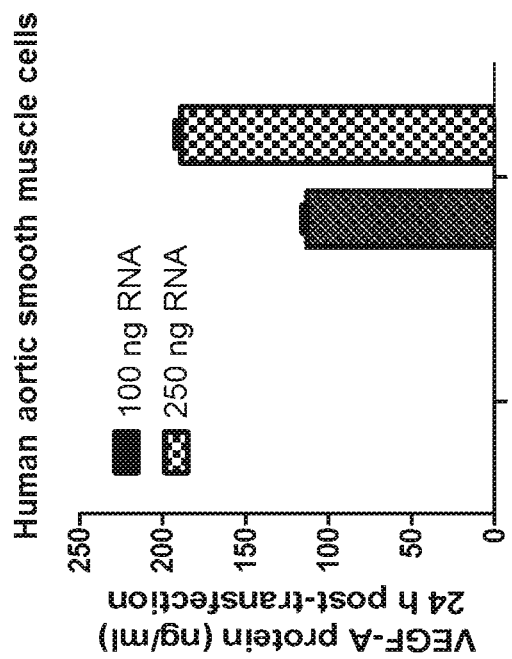
FIG. 2B
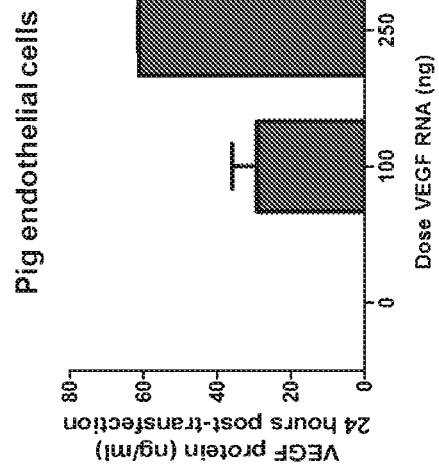
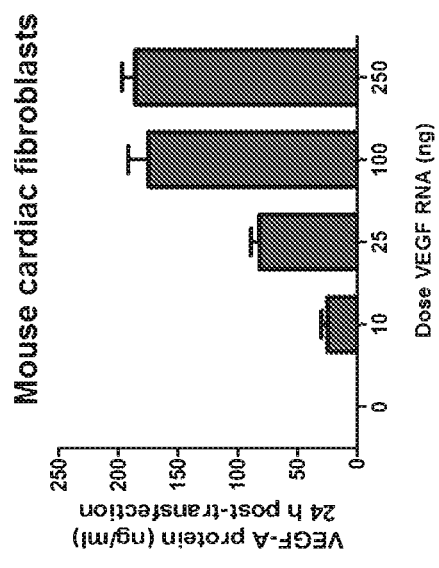
FIG. 2C

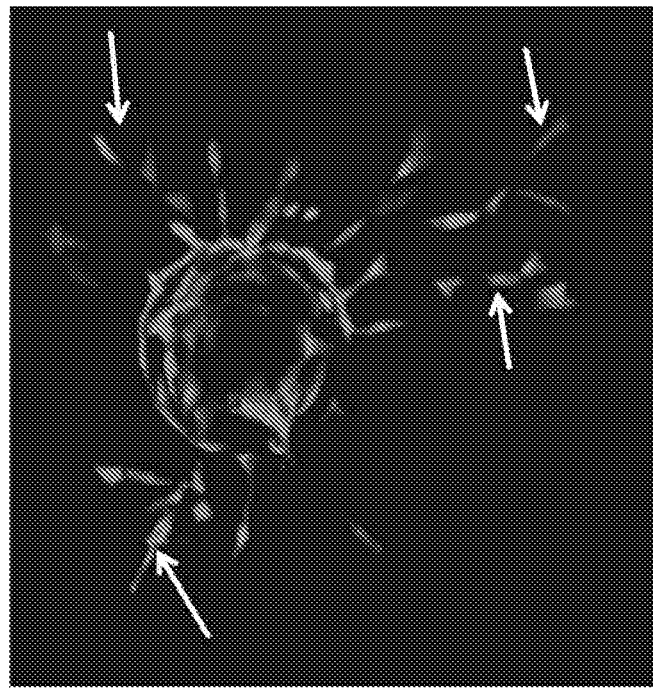
FIG. 5C RNA-produced VEGF-A
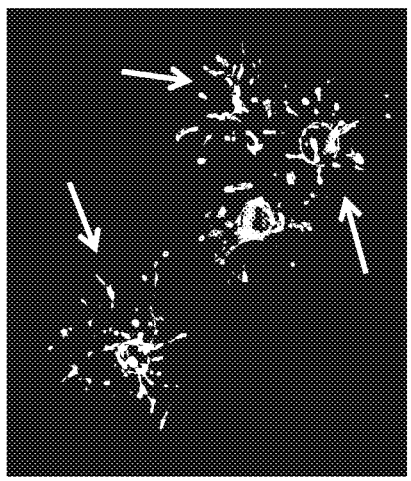
FIG. 5B RNA-produced VEGF-A
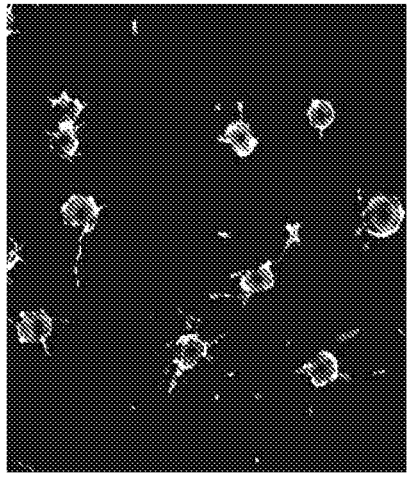
FIG. 5A control

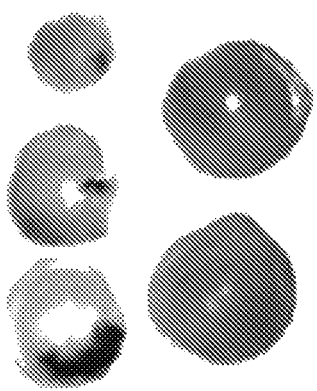
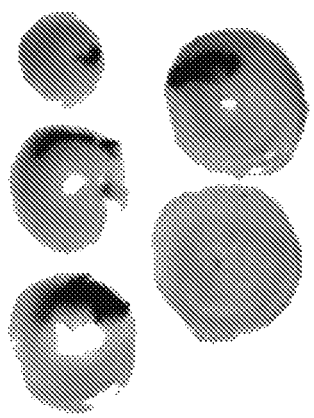
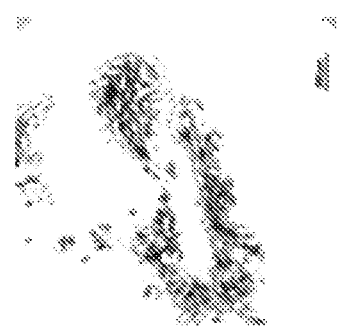
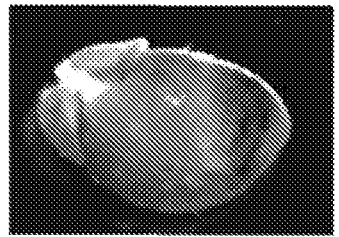
FIG. 11D
FIG. 11C
FIG. 11B
FIG. 11A

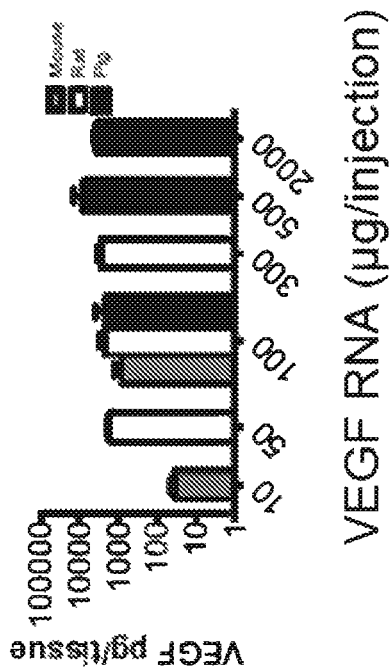
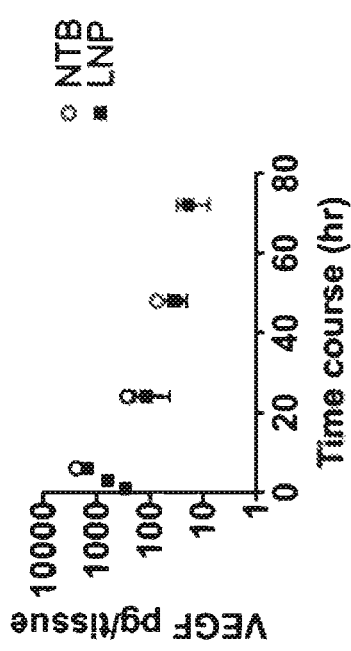
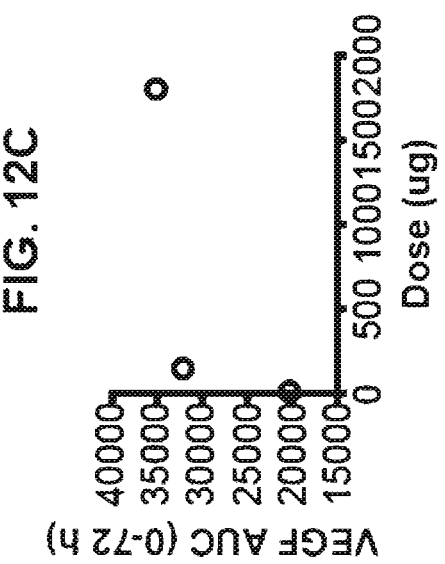

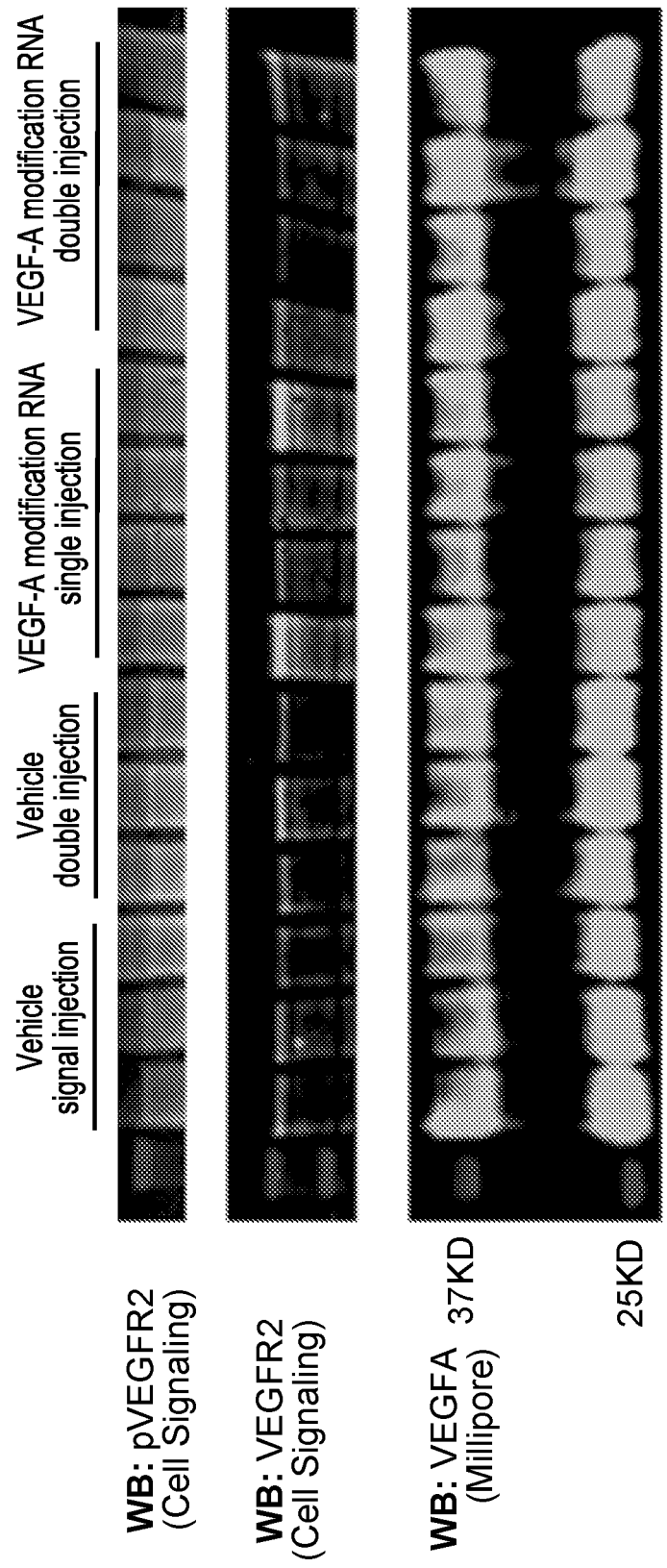
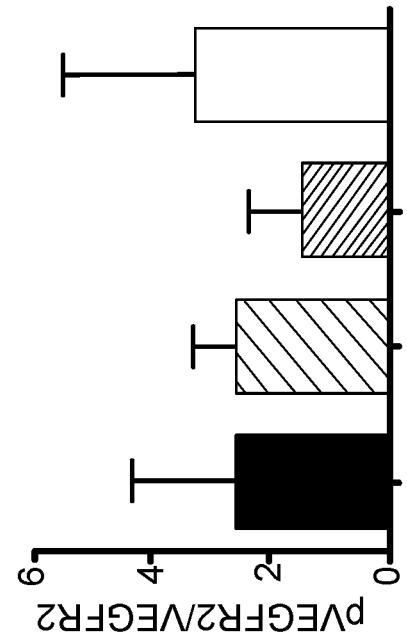
FIG. 30

MODIFIED RNA ENCODING VEGF-A POLYPEPTIDES, FORMULATIONS, AND USES RELATING THERETO

1. FIELD

The disclosure relates to modified RNA molecules encoding VEGF-A polypeptides and formulations comprising the modified RNA. Aspects of the disclosure further relate to preparations and uses of formulations comprising the modified RNA in treating subjects suffering from diseases responsive to VEGF-A therapy.

2. BACKGROUND

Vascular endothelial growth factor A (VEGF-A) pathways play a central role in the control of cardiovascular physiological function in general, and arteriogenesis in particular. VEGF-A's roles include activation of nitric oxide (NO) signaling, vascular permeability, tumor angiogenesis, arteriogenesis, endothelial replication, and cell fate switch for multipotent cardiovascular progenitors. While inhibition of VEGF-A pathways via both small molecules and antibodies has become the standard of care in selected forms of cancer and macular degeneration, it has remained challenging to unlock the potential of augmenting VEGF-A pathways for potential therapeutic effects that include relaxing smooth muscle, promoting new vessel formation, and potentially reversing the defects in vascular response associated with diabetic vascular complications.

As such, a diverse number of methods have been attempted to allow clinically tractable approaches to control the spatial and temporal expression of VEGF-A in target tissues. However, each of the approaches has significant drawbacks: systemic VEGF-A protein approaches can result in significant hypotension and VEGF-A is rapidly degraded; viral encapsulated and naked VEGF-A DNA plasmids have limited temporal control of protein expression and the efficiency of in vivo expression can be highly variable and non-dose dependent; adenoviral vectors can activate the immune system; and naked RNA is labile, has low levels of transfection, and also can trigger immune activation. As a result, these limitations have restricted the applicability of VEGF-A as a therapeutic platform.

In some previous studies, the in vivo use of therapeutic RNAs, e.g., siRNAs, has been dependent on utilizing lipid-nanoparticles (LNPs) to protect the mRNA from degradation as well as for efficient transfection. Furthermore, attempts to reach therapeutic levels of RNAi therapy in organs other than liver have resulted in infusion related hypersensitivity reactions as well as hepatotoxicity, thus limiting their use for disease therapy in other organ systems (Rudin C. M. et al., Clin. Cancer Res., (2004) 10, 7244-7251). In addition, other variants of these LNPs have been used clinically for therapeutic uses in selected cases, but can cause dose-dependent tissue injury (Coelho T. et al., N Engl J Med, (2013) 369, 819-829). Examples of such dose-dependent toxicity effects of some lipid-based nucleic acid pharmaceutical formulations include infusion related reactions such as dyspnea, hypoxia, rigors, back pain, hypotension, and liver injury. Furthermore, while cationic lipids are typically included in lipid formulations of RNA therapeutics, e.g., siRNA, to improve RNA encapsulation and stability, some such lipids may exhibit dose dependent toxicities, such as disruption of the integrity of a membrane structure, cell lysis and necrosis, and/or alteration of the expression of multiple genes in undesirable manner (Xue H. Y., Curr Pharm Des., (2015) 21(22):3140-7). At preclinical and clinical levels, dose dependent systemic toxicities of lipoplexes have also been well-documented. Capture of lipoplexes by Kupffer cells in liver can trigger inflammatory responses, which may inflict damages to liver and result in elevated levels in major liver function indicators. Leukopenia and thrombocytopenia may also occur (Zhang J., Adv Drug Deliv Rev., (2005) 57(5): 689-698). Moreover, lipofectamine causes an immune/inflammatory response and cell death.

Accordingly, to avoid the potential immunogenicity of RNA and the dose-dependent toxicities associated with some LNPs, there is a need for alternative, less toxic formulations of modified RNAs encoding VEGF-A polypeptides, to deliver the modified RNAs at therapeutically appropriate levels in treating subjects suffering from diseases responsive to VEGF-A therapy.

3. SUMMARY

The disclosure relates to modified RNA molecules encoding VEGF-A polypeptides and formulations comprising the modified RNA. Also disclosed are the consequent benefits of VEGF-A modified RNA in these formulations for protein expression, producing therapeutics with less toxicity, and providing tools useful in treating subjects suffering from diseases responsive to VEGF-A therapy.

Certain embodiments of the present disclosure are summarized in the following paragraphs. This list is only exemplary and not exhaustive of all of the embodiments provided by this disclosure.

Embodiment 1. A composition comprising a modified RNA, preferably the modified RNA of SEQ ID NO: 1, encoding a VEGF-A polypeptide of SEQ ID NO: 2 and a buffer, preferably a citrate saline buffer, a phosphate-buffered saline (PBS) buffer, or a tromethamine (THAM) buffer, wherein the buffer is substantially free of divalent cations.

Embodiment 2. A formulation comprising a pharmaceutically acceptable amount of a modified RNA, preferably the modified RNA of SEQ ID NO: 1, encoding a VEGF-A polypeptide of SEQ ID NO: 2 and a buffer, preferably a citrate saline buffer, a phosphate-buffered saline (PBS) buffer, or a tromethamine (THAM) buffer, wherein the buffer is substantially free of divalent cations.

Embodiment 3. The formulation of embodiment 2, wherein said buffer substantially free of divalent cations is a citrate saline buffer.

Embodiment 4. The formulation of embodiment 3, wherein the citrate saline buffer is substantially free of calcium and magnesium.

Embodiment 5. The formulation of embodiment 3, wherein the citrate saline buffer contains no calcium or magnesium.

Embodiment 6. The formulation of embodiment 2, further comprising a pharmaceutically acceptable excipient.

Embodiment 7. The formulation of embodiment 6, wherein the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof.

Embodiment 8. A method of treating a subject suffering from a disease responsive to VEGF-A therapy, comprising administering to the subject the composition according to embodiment 1, and/or the formulation according to any one of embodiments 2-7.

Embodiment 9. The method of embodiment 8, wherein the buffer that is substantially free of divalent cations in said composition or formulation is a citrate saline buffer.

Embodiment 10. The method of embodiment 9, wherein the citrate saline buffer is substantially free of calcium and magnesium.

Embodiment 11. The method of embodiment 9, wherein the citrate saline buffer contains no calcium or magnesium.

Embodiment 12. The method of embodiment 8, wherein the formulation further comprises a pharmaceutically acceptable excipient.

Embodiment 13. The method of embodiment 12, wherein the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof.

Embodiment 14. The method of embodiment 8, wherein the disease is chosen from heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, and peripheral arterial disease.

Embodiment 15. The method of embodiment 8, wherein the disease is heart failure with reduced or preserved ejection fraction.

Embodiment 16. The method of embodiment 8, wherein the disease is post-MI cardiac dysfunction.

Embodiment 17. The method of embodiment 8, wherein the disease is ischemic heart disease.

Embodiment 18. The method of embodiment 8, wherein the disease is a vascular injury from trauma or surgery.

Embodiment 19. The method of embodiment 8, wherein the disease is a skin ulcer including a diabetic ulcer.

Embodiment 20. The method of embodiment 8, wherein the disease is critical limb ischemia.

Embodiment 21. The method of embodiment 8, wherein the disease is pulmonary hypertension.

Embodiment 22. The method of embodiment 8, wherein the disease is peripheral arterial disease.

Embodiment 23. The method of embodiment 8, wherein the composition or formulation is administered to the subject via intramuscular, intradermal, subcutaneous, intracardiac, or epicardiac route, through a portal vein catheter, through a coronary sinus catheter, and/or by direct administration into the area to be treated.

Embodiment 24. The method of embodiment 8, wherein the composition or formulation is administered to the subject intramuscularly.

Embodiment 25. The method of embodiment 8, wherein the composition or formulation is administered to the subject intradermally.

Embodiment 26. The method of embodiment 8, wherein the composition or formulation is administered to the subject subcutaneously.

Embodiment 27. The method of embodiment 8, wherein the composition or formulation is administered to the subject intracardially or epicardially, preferably at a fixed-dosage in multiple administrations.

Embodiment 28. The method of embodiment 8, wherein the composition or formulation is administered to the subject through a portal vein catheter, preferably at a fixed-dosage in multiple administrations.

Embodiment 29. The method of embodiment 8, wherein the composition or formulation is administered to the subject through a coronary sinus catheter, preferably at a fixed-dosage in multiple administrations.

Embodiment 30. The method of embodiment 8, wherein the composition or formulation is administered to the subject by direct administration into the area to be treated, preferably at a fixed-dosage in multiple administrations.

Embodiment 31. The method of embodiment 8, wherein the composition or formulation comprises a concentration of the modified RNA of between 0.1 and 1 µg/µL, preferably formulated in citrate saline buffer.

Embodiment 32. The method of embodiment 8, wherein the composition or formulation comprises a concentration of the modified RNA of between 1 and 10 µg/µL, preferably formulated in citrate saline buffer.

Embodiment 33. The method of embodiment 8, wherein the composition or formulation comprises a concentration of the modified RNA of between 10 and 50 µg/µL, preferably formulated in citrate saline buffer.

Embodiment 34. The method of embodiment 9, wherein the composition or formulation with citrate saline buffer is less toxic to the subject than a lipid-based composition or formulation.

Embodiment 35. A method for modulating a physiological process in a mammalian cell, tissue, or subject comprising contacting said mammalian cell, tissue, or subject with the composition according to embodiment 1, and/or the formulation according to any one of embodiments 2-7.

Embodiment 36. The method of embodiment 35, wherein the modulating is chosen from inducing angiogenesis, stimulating vascular cell proliferation, increasing proliferation and/or altering the fate of epicardial derived progenitor cells, upregulating endothelialization, inducing cardiac regeneration, increasing revascularization of tissue grafts for wound healing, improving vascular function, increasing tissue perfusion and new vessel formation, reducing scar tissue, and improving cardiac function.

Embodiment 37. The method of embodiment 35, wherein the modulating comprises inducing angiogenesis.

Embodiment 38. The method of embodiment 35, wherein the modulating comprises stimulating vascular cell proliferation.

Embodiment 39. The method of embodiment 35, wherein the modulating comprises increasing proliferation and/or altering the fate of epicardial derived progenitor cells.

Embodiment 40. The method of embodiment 35, wherein the modulating comprises upregulating endothelialization.

Embodiment 41. The method of embodiment 35, wherein the modulating comprises inducing cardiac regeneration.

Embodiment 42. The method of embodiment 35, wherein the modulating comprises increasing revascularization of tissue grafts for wound healing.

Embodiment 43. The method of embodiment 35, wherein the modulating comprises improving vascular function.

Embodiment 44. The method of embodiment 35, wherein the modulating comprises increasing tissue perfusion and new vessel formation.

Embodiment 45. The method of embodiment 35, wherein the modulating comprises reducing scar tissue.

Embodiment 46. The method of embodiment 35, wherein the modulating comprises improving cardiac function.

Embodiment 47. The method of embodiment 35, wherein the buffer that is substantially free of divalent cations in said composition or formulation is a citrate saline buffer.

Embodiment 48. The method of embodiment 47, wherein the citrate saline buffer is substantially free of calcium and magnesium.

Embodiment 49. The method of embodiment 47, wherein the citrate saline buffer contains no calcium or magnesium.

Embodiment 50. The method of embodiment 35, wherein the composition or formulation comprises a concentration of the modified RNA of between 0.1 and 1 µg/µL, preferably formulated in citrate saline buffer.

Embodiment 51. The method of embodiment 35, wherein the composition or formulation comprises a concentration of the modified RNA of between 1 and 10 µg/µL, preferably formulated in citrate saline buffer.

Embodiment 52. The method of embodiment 35, wherein the composition or formulation comprises a concentration of the modified RNA of between 10 and 50 µg/µL, preferably formulated in citrate saline buffer.

Embodiment 53. A method for expressing VEGF-A in a mammalian cell or tissue, comprising contacting said mammalian cell or tissue with the composition according to embodiment 1, and/or the formulation according to any one of embodiments 2-7.

Embodiment 54. The method of embodiment 53, wherein the buffer that is substantially free of divalent cations in said composition or formulation is a citrate saline buffer.

Embodiment 55. The method of embodiment 54, wherein the citrate saline buffer is substantially free of calcium and magnesium.

Embodiment 56. The method of embodiment 54, wherein the citrate saline buffer contains no calcium or magnesium.

Embodiment 57. The method of embodiment 53, wherein the composition or formulation comprises a concentration of the modified RNA of between 0.1 and 1 µg/µL, preferably formulated in citrate saline buffer.

Embodiment 58. The method of embodiment 53, wherein the composition or formulation comprises a concentration of the modified RNA of between 1 and 10 µg/µL, preferably formulated in citrate saline buffer.

Embodiment 59. The method of embodiment 53, wherein the composition or formulation comprises a concentration of the modified RNA of between 10 and 50 µg/µL, preferably formulated in citrate saline buffer.

Embodiment 60. A method of producing VEGF-A in a subject, comprising administering to said subject the composition according to embodiment 1, and/or the formulation according to any one of embodiments 2-7.

Embodiment 61. The method of embodiment 60, wherein the buffer that is substantially free of divalent cations in said composition or formulation is a citrate saline buffer.

Embodiment 62. The method of embodiment 61, wherein the citrate saline buffer is substantially free of calcium and magnesium.

Embodiment 63. The method of embodiment 61, wherein the citrate saline buffer contains no calcium or magnesium.

Embodiment 64. The method of embodiment 60, wherein the formulation further comprises a pharmaceutically acceptable excipient.

Embodiment 65. The method of embodiment 64, wherein the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof.

Embodiment 66. The method of embodiment 60, wherein the subject is suffering from a disease responsive to VEGF-A therapy.

Embodiment 67. The method of embodiment 66, wherein the disease is chosen from heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, and peripheral arterial disease.

Embodiment 68. The method of embodiment 66, wherein the disease is heart failure with reduced or preserved ejection fraction.

Embodiment 69. The method of embodiment 66, wherein the disease is post-MI cardiac dysfunction.

Embodiment 70. The method of embodiment 66, wherein the disease is ischemic heart disease.

Embodiment 71. The method of embodiment 66, wherein the disease is a vascular injury from trauma or surgery.

Embodiment 72. The method of embodiment 66, wherein the disease is a skin ulcer including a diabetic ulcer.

Embodiment 73. The method of embodiment 66, wherein the disease is critical limb ischemia.

Embodiment 74. The method of embodiment 66, wherein the disease is pulmonary hypertension.

Embodiment 75. The method of embodiment 66, wherein the disease is peripheral arterial disease.

Embodiment 76. The method of embodiment 60, wherein the composition or formulation is administered to the subject via intramuscular, intradermal, subcutaneous, intracardiac, or epicardiac route, through a portal vein catheter, through a coronary sinus catheter, and/or by direct administration into the area to be treated.

Embodiment 77. The method of embodiment 60, wherein the composition or formulation is administered to the subject intramuscularly.

Embodiment 78. The method of embodiment 60, wherein the composition or formulation is administered to the subject intradermally.

Embodiment 79. The method of embodiment 60, wherein the composition or formulation is administered to the subject subcutaneously.

Embodiment 80. The method of embodiment 60, wherein the composition or formulation is administered to the subject intracardially or epicardially, preferably at a fixed-dosage in multiple administrations.

Embodiment 81. The method of embodiment 60, wherein the composition or formulation is administered to the subject through a portal vein catheter, preferably at a fixed-dosage in multiple administrations.

Embodiment 82. The method of embodiment 60, wherein the composition or formulation is administered to the subject through a coronary sinus catheter, preferably at a fixed-dosage in multiple administrations.

Embodiment 83. The method of embodiment 60, wherein the composition or formulation is administered to the subject by direct administration into the area to be treated, preferably at a fixed-dosage in multiple administrations.

Embodiment 84. The method of embodiment 60, wherein the composition or formulation comprises a concentration of the modified RNA of between 0.1 and 1 µg/µL, preferably formulated in citrate saline buffer.

Embodiment 85. The method of embodiment 60, wherein the composition or formulation comprises a concentration of the modified RNA of between 1 and 10 µg/µL, preferably formulated in citrate saline buffer.

Embodiment 86. The method of embodiment 60, wherein the composition or formulation comprises a concentration of the modified RNA of between 10 and 50 μg/μL, preferably formulated in citrate saline buffer.

Embodiment 87. A method for preparing a composition or formulation, comprising combining a modified RNA, preferably the modified RNA of SEQ ID NO: 1, encoding a VEGF-A polypeptide of SEQ ID NO: 2 with a buffer, preferably a citrate saline buffer, a phosphate-buffered saline (PBS) buffer, or a tromethamine (THAM) buffer into the composition or formulation, wherein the buffer is substantially free of divalent cations, and wherein the composition or formulation is effective for treating a subject suffering from a disease responsive to VEGF-A therapy.

Embodiment 88. The method of embodiment 87, wherein the citrate saline buffer is substantially free of calcium and magnesium.

Embodiment 89. The method of embodiment 87, wherein the citrate saline buffer contains no calcium or magnesium.

Embodiment 90. The method of embodiment 87, wherein the composition or formulation comprises a concentration of the modified RNA of between 0.1 and 1 μg/μL, preferably formulated in citrate saline buffer.

Embodiment 91. The method of embodiment 87, wherein the composition or formulation comprises a concentration of the modified RNA of between 1 and 10 μg/μL, preferably formulated in citrate saline buffer.

Embodiment 92. The method of embodiment 87, wherein the composition or formulation comprises a concentration of the modified RNA of between 10 and 50 μg/μL, preferably formulated in citrate saline buffer.

Embodiment 93. The method of embodiment 87, wherein the composition or formulation with citrate saline buffer is less toxic to the subject than a lipid-based composition or formulation.

Embodiment 94. A method of reducing toxicity of a VEGF-A treatment in a subject, comprising formulating a modified RNA, preferably the modified RNA of SEQ ID NO: 1, encoding a VEGF-A polypeptide of SEQ ID NO: 2 with a buffer, preferably a citrate saline buffer, a phosphate-buffered saline (PBS) buffer, or a tromethamine (THAM) buffer into a composition or formulation, wherein the buffer is substantially free of divalent cations.

Embodiment 95. The method of embodiment 94, wherein the citrate saline buffer is substantially free of calcium and magnesium.

Embodiment 96. The method of embodiment 94, wherein the citrate saline buffer contains no calcium or magnesium.

Embodiment 97. A nucleic acid sequence comprising an in vitro transcription template for the generation of a modified RNA, preferably the modified RNA of SEQ ID NO: 1, encoding a VEGF-A polypeptide of SEQ ID NO: 2.

Embodiment 98. A method for increasing wound healing in a mammalian tissue or a subject comprising contacting said mammalian tissue or subject with the composition according to embodiment 1, and/or the formulation according to any one of embodiments 2-7.

Embodiment 99. A method for inducing neovascularization in a mammalian tissue or a subject comprising contacting said mammalian tissue or subject with the composition according to embodiment 1, and/or the formulation according to any one of embodiments 2-7.

Embodiment 100. A method for inducing angiogenesis in a mammalian tissue or a subject comprising contacting said mammalian tissue or subject with the composition according to embodiment 1, and/or the formulation according to any one of embodiments 2-7.

Embodiment 101. A method for inducing vasodilation in a mammalian tissue or a subject comprising contacting said mammalian tissue or subject with the composition according to embodiment 1, and/or the formulation according to any one of embodiments 2-7.

Embodiment 102. A method for inducing blood flow upregulation in a mammalian tissue or a subject comprising contacting said mammalian tissue or subject with the composition according to embodiment 1, and/or the formulation according to any one of embodiments 2-7.

Embodiment 103. A method for increasing capillary and/or arteriole density in a mammalian tissue or a subject comprising contacting said mammalian tissue or subject with the composition according to embodiment 1, and/or the formulation according to any one of embodiments 2-7.

Embodiment 104. A method for attenuating fibrosis in a mammalian tissue or a subject comprising contacting said mammalian tissue or subject with the composition according to embodiment 1, and/or the formulation according to any one of embodiments 2-7.

4. DESCRIPTION OF DRAWINGS

Those of skill in the art will understand that the drawings, described below, are for illustrative purposes only. The drawings are not intended to limit the scope of the present teachings in any way.

FIGS. 1A and 1B: The structure (FIG. 1A) and sequence (SEQ ID NO: 1, FIG. 1B) of the VEGF-A modified RNA used in the Examples.

FIGS. 2A, 2B, and 2C: Transfection of a higher dose of modified RNA resulted in the production of more VEGF-A protein in human aortic smooth muscle cells (FIG. 2A). A time course of VEGF-A protein production after transfection with modified RNA in human aortic smooth muscle cells (FIG. 2B). VEGF-A protein production in mouse cardiac fibroblasts (FIG. 2C, left panel) and pig endothelial cells (FIG. 2C, right panel) after transfection with modified RNA.

Figure 3B:
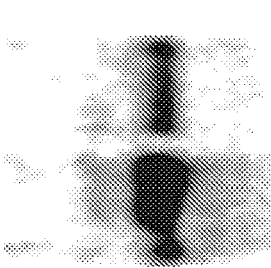
Figure 3C:
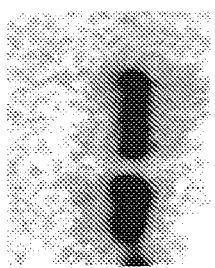

FIGS. 3A, 3B, and 3C: VEGF-A protein produced from VEGF-A modified RNA induced phosphorylation of VEGFR2 in human endothelial cells (FIG. 3A) and activation of downstream signaling pathways eNOS in human endothelial cells (FIG. 3B) and Akt in mouse cardiac fibroblasts (FIG. 3C).

Figure 4A:
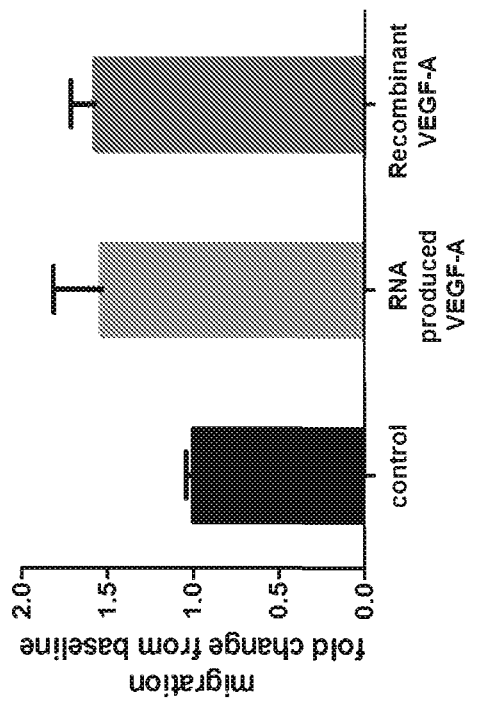
Figure 4B:
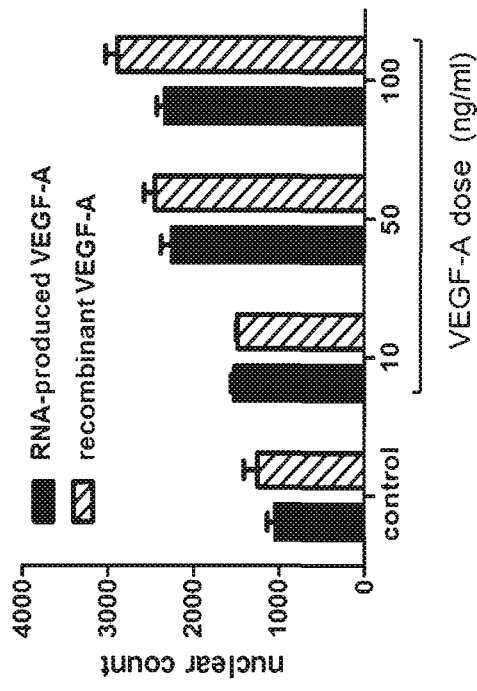
Figure 4C:
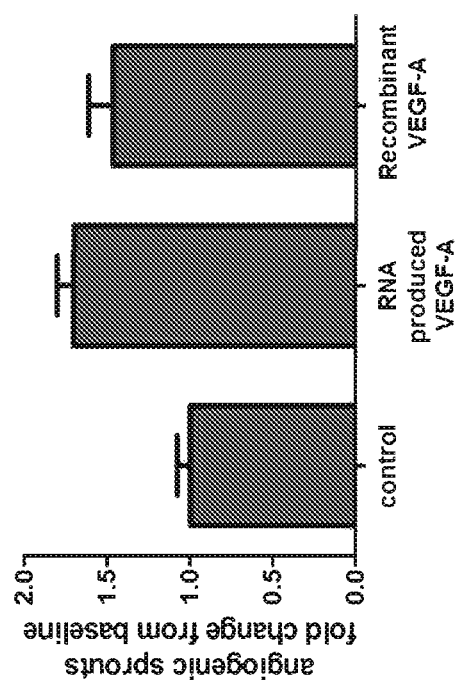

FIGS. 4A, 4B, and 4C: VEGF-A protein produced from VEGF-A modified RNA affects several critical steps in the angiogenic process. VEGF-A protein produced by VEGF-A modified RNA increased proliferation (FIG. 4A) and migration (FIG. 4B) of cultured human endothelial cells. VEGF-A protein produced by VEGF-A modified RNA increased angiogenic sprout formation in 3D culture with beads coated with endothelial cells (FIG. 4C).

FIGS. 5A, 5B, and 5C: Images of angiogenic sprout formation from beads coated with endothelial cells and treated with control media (FIG. 5A) or conditioned media with modified RNA-produced VEGF-A (FIG. 5B). Enlarged view of angiogenic sprout formation from beads coated with endothelial cells and treated with modified RNA-produced VEGF-A (FIG. 5C).

Figure 6A:
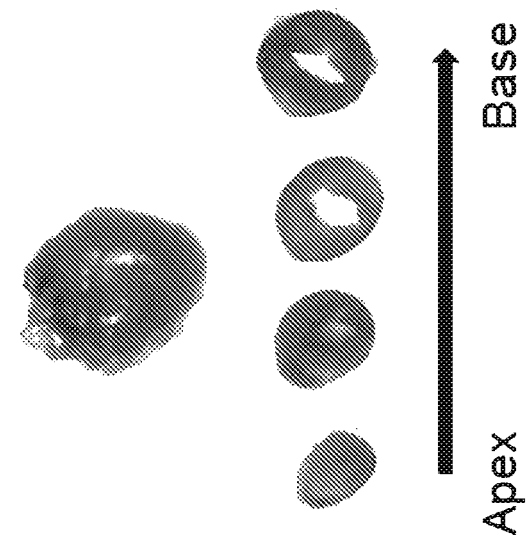
Figure 6B:
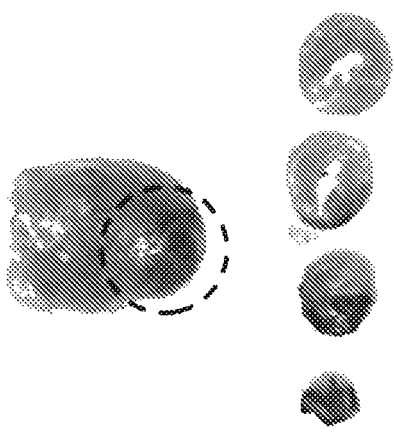
Figure 6C:
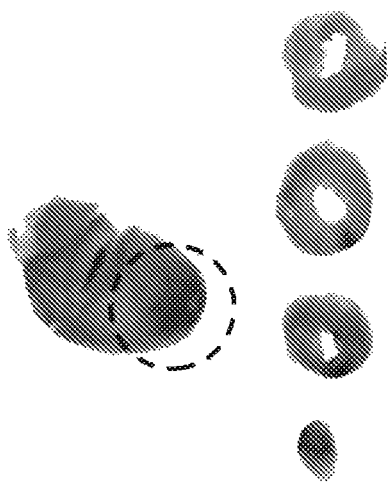

FIGS. 6A, 6B, and 6C: Comparison of X-gal staining indicative of β-galactosidase enzyme produced in mouse hearts following a 50 μL intracardiac injection of citrate saline (FIG. 6A), LacZ modified RNA formulated in lipofectamine (100 μg, FIG. 6B) or in citrate saline buffer (150 μg, FIG. 6C).

Figure 7:
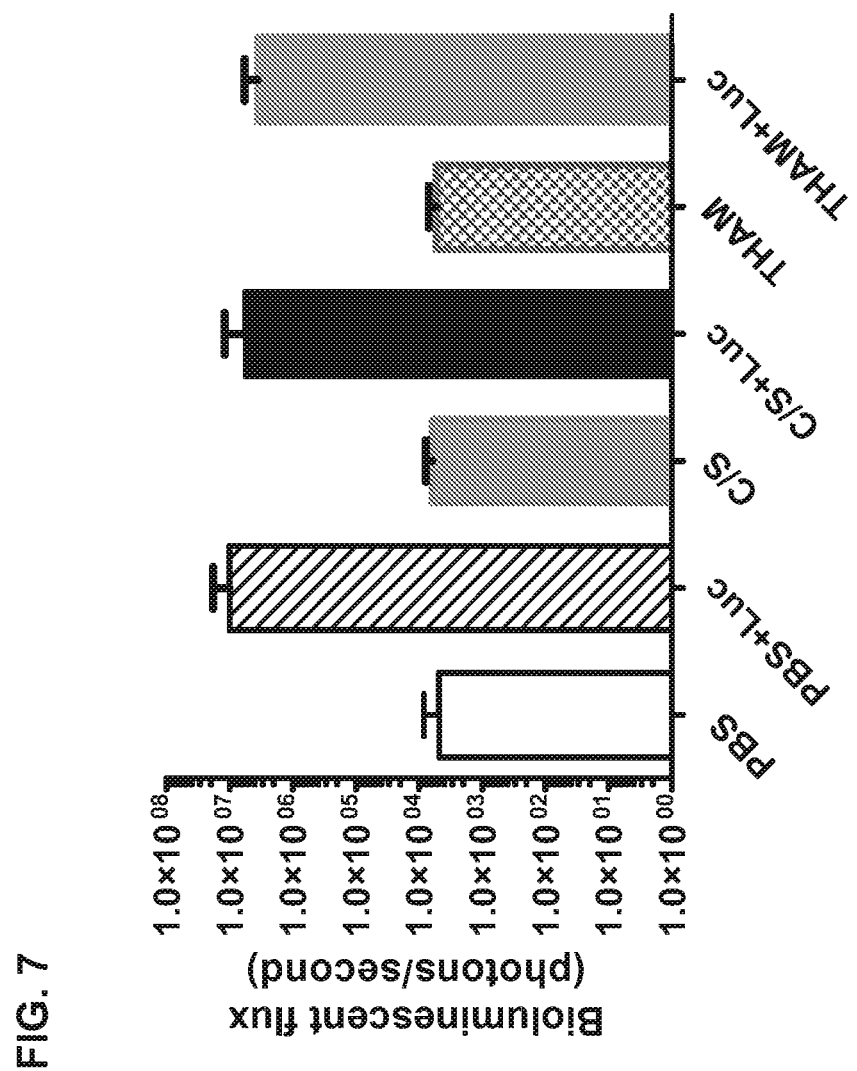

FIG. 7: Assessment of luciferase protein produced in mouse hearts following intracardiac injection of firefly luciferase modified RNA formulated in Phosphate-Buffered Saline (PBS, n=3), Citrate Saline (C/S, n=6), or Tromethamine AKA 2-amino-2-(hydroxymethyl)-1,3-propanediol (THAM, n=3). PBS, C/S and THAM buffers (n=2/group) were used as negative control.

Figure 8B:
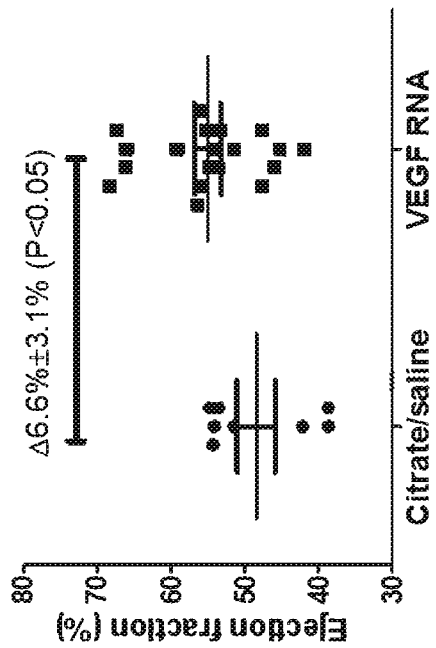
Figure 8D:
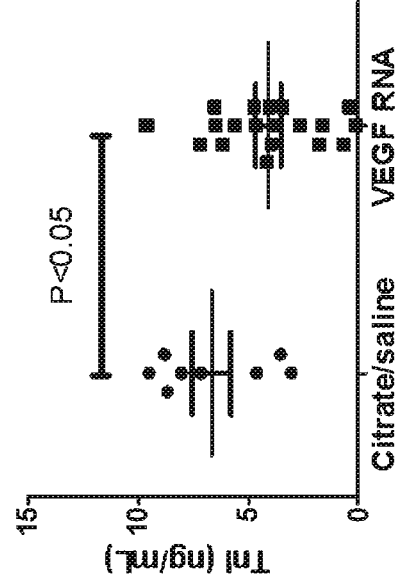
Figure 8A:
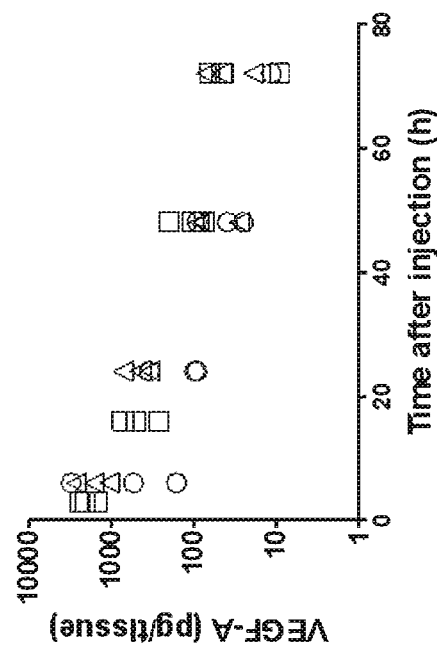

FIGS. 8A, 8B, 8C, and 8D: Cardiac levels of VEGF-A protein at different time points following intracardiac injection of 15 μg (circles), 150 μg (squares) or 1800 μg (triangles) of citrate saline-formulated VEGF-A modified RNA in naïve rats (FIG. 8A). Comparison of left ventricular ejection fraction and infarct size (as % of left ventricular mass) in rats subjected to myocardial infarction and intracardially injected with citrate/saline or VEGF-A modified RNA (150 or 1800 μg formulated in citrate/saline). Ejection fraction (FIG. 8B) and infarct size (FIG. 8C) were assessed by cardiac magnetic resonance imaging 8 days after the induction of infarction and injection. Levels of cardiac troponin I (TnI) in venous blood drawn from rats one day after induction of myocardial infarction and intracardially injected with citrate/saline or VEGF-A modified RNA formulated in citrate/saline (FIG. 8D).

Figure 9B:
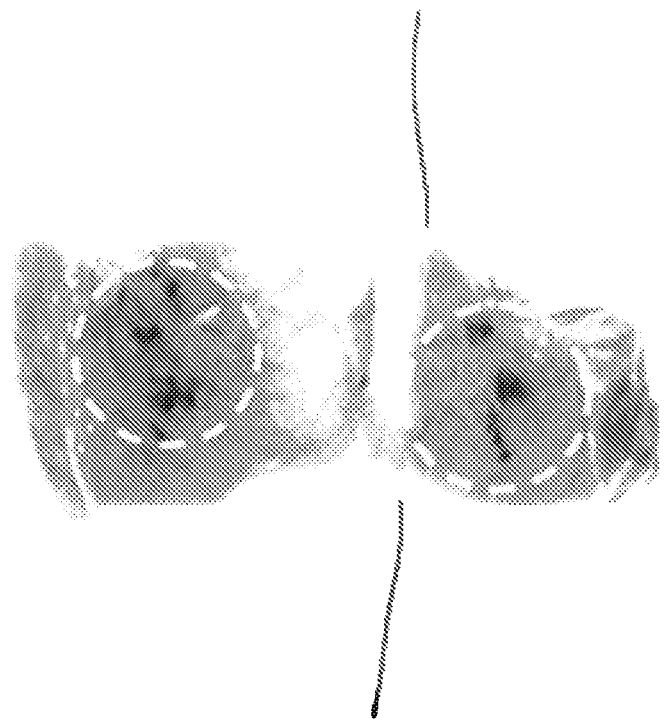
Figure 9A:

FIGS. 9A and 9B: Representative samples harvested from the left ventricular free wall in Göttingen mini pigs epicardially injected with LacZ modified RNA (100 μg at 3 separate injection sites). The tissue was harvested 6 hours after the injection and X-gal stained for 18 hours. The left sample shows staining in tissue injected with LacZ modified RNA formulated in lipofectamine (FIG. 9A) and the right sample tissue injected with LacZ modified RNA formulated in citrate/saline (FIG. 9B), respectively.

Figure 10:
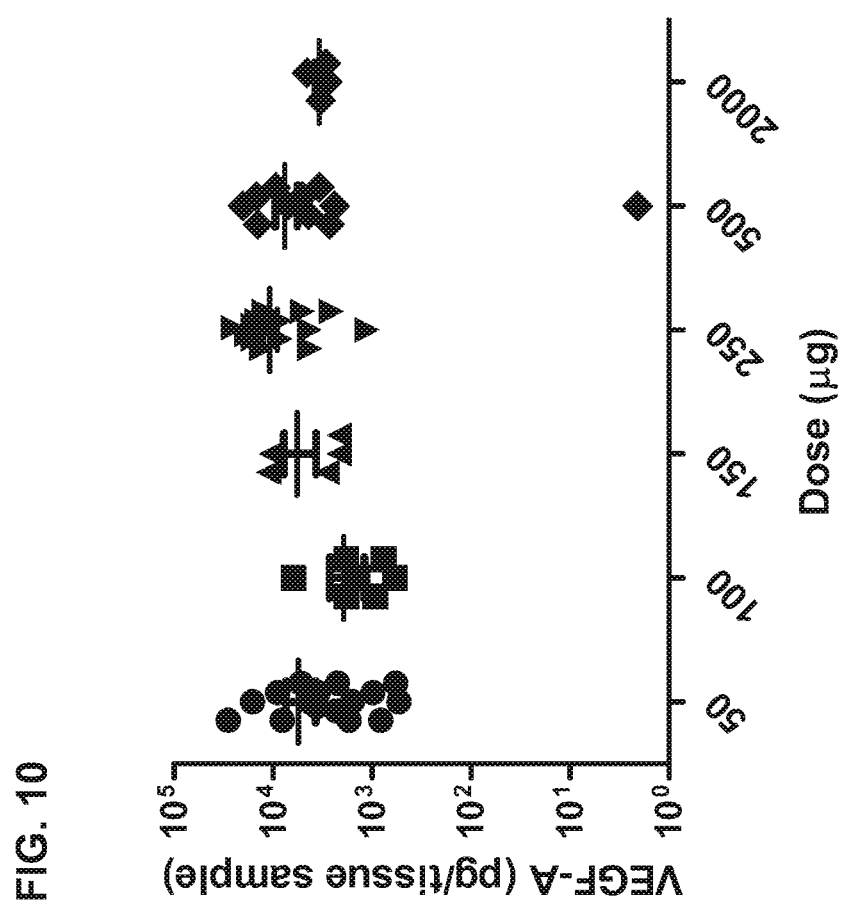

FIG. 10: Human VEGF-A protein in pig left ventricular tissue samples 6 hours following epicardial injection of varying doses of VEGF-A modified RNA in the Göttingen mini pig.

Figure 11E:
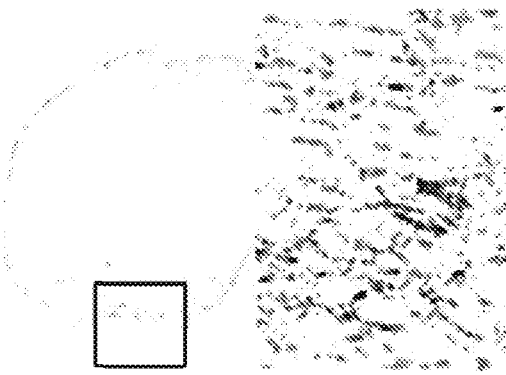
Figure 11F:
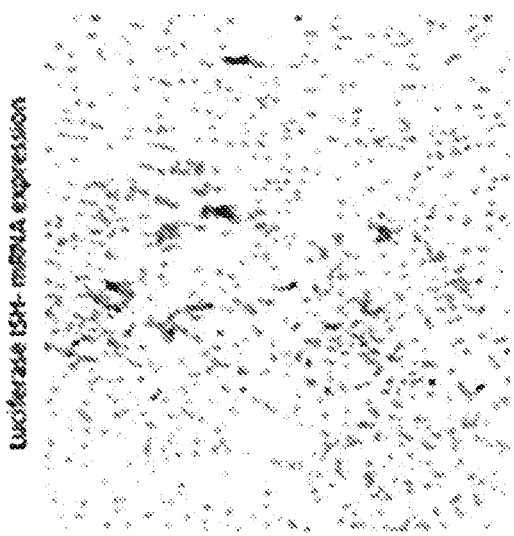
Figure 11G:
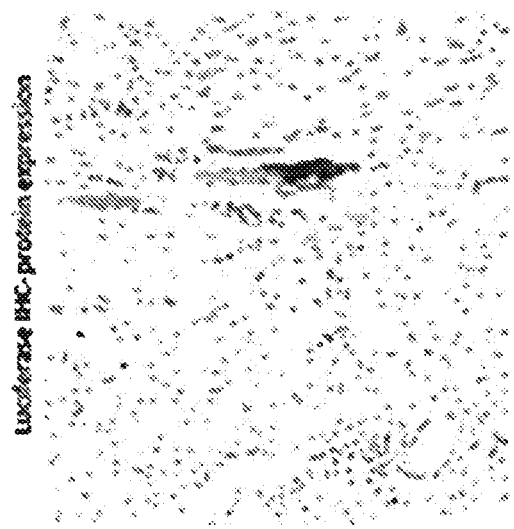

FIGS. 11A, 11B, 11C, 11D, 11E, 11F, and 11G: LacZ and luciferase modified RNA cardiac transfection and translation in a citrate saline buffer. 75 μg of LacZ modified RNA injected into the mouse heart with a citrate saline buffer. Production of β-galactosidase was found in approximately 10% of the left ventricle of the hearts (representative images in FIG. 11 A, FIG. 11C, and FIG. 11D). Enlarged view of X-gal staining showing production of β-galactosidase in the heart after injection of LacZ modified RNA (FIG. 11B). Luciferase modified RNA injected into heart. RNA in situ hybridization with luciferase probe revealed presence of luciferase modified RNA in the myocardium at the site of injection (FIG. 11E). Enlarged view of RNA in situ hybridization with luciferase probe showing presence of luciferase modified RNA (FIG. 11F). Immunohistochemistry revealed luciferase protein expression in the myocardium at the site of injection after injection of luciferase modified RNA (FIG. 11G).

FIGS. 12A, 12B, and 12C: VEGF-A protein expression after modified RNA injection to the heart with citrate/saline buffer is saturable and has similar pharmacokinetics across multiple species. VEGF-A protein pharmacokinetics after single cardiac injections of VEGF-A modified RNA formulated in citrate saline buffer (NTB) vs lipofectamine (LNP) in the mouse over 72 hours (FIG. 12A). Cross-species comparison of VEGF-A protein levels following increasing dosing of VEGF-A modified RNA in citrate saline (FIG. 12B). Rat pharmacokinetics of VEGF-A protein produced by increasing doses of VEGF-A modified RNA. Area under the curve (AUC) measurements for VEGF-A protein produced at 72 hours (FIG. 12C).

Figure 13B:
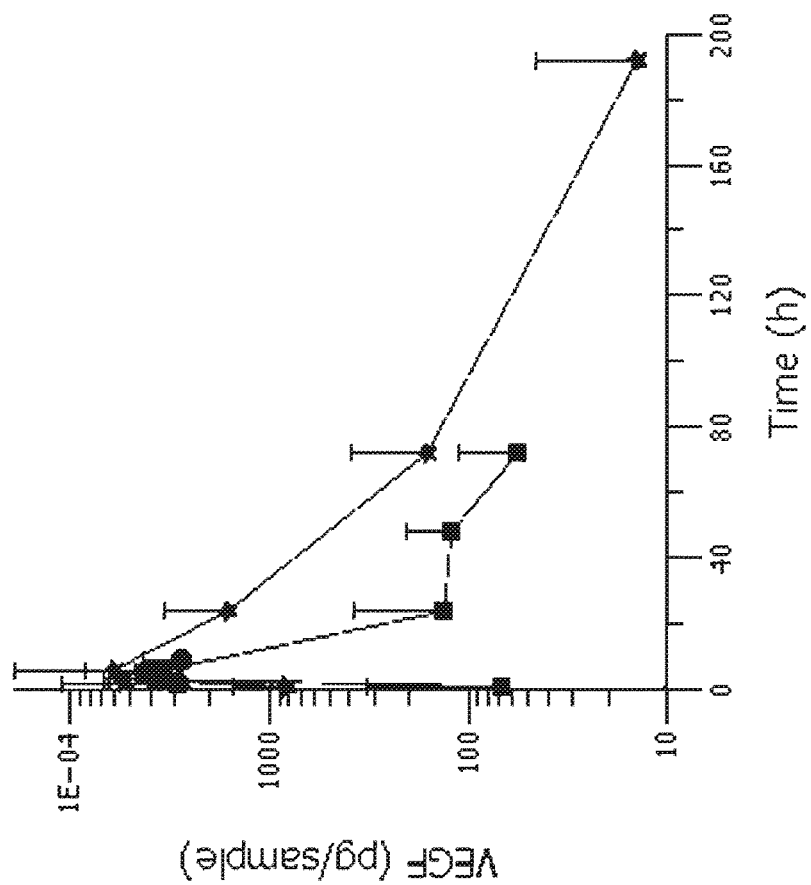
Figure 13A:
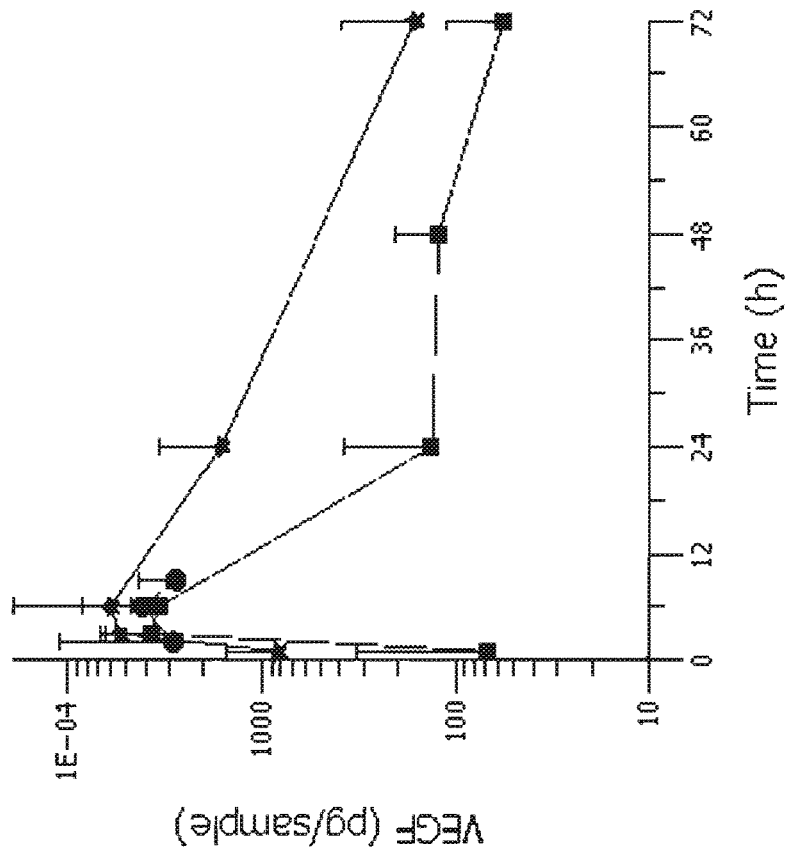

FIGS. 13A and 13B: Assessment of human VEGF-A protein production following intracardiac injection of human VEGF-A modified RNA in the mouse, rat and pig. Magnitude and time profiles (0 to 72 hours in FIG. 13A; 0 to 192 hours in FIG. 13B) of VEGF-A protein produced in the mouse (filled squares), rat (filled stars) and pig (filled circles) heart following an intracardiac injection of 100 μg VEGF-A modified RNA formulated in citrate/saline. Shown are geometric means±SD.

Figure 14:
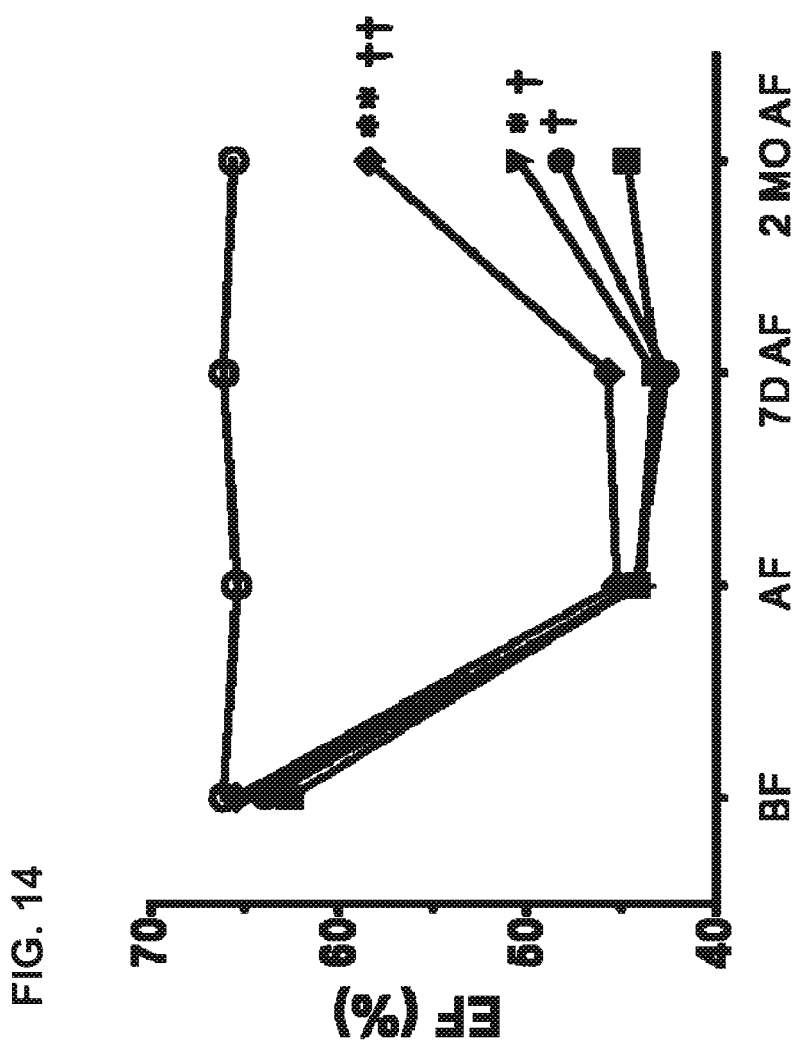

FIG. 14: Effects of human VEGF-A modified RNA and recombinant human VEGF-A on left ventricular ejection fraction (EF) in mini pigs subjected to myocardial infarction. Serial assessments of EF were carried out before (BF) and after (AF) a permanent occlusion of the left anterior descending coronary artery. A separate group of pigs were subjected to a sham procedure without coronary occlusion (open circles, n=5). Subsequent assessment of EF were then carried out at the time of study drug injection 7 days after the occlusion (7 D AF) and once more 2 months later (2 MO AF). At 7 D AF, the pigs were randomised to receive 20 epicardial injections (100 μL each) of either citrate/saline (filled squares, n=8) or VEGF-A modified RNA at a total dose of 1 mg (filled circles, n=8) or 10 mg (filled triangles, n=8) or recombinant human VEGF-A protein formulated in self-assembling nanofibers (filled diamonds, n=5), respectively. *; $P<0.05$ vs the citrate/saline control group at 2 MO AF, **; $P<0.01$ vs the citrate/saline control group at 2 MO AF, †; $P<0.001$ comparing change from 7 D AF until 2 MO AF, ††$P<0.0001$ comparing change from 7 D AF until 2 MO AF.

Figure 15:
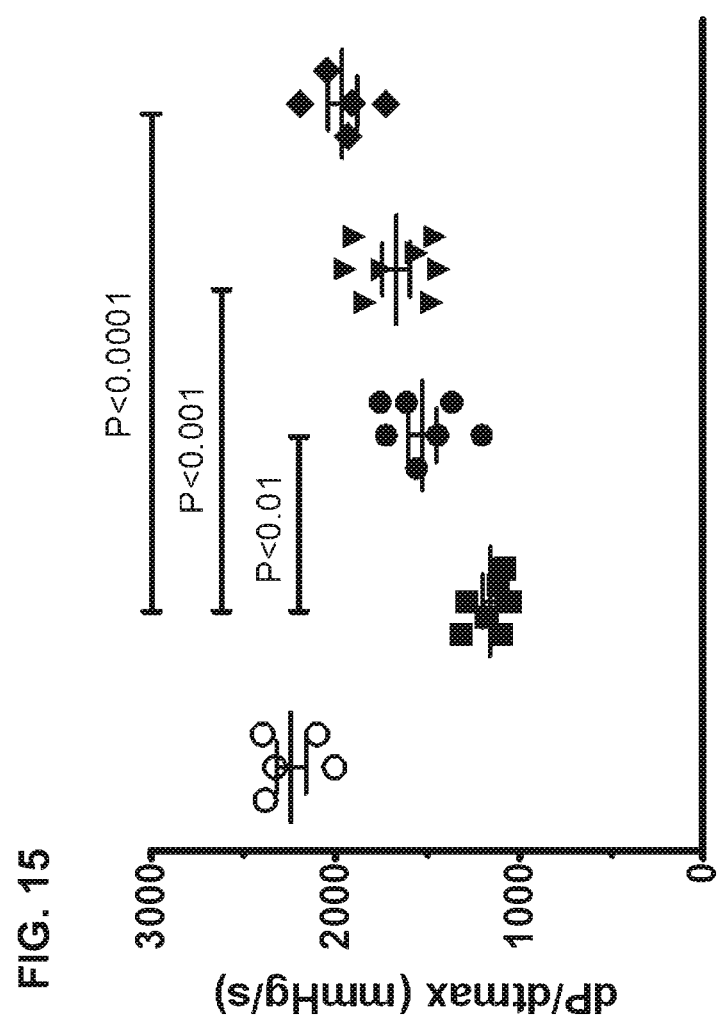

FIG. 15: Effects of human VEGF-A modified RNA and recombinant human VEGF-A on maximal left ventricular pressure development over time (dP/dt max) in mini pigs subjected to myocardial infarction. Mini pigs were subjected to a permanent occlusion of the left anterior descending coronary artery to induce myocardial infarction. A separate group of pigs were subjected to a sham procedure without coronary occlusion (open circles, n=5). Seven days later, infarcted pigs were randomised to a blinded epicardial injection of citrate/saline vehicle (2 mL, filled squares), 1 mg (filled circles) or 10 mg (filled triangles) VEGF-A modified RNA or recombinant human VEGF-A protein (200 ng) formulated in self-assembling nanofibers (filled diamonds). The dose/volume was administered as 20 separate injections (100 μL each) at the peri-infarct area. Left ventricular function was measured invasively 2 months after the injection. Shown are individual data and means±SEM.

Figure 16:
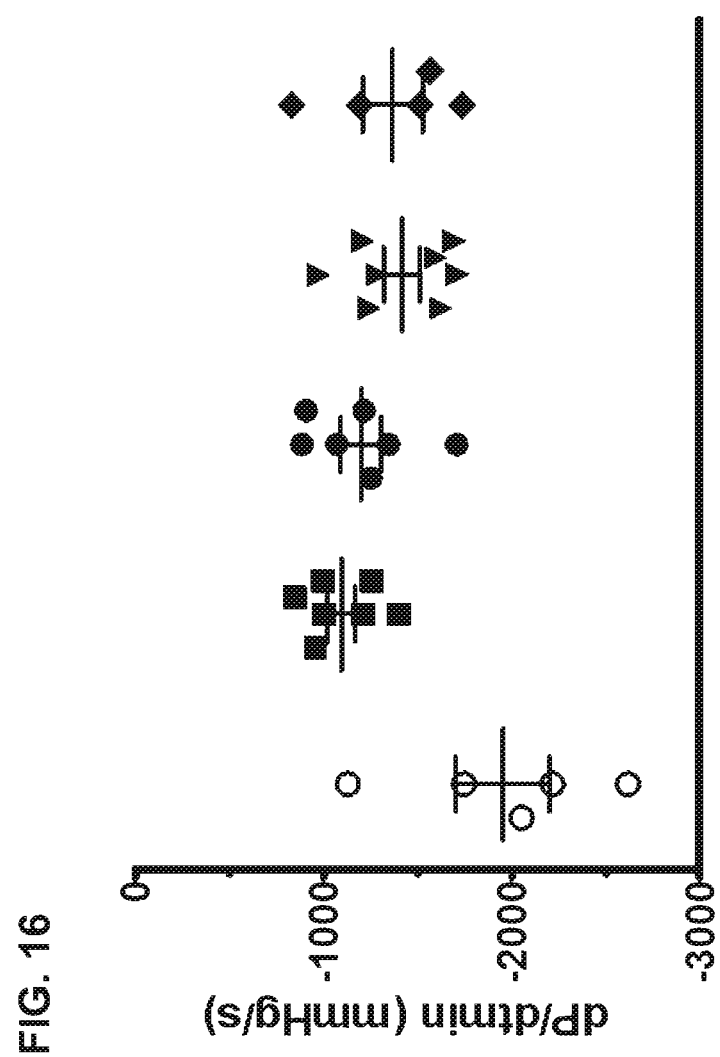

FIG. 16: Effects of human VEGF-A modified RNA and recombinant human VEGF-A on minimal left ventricular pressure development over time (dP/dt min) in mini pigs subjected to myocardial infarction. Mini pigs were subjected to a permanent occlusion of the left anterior descending coronary artery to induce myocardial infarction. A separate group of pigs were subjected to a sham procedure without coronary occlusion (open circles, n=5). Seven days later, infarcted pigs were randomised to a blinded epicardial injection of citrate/saline vehicle (2 mL, filled squares), 1 mg (filled circles) or 10 mg (filled triangles) VEGF-A modified RNA or recombinant human VEGF-A protein (200 ng) formulated in self-assembling nanofibers (filled diamonds). The dose/volume was administered as 20 separate injections (100 μL each) at the peri-infarct area. Left ventricular function was measured invasively 2 months after the injection. Shown are individual data and means±SEM.

Figure 17:
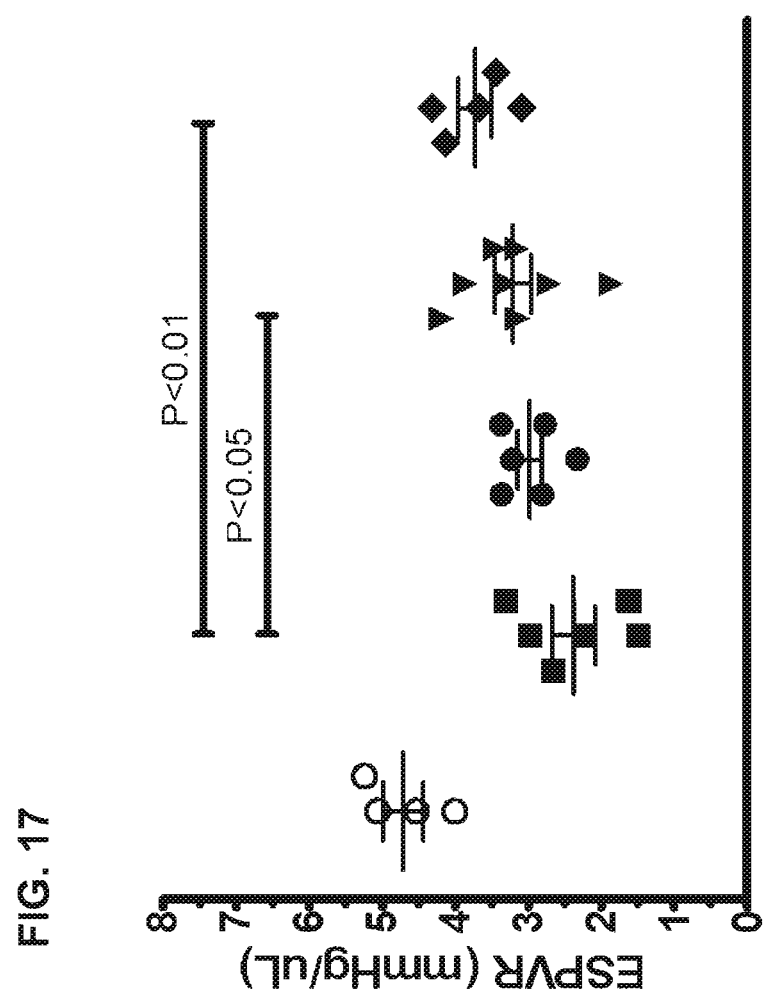

FIG. 17: Effects of human VEGF-A modified RNA and recombinant human VEGF-A on systolic function (inotropy, ESPVR) in mini pigs subjected to myocardial infarction. Mini pigs were subjected to a permanent occlusion of the left anterior descending coronary artery to induce myocardial infarction. A separate group of pigs were subjected to a sham procedure without coronary occlusion (open circles, n=5).

Seven days later, infarcted pigs were randomised to a blinded epicardial injection of citrate/saline vehicle (2 mL, filled squares), 1 mg (filled circles) or 10 mg (filled triangles) VEGF-A modified RNA or recombinant human VEGF-A protein (200 ng) formulated in self-assembling nanofibers (filled diamonds). The dose/volume was administered as 20 separate injections (100 μL each) at the peri-infarct area. Left ventricular function was measured invasively 2 months after the injection. Shown are individual data and means±SEM.

Figure 18:
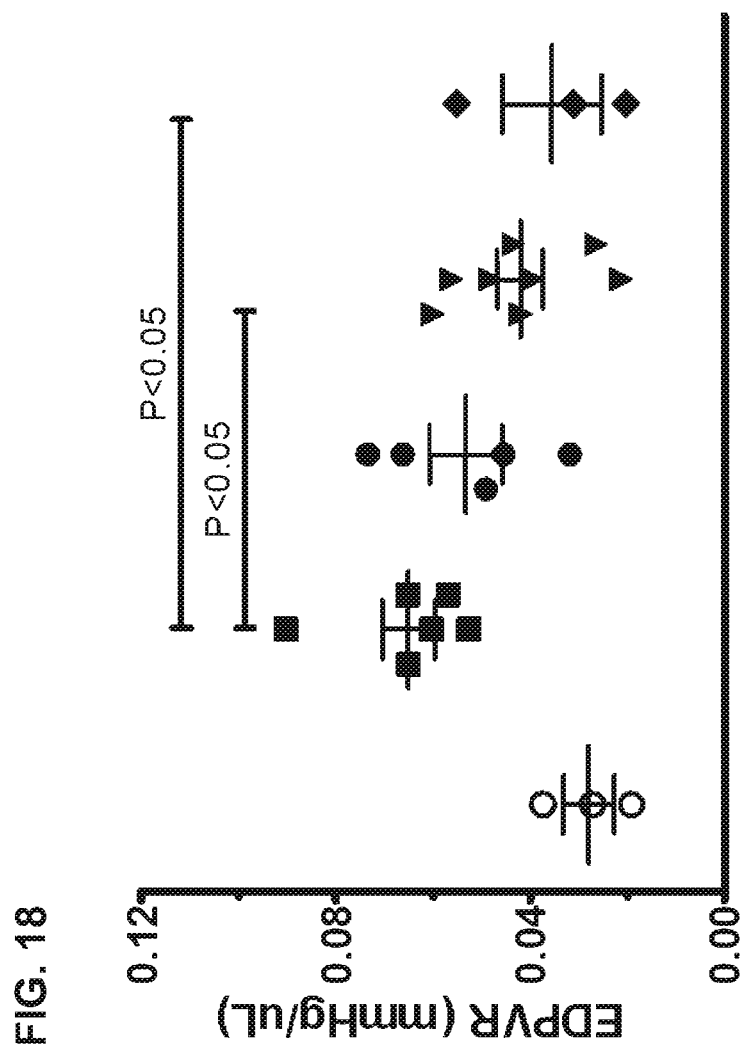

FIG. 18: Effects of human VEGF-A modified RNA and recombinant human VEGF-A on diastolic function (compliance, EDPVR) in mini pigs subjected to myocardial infarction. Mini pigs were subjected to a permanent occlusion of the left anterior descending coronary artery to induce myocardial infarction. A separate group of pigs were subjected to a sham procedure without coronary occlusion (open circles, n=5). Seven days later, infarcted pigs were randomised to a blinded epicardial injection of citrate/saline vehicle (2 mL, filled squares), 1 mg (filled circles) or 10 mg (filled triangles) VEGF-A modified RNA or recombinant human VEGF-A protein (200 ng) formulated in self-assembling nanofibers (filled diamonds). The dose/volume was administered as 20 separate injections (100 μL each) at the peri-infarct area. Left ventricular function was measured invasively 2 months after the injection. Shown are individual data and means±SEM.

Figure 19:
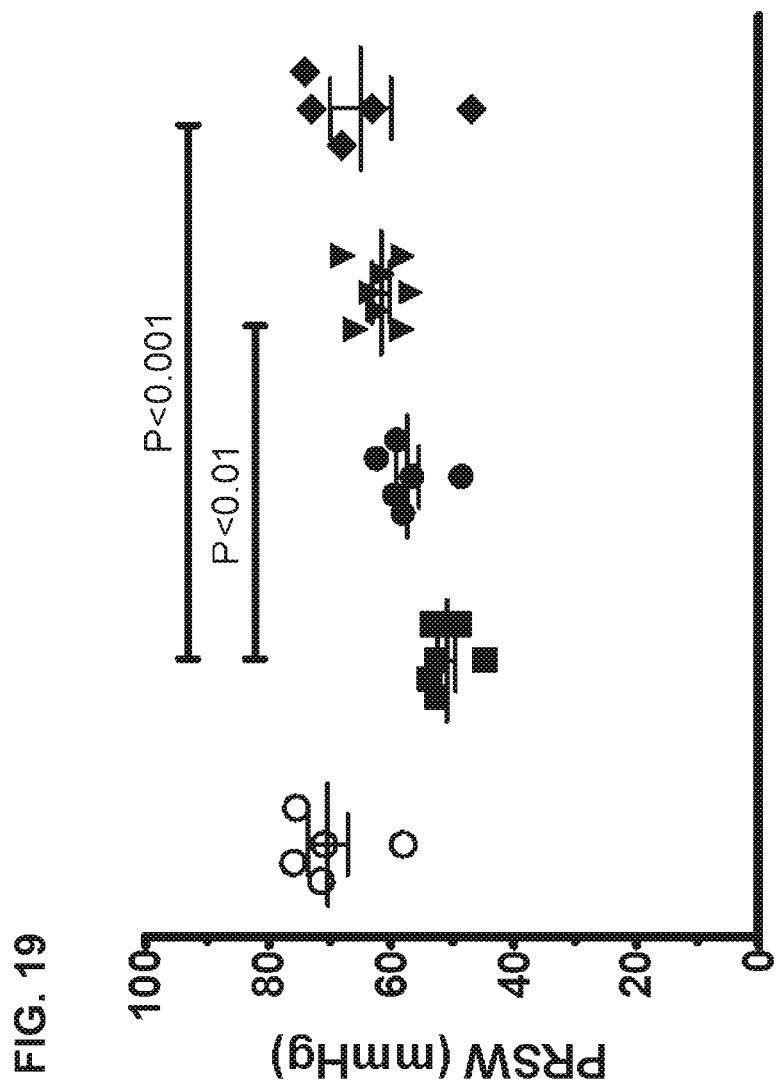

FIG. 19: Effects of human VEGF-A modified RNA and recombinant human VEGF-A on preload recruitable stroke work (PRSW) in mini pigs subjected to myocardial infarction. Mini pigs were subjected to a permanent occlusion of the left anterior descending coronary artery to induce myocardial infarction. A separate group of pigs were subjected to a sham procedure without coronary occlusion (open circles, n=5). Seven days later, infarcted pigs were randomised to a blinded epicardial injection of citrate/saline vehicle (2 mL, filled squares), 1 mg (filled circles) or 10 mg (filled triangles) VEGF-A modified RNA or recombinant human VEGF-A protein (200 ng) formulated in self-assembling nanofibers (filled diamonds). The dose/volume was administered as 20 separate injections (100 μL each) at the peri-infarct area. Left ventricular function was measured invasively 2 months after the injection. Shown are individual data and means±SEM.

Figure 20A:
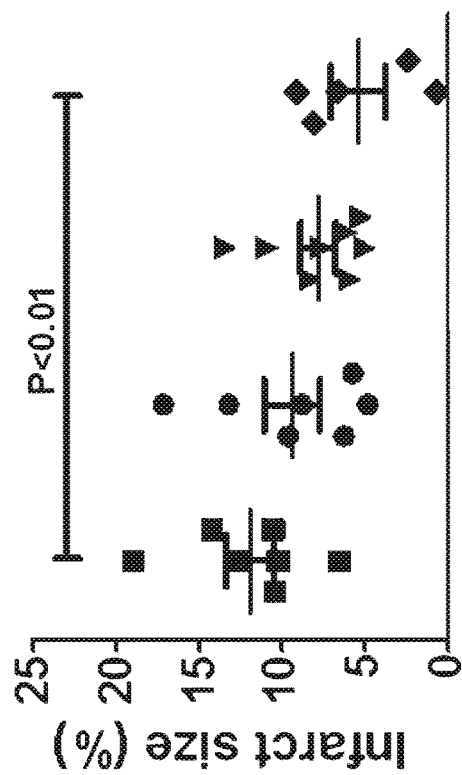
Figure 20B:
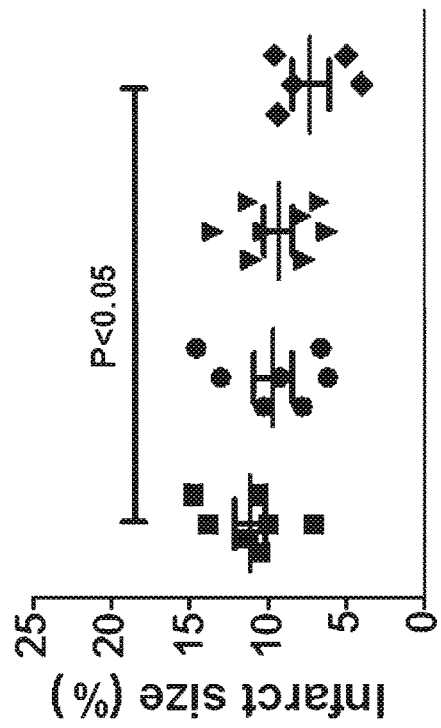
Figure 20C:
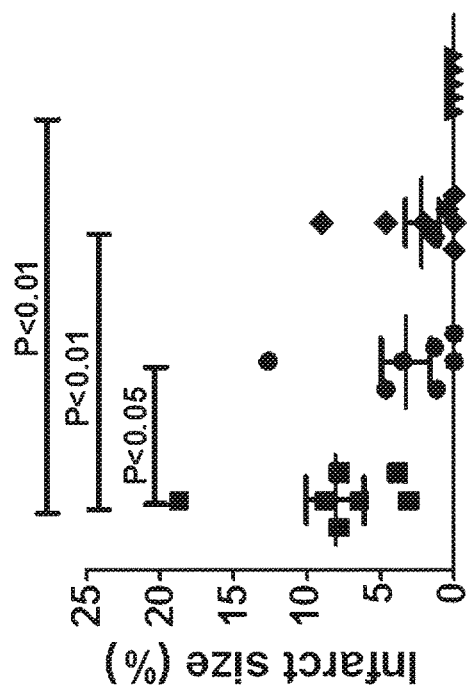

FIGS. 20A, 20B and 20C: Effects of human VEGF-A modified RNA and recombinant human VEGF-A on infarct size in mini pigs subjected to myocardial infarction. Infarct size presented as global left ventricular infarct size (slices 2, 3, 4 and 5, FIG. 20A), mid left ventricular infarct size (slices 3 and 4, FIG. 20B) and mid-most left ventricular infarct size (slice 4, panel FIG. 20C) in mini pigs epicardially injected with citrate/saline (filled squares) or 1 mg (filled circles) or 10 mg (filled triangles) VEGF-A modified RNA or recombinant human VEGF-A protein (200 ng) formulated in self-assembling nanofibers (filled diamonds). The injection was given 7 days after the induction of myocardial infarction through a permanent occlusion of the left anterior descending coronary artery. Infarct size was measured 2 months after the injection. Shown are means±SEM.

Figure 21:
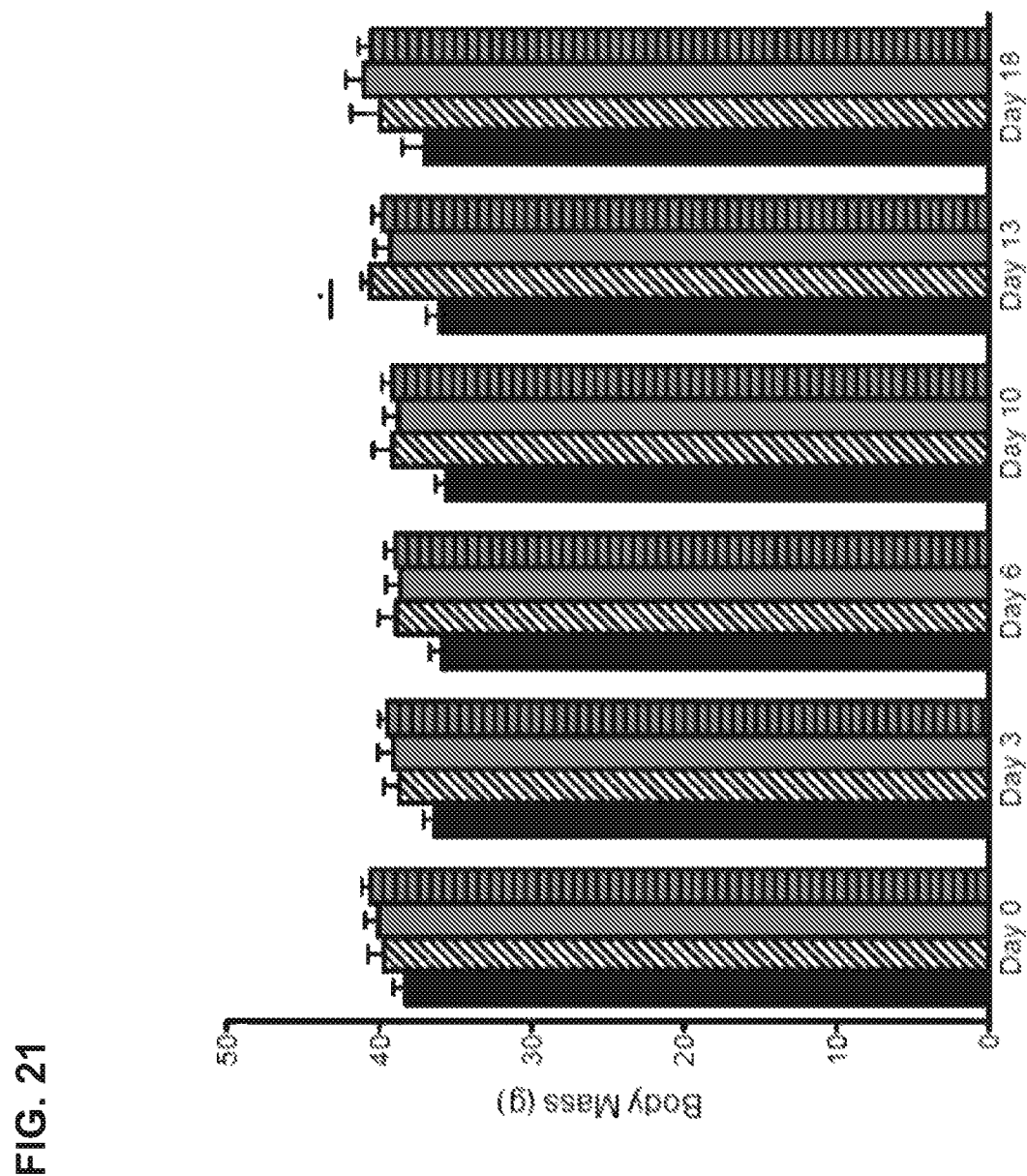

FIG. 21: Body masses of mice during Trial 1 in Example 14. The body mass of each mouse was recorded at each imaging time point. Data presented are means±SEM, black bar; vehicle single injected, hatched bar; vehicle double injected, grey bar; VEGF-A modified RNA single injected, lined bar; VEGF-A modified RNA double injected, *; $p<0.05$ for double vs single injected vehicle.

Figure 22:
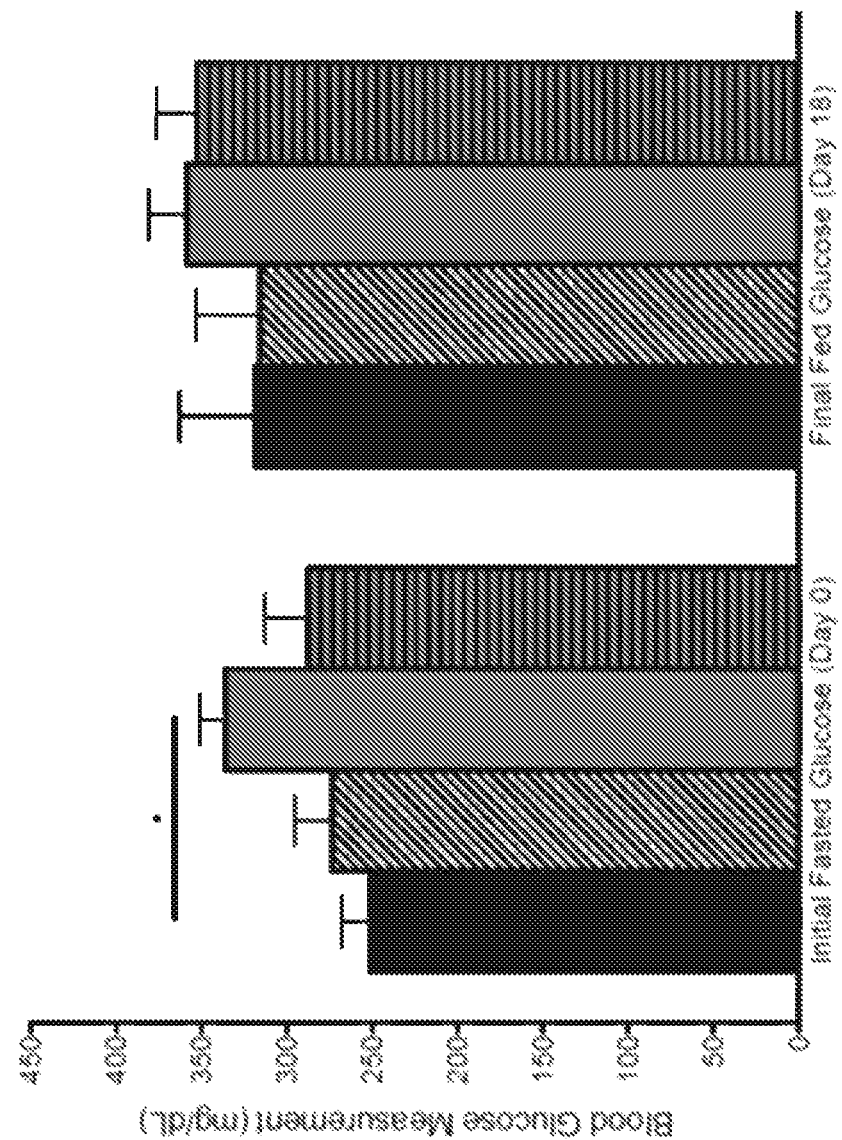

FIG. 22: Fasted and fed blood glucose measurements of mice in Trial 1 in Example 14. At Day 0, blood glucose was measured after a four hour fasting period. At Day 18, fed blood glucose was measured. Data presented are means±SEM, black bar; vehicle single injected, hatched bar; vehicle double injected, grey bar; VEGF-A modified RNA single injected, lined bar; VEGF-A modified RNA double injected, *; $p<0.05$ for VEGF-A modified RNA single injected vs vehicle single injected.

Figure 23:
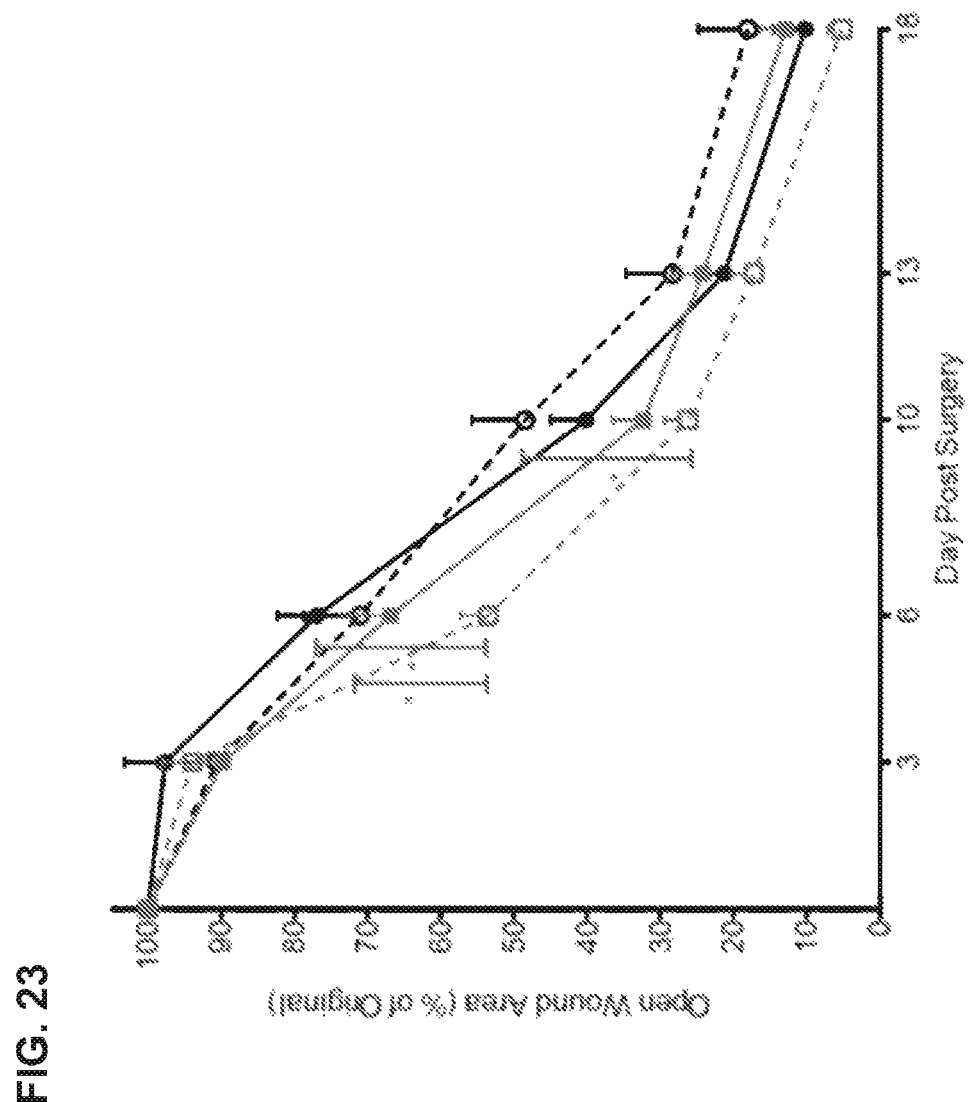

FIG. 23: Wound healing curve for Trial 1 in Example 14. The average normalized open wound area of the median values from three observers are plotted against days post surgery. Data presented are means±SEM, *$p<0.05$ for VEGF-A modified RNA double injection (open square) vs vehicle single (filled circle) and double (open circle) injected respectively at day 6 and VEGF-A modified RNA double injection vs. vehicle double injection at day 10, respectively. Filled square; VEGF-A modified RNA single injected.

Figure 24:
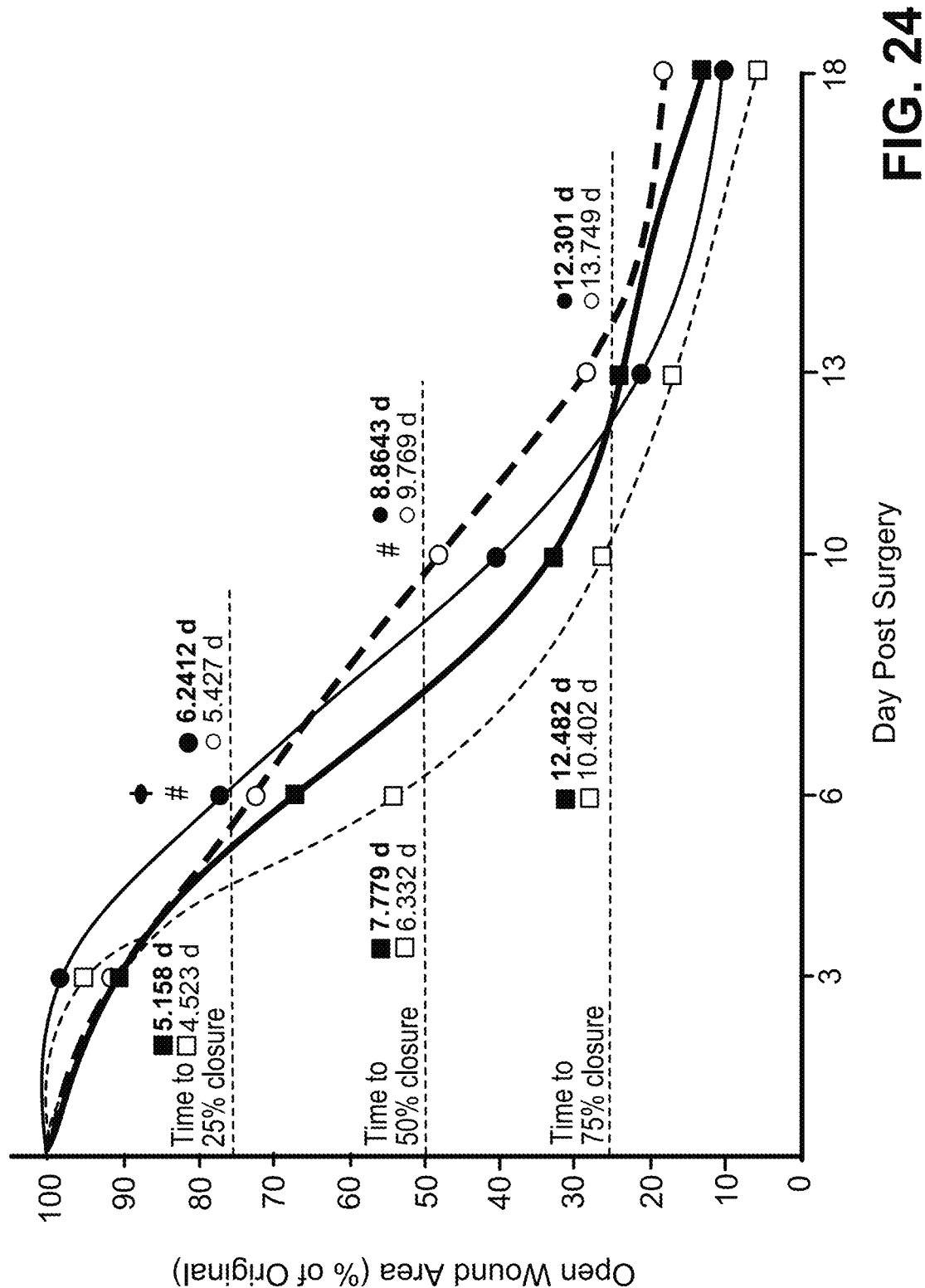

FIG. 24: Cubic spline interpolation of wound healing curve from Trial 1 in Example 14. A cubic spline interpolation was constructed to approximate time to 25%, 50%, and 75% closure as evidenced by the horizontal dashed gray lines. Data presented are means of normalized open wound areas of the median values from three observers. φ; $p<0.05$ for VEGF-A modified RNA double injection (open square) vs vehicle single injection (filled circle) #; $p<0.05$ for VEGF-A modified RNA double injection vs vehicle double injection (open circle). Filled square; VEGF-A modified RNA single injected.

Figure 25:
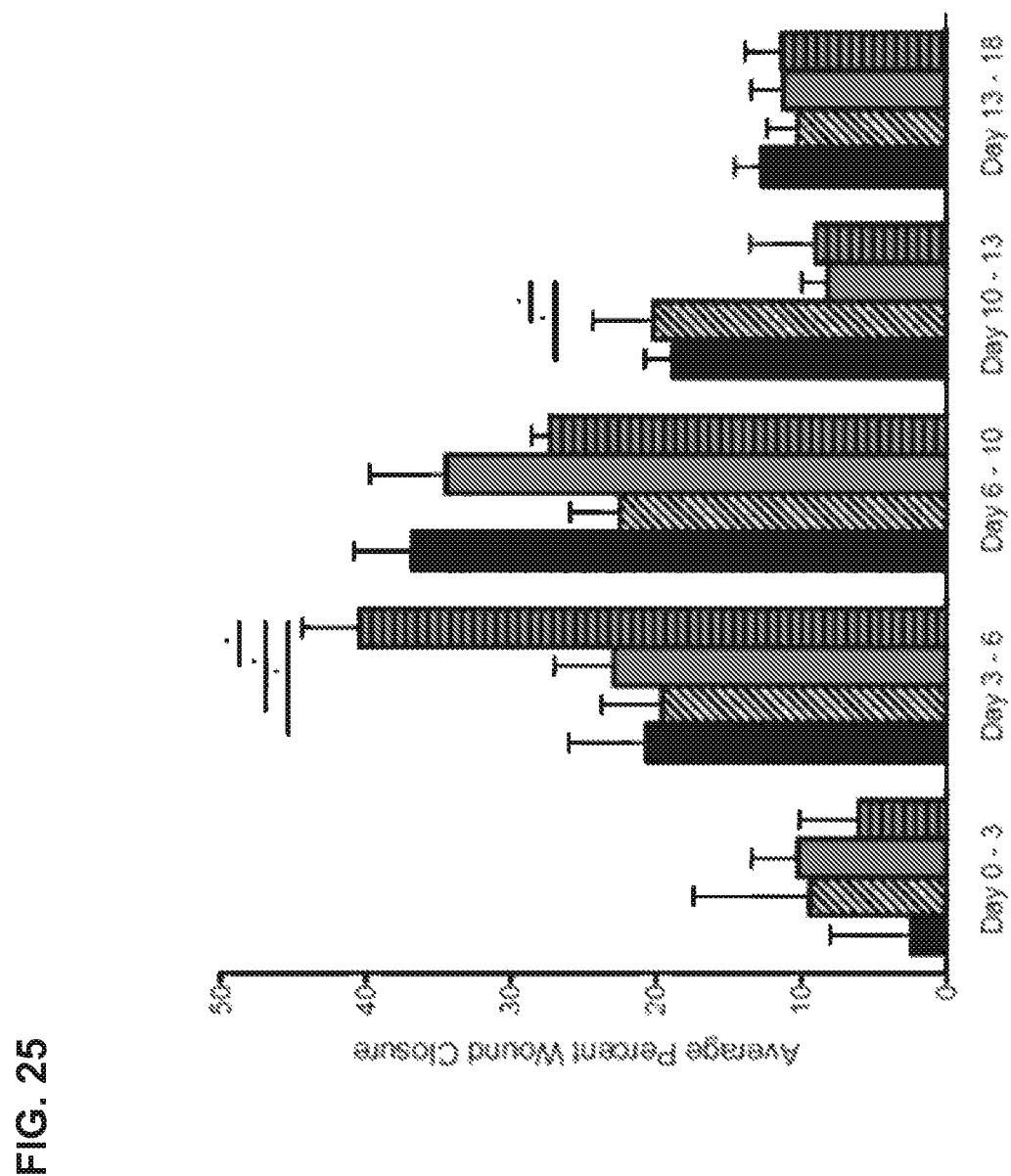

FIG. 25: Percent wound healing between time points in Trial 1 in Example 14. The average percent of wound closure was calculated between each time point using normalized wound area data. Data presented are means±SEM; *$p<0.05$ for higher average percent wound closure for VEGF-A modified RNA double injection (lined bar) vs vehicle double (hatched bar) and single injection (black bar) respectively for day 3 to 6 and for lower average wound closure for VEGF-A modified RNA single injection (grey bar) vs. vehicle double and single injection for day 10 to 13, respectively.

Figure 26:
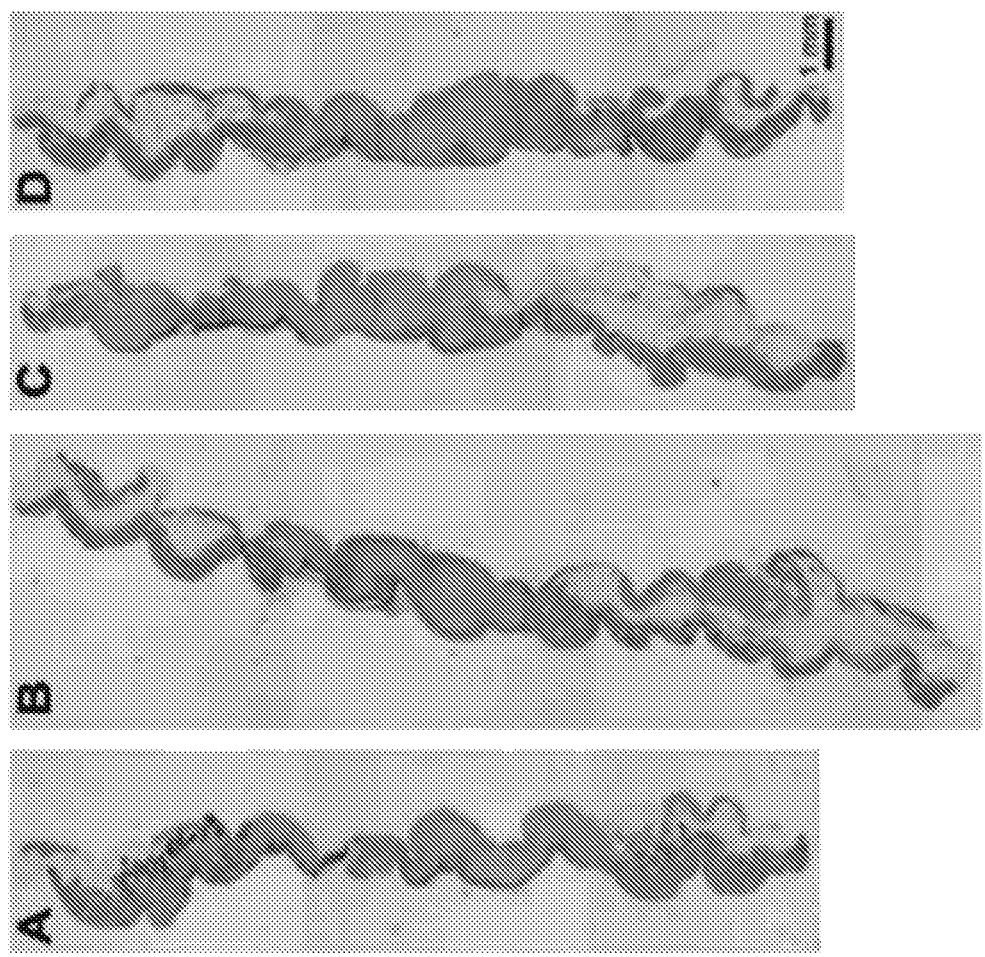

FIG. 26: Representative images of hematoxylin- and eosin-stained sections of wounds in Trial 1 in Example 14. A; vehicle single injected, B; vehicle double injected, C; VEGF-A modified RNA single injected, D; VEGF-A modified RNA double injected.

Figure 27:
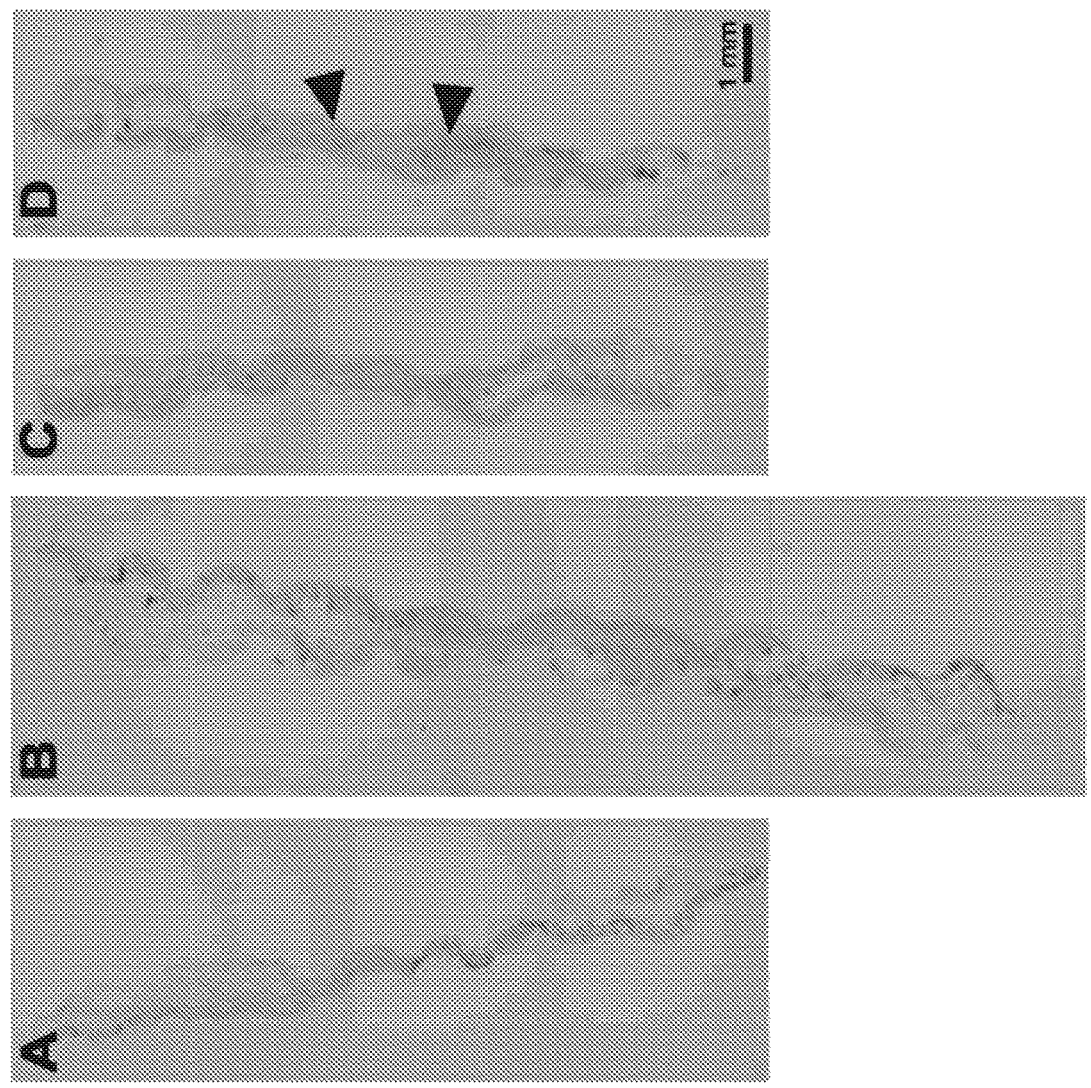

FIG. 27: Representative images of CD31 stained sections of wounds in Trial 1 in Example 14. Arrowheads indicate areas of strong CD31 staining. A) Single vehicle, B) Double vehicle, C) Single VEGF-A modified RNA, D) Double VEGF-A modified RNA.

Figure 28:
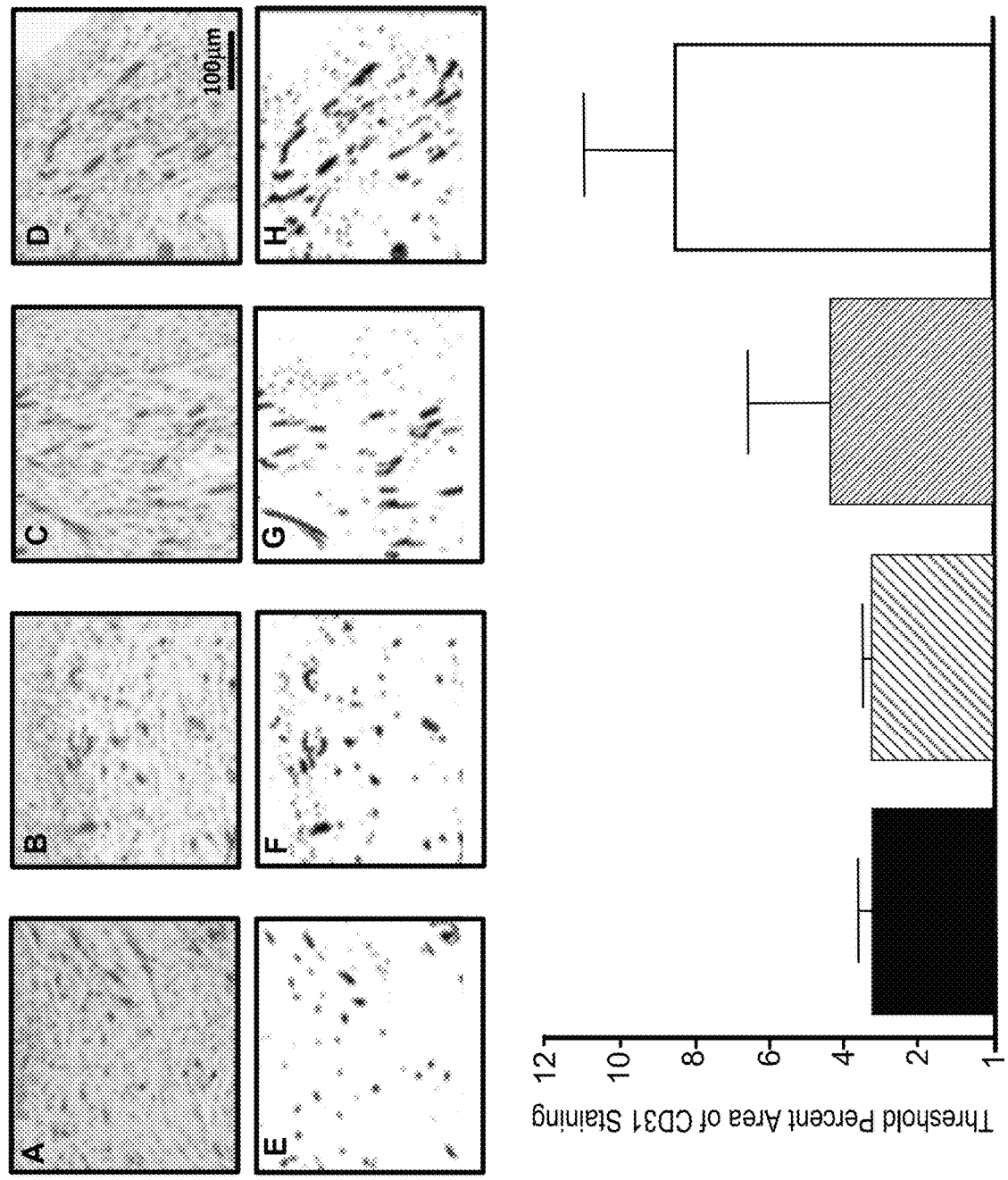

FIG. 28: Quantification of CD31 staining in Trial 1 in Example 14. Panels A to D are representative acquired images and Panels E to H are representative thresholded images of CD31 positive staining (brown channel). A and E; Single vehicle, B and F; Double vehicle, C and G; single VEGF-A modified RNA, D and H; double VEGF-A modified RNA, I; Quantification of percent area of CD31 staining (area covered by black pixels). Black bar; vehicle single injected, hatched bar; vehicle double injected, grey bar; VEGF-A modified RNA single injected, lined bar; VEGF-A modified RNA double injected.

Figure 29:
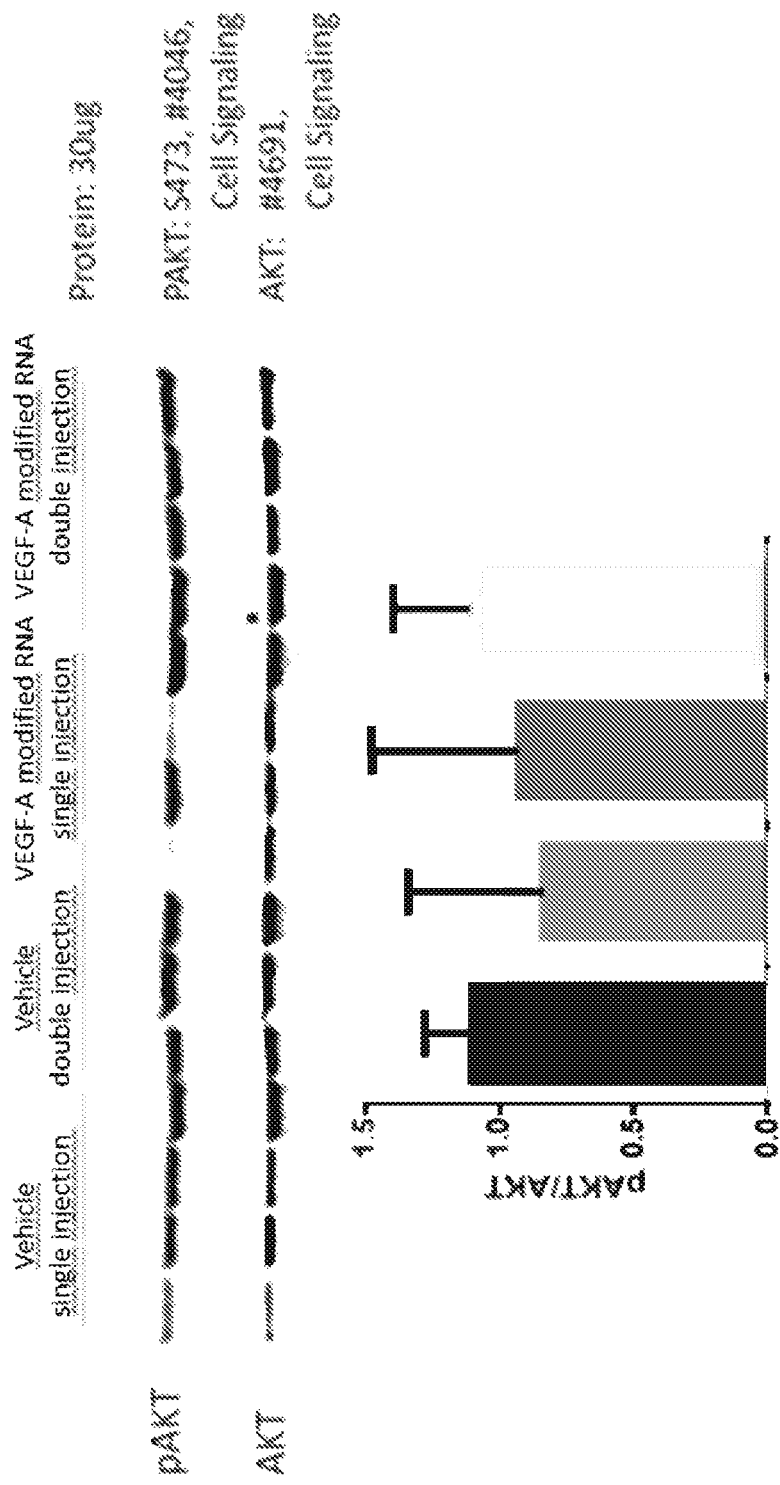

FIG. 29: Downstream VEGF signalling analysis with Western blot (Trial 1) in Example 14. Top panel; pAKT and AKT blots of Day 18 samples from mice receiving a single dose of vehicle on Day 0, double dose of vehicle on Days 0 and 3, single dose of VEGF-A modified RNA on Day 0, and double dose of VEGF-A modified RNA on Days 0 and 3.

Bottom panel; Quantified ratio of pAKT/AKT shows no statistical difference between treatment groups. Left bar; single vehicle injection, left middle bar; double vehicle injection, right middle bar; single VEGF-A modified RNA injection, right bar; double VEGF-A modified RNA injection.

FIG. 30: Western blot analysis of pVEGFR2, VEGFR2 and VEGF-A in harvested mouse wounds at Day 18 from Trial 1 in Example 14. Top panel; pVEGFR2, VEGFR2, and VEGFA blots of Day 18 samples from mice receiving a single dose of vehicle on Day 0, double dose of vehicle on Days 0 and 3, single dose of VEGF-A modified RNA on Day 0, and double dose of VEGF-A modified RNA on Days 0 and 3. Bottom panel; Quantified ratio of pVEGFR2/VEGFR2 show no statistical difference between treatment groups. Left bar; single vehicle injection, left middle bar; double vehicle injection, right middle bar; single VEGF-A modified RNA injection, right bar; double VEGF-A modified RNA injection.

Figure 31:
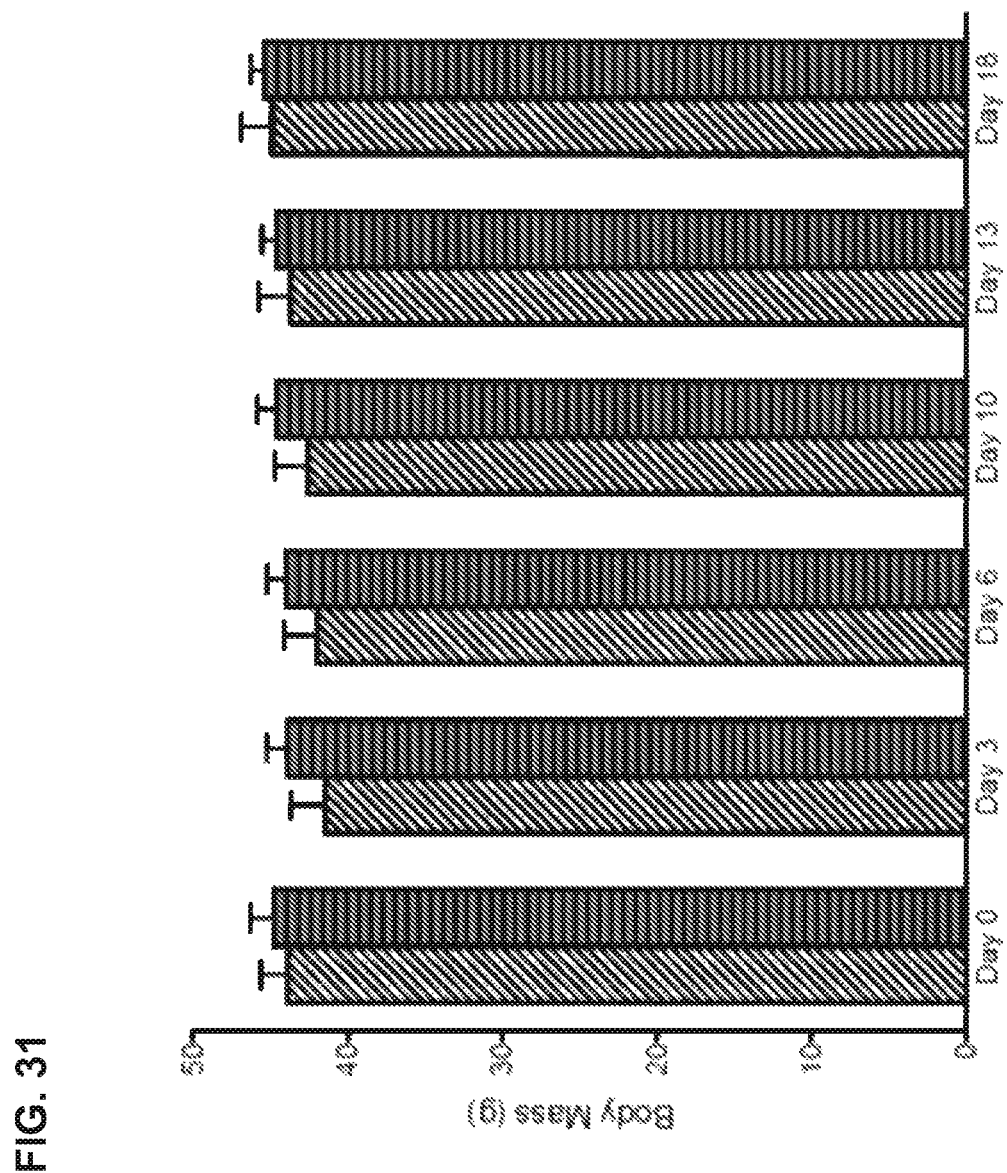

FIG. 31: Body masses of mice during Trial 2 in Example 14. The body mass of each mouse was recorded at each imaging time point. Data presented are means±SEM. Left bar; vehicle double injected, right bar: VEGF-A modified RNA double injected.

Figure 32:
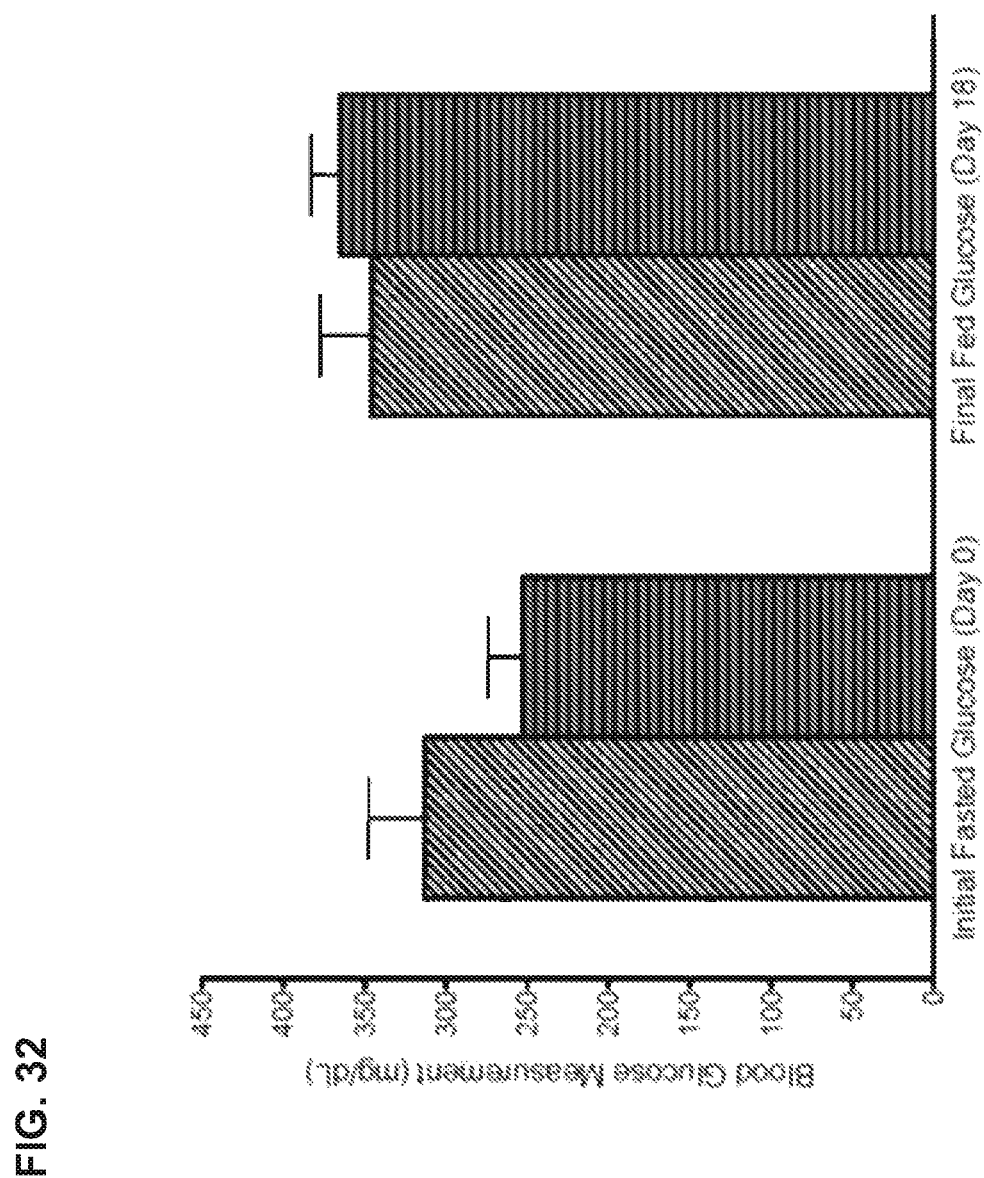

FIG. 32: Fasted and fed blood glucose in mice in Trial 2 in Example 14. At Day 0, blood glucose was measured after a four-hour fasting period. At Day 18, fed blood glucose was measured. Data presented are means±SEM. Left bar; vehicle double injected, right bar: VEGF-A modified RNA double injected.

Figure 33:
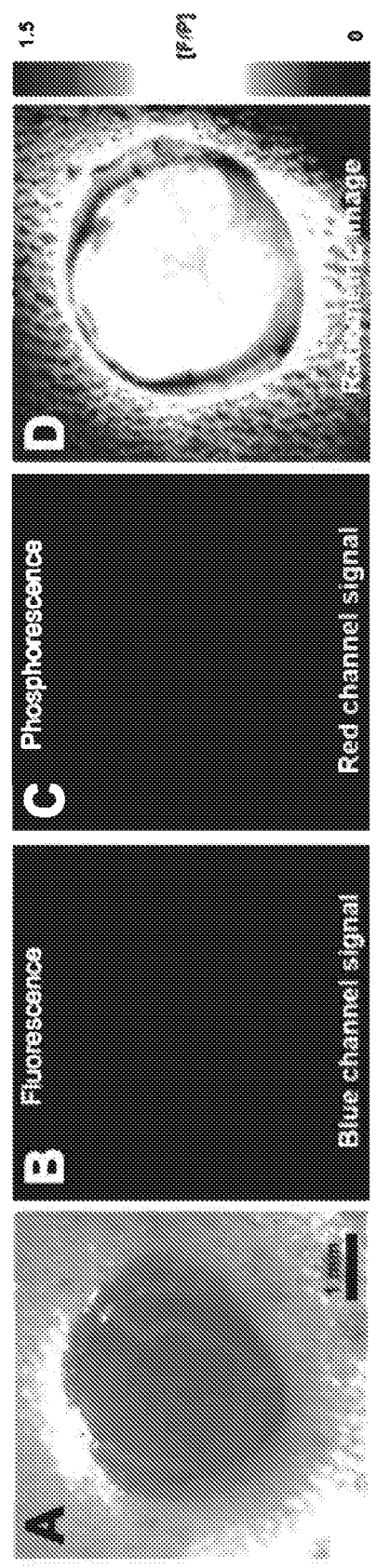

FIG. 33: Schematic of in vivo application of oxygen-sensitive nanoparticles. A) Application of nanoparticles within the full thickness skin wound. Upon excitation, the nanoparticles emit strong room temperature fluorescence (B) and strong oxygen-dependent phosphorescence (C). A ratiometric image is constructed of the ratio between fluorescence and phosphorescence to report the relative level of oxygen within the wound bed (D).

Figure 34:
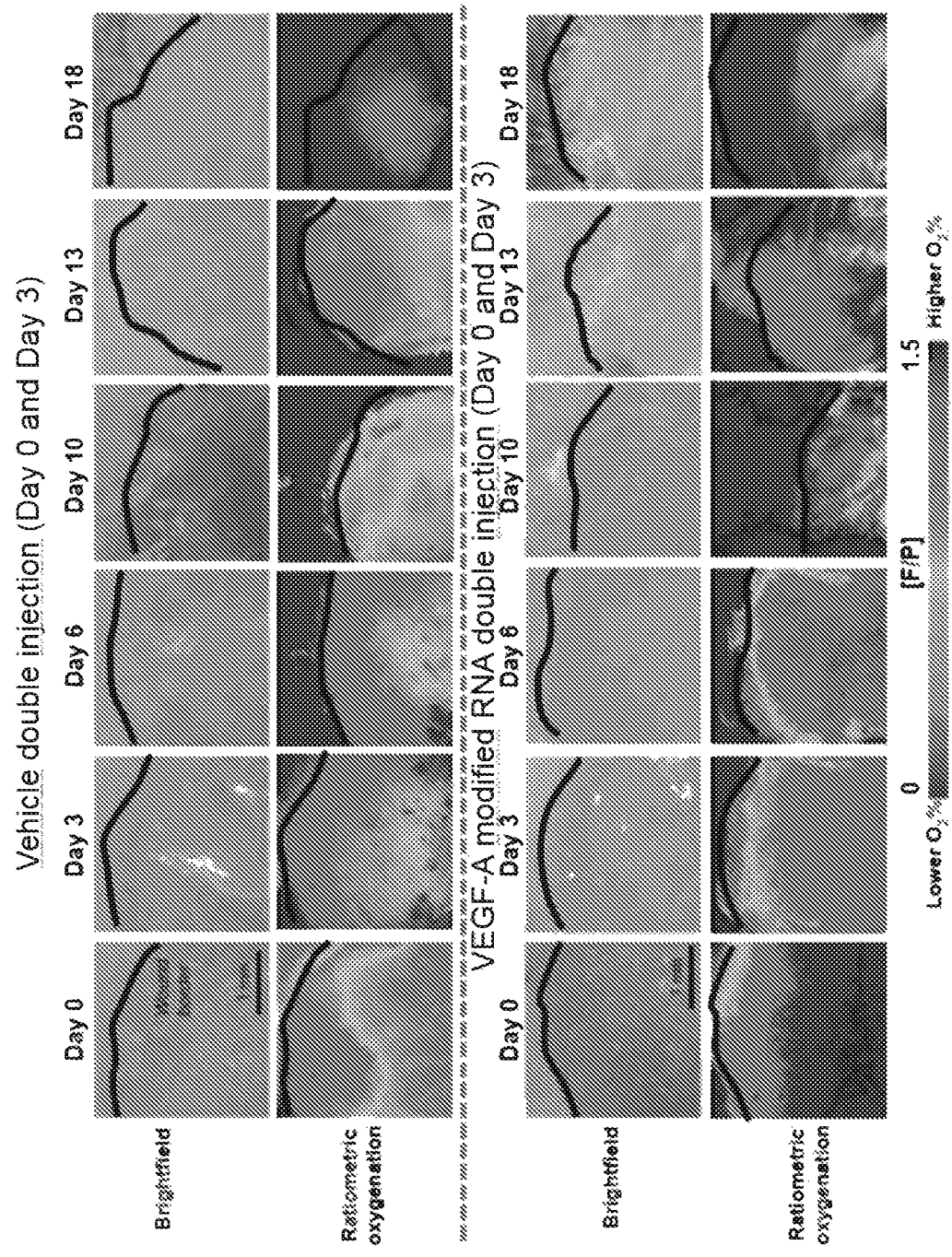

FIG. 34: Ratiometric images of relative oxygenation levels within wound beds in Trial 2 in Example 14. Representative brightfield and ratiometric images for double vehicle (top half) and double VEGF-A modified RNA (bottom half) treated wounds for each time point. The wound border is outlined in black.

Figure 35:
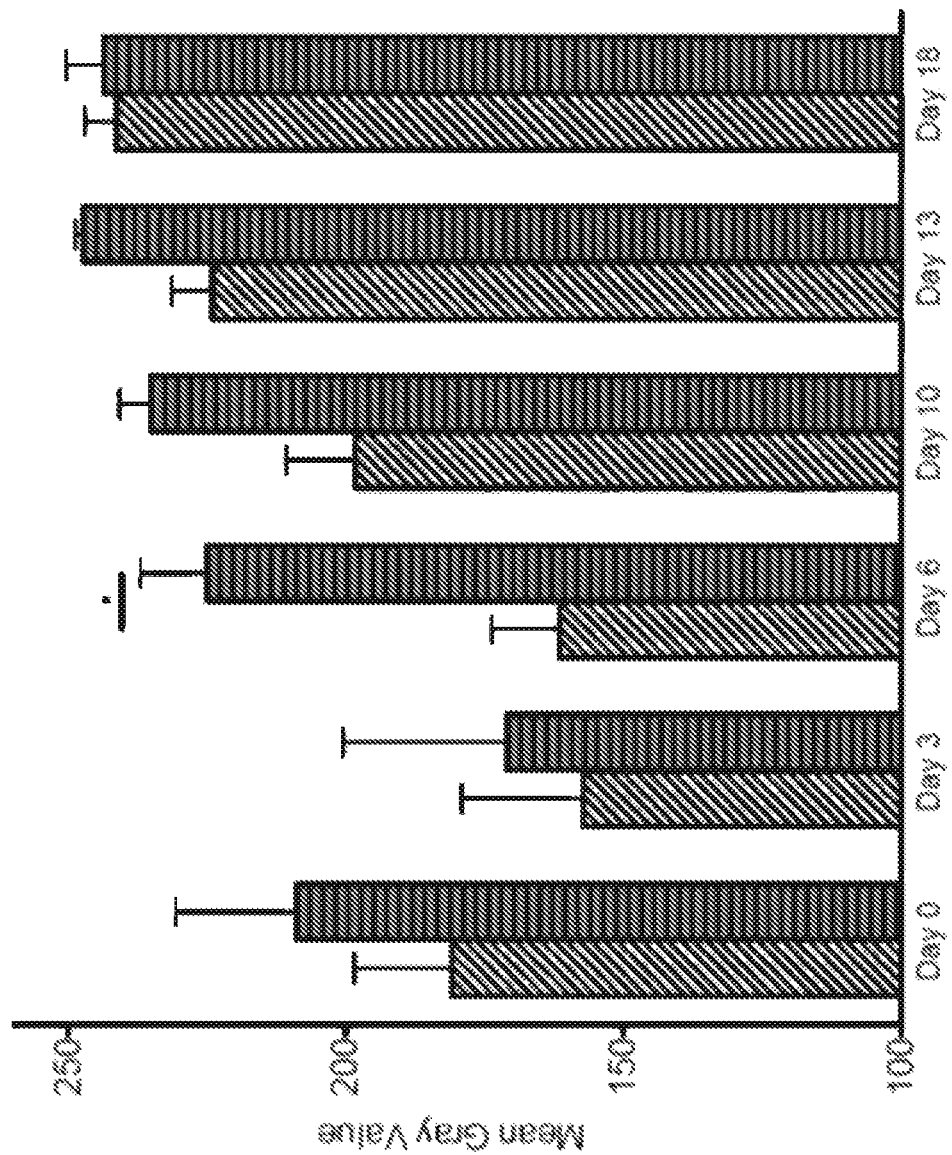

FIG. 35: Quantification of oxygenation via image analysis of fluorescence and phosphorescence from the oxygen-sensitive nanoparticles in the wound bed. The mean gray value of each raw fluorescence to phosphorescence image was calculated for the wound bed. Data presented are means±SEM, *$p<0.05$ for mean Gray value for VEGF-A modified RNA double injection (right bar) vs vehicle double injection (left bar).

Figure 36:
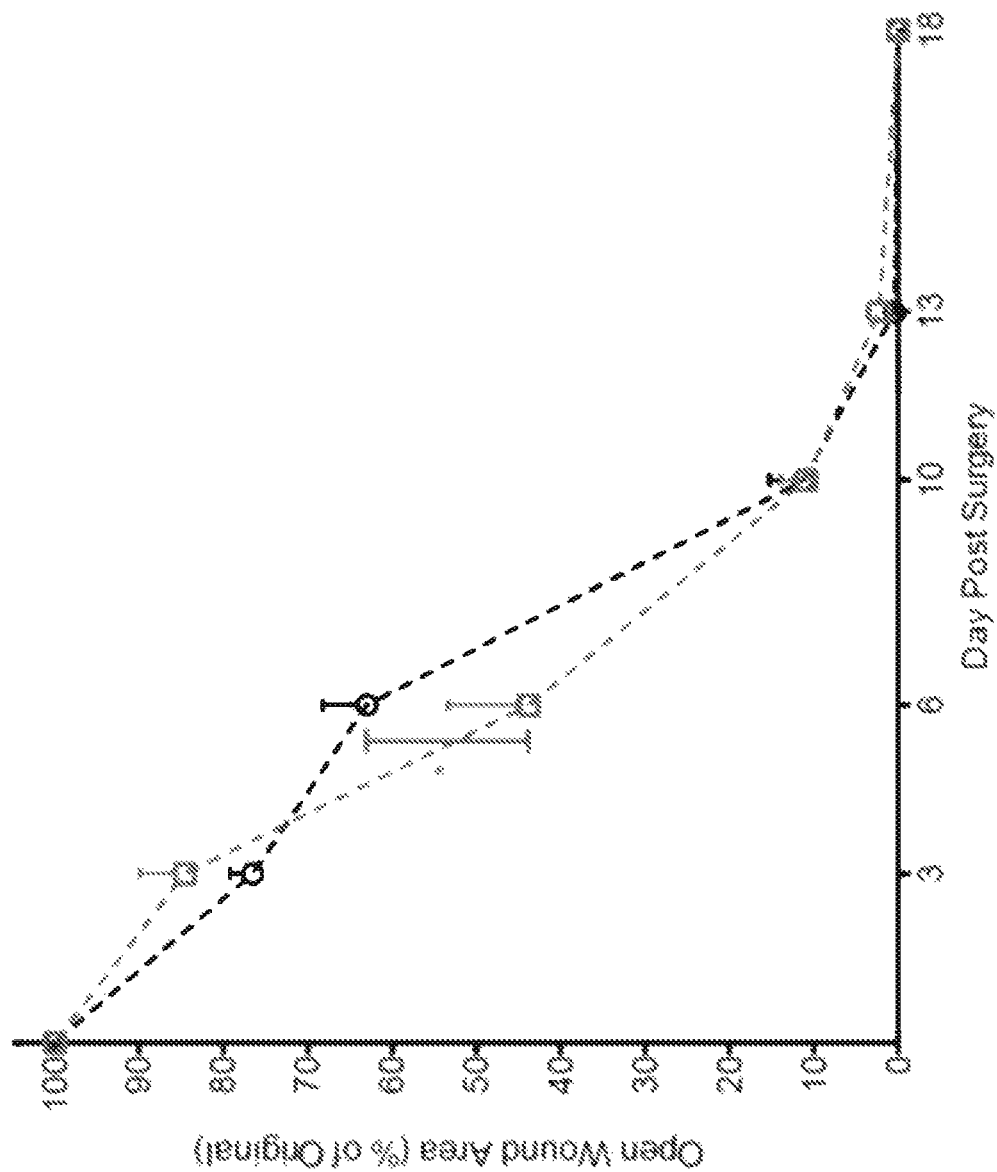

FIG. 36: Wound healing curve for Trial 2 in Example 14. The average normalized open wound area of the median values from three independent observers are plotted against days post surgery. Data presented are means±SEM, *$p<0.05$ for lower open wound area for VEGF-A modified RNA double injection (open square) vs vehicle double injection (open circle), respectively at day 6. Area under the curve was for vehicle double injection 641.31 and for VEGF-A modified RNA double injection 604.35, respectively.

Figure 37:
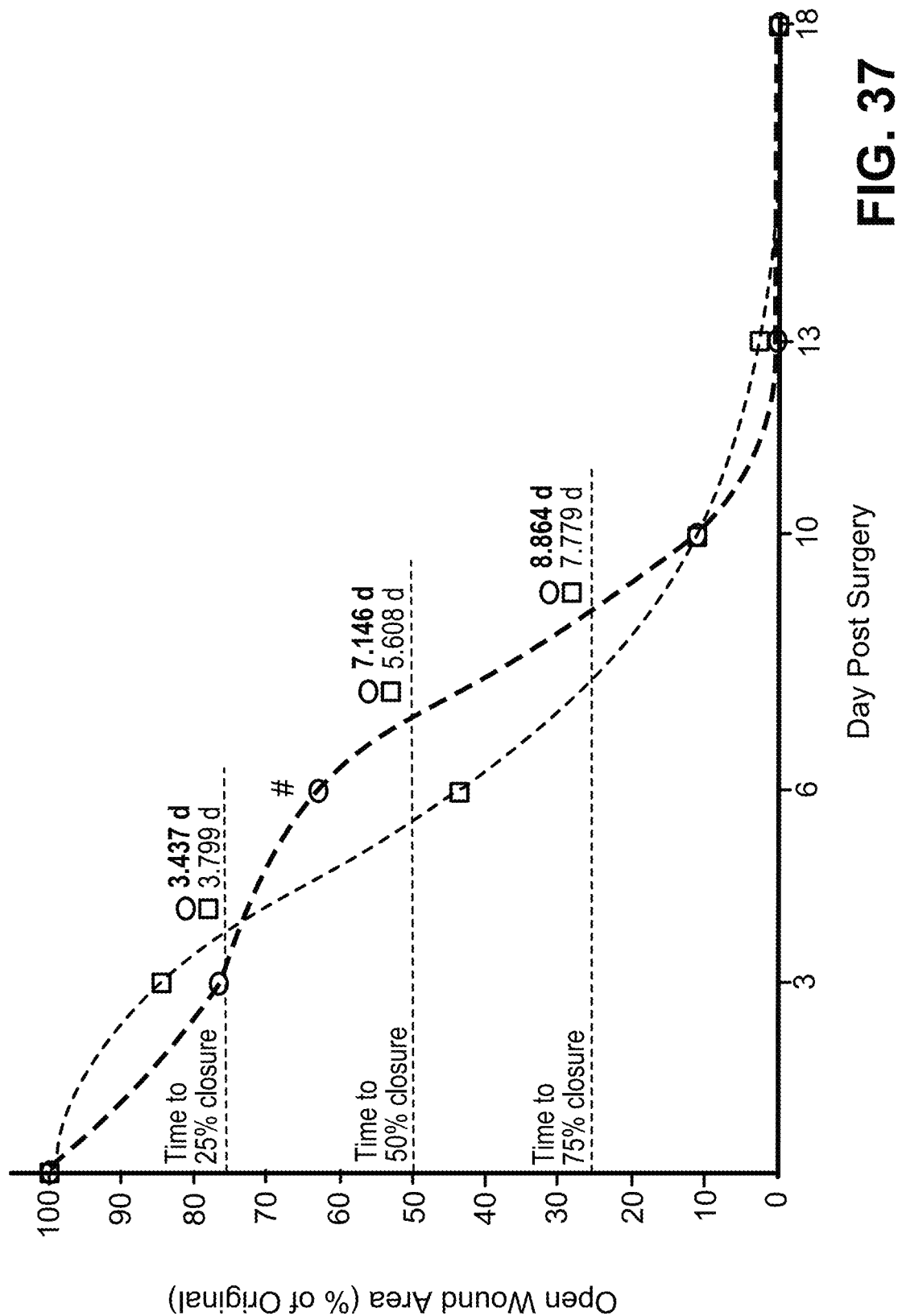

FIG. 37: Cubic spline interpolation of wound healing curve from Trial 2 in Example 14. A cubic spline interpolation was constructed to approximate time to 25%, 50%, and 75% closure as evidenced by the gray dashed line. Data presented are means of normalized open wound areas of the median values from three observers. #; $p<0.05$ for VEGF-A modified RNA double injection (open square) vs double vehicle injection (open circle).

Figure 38:
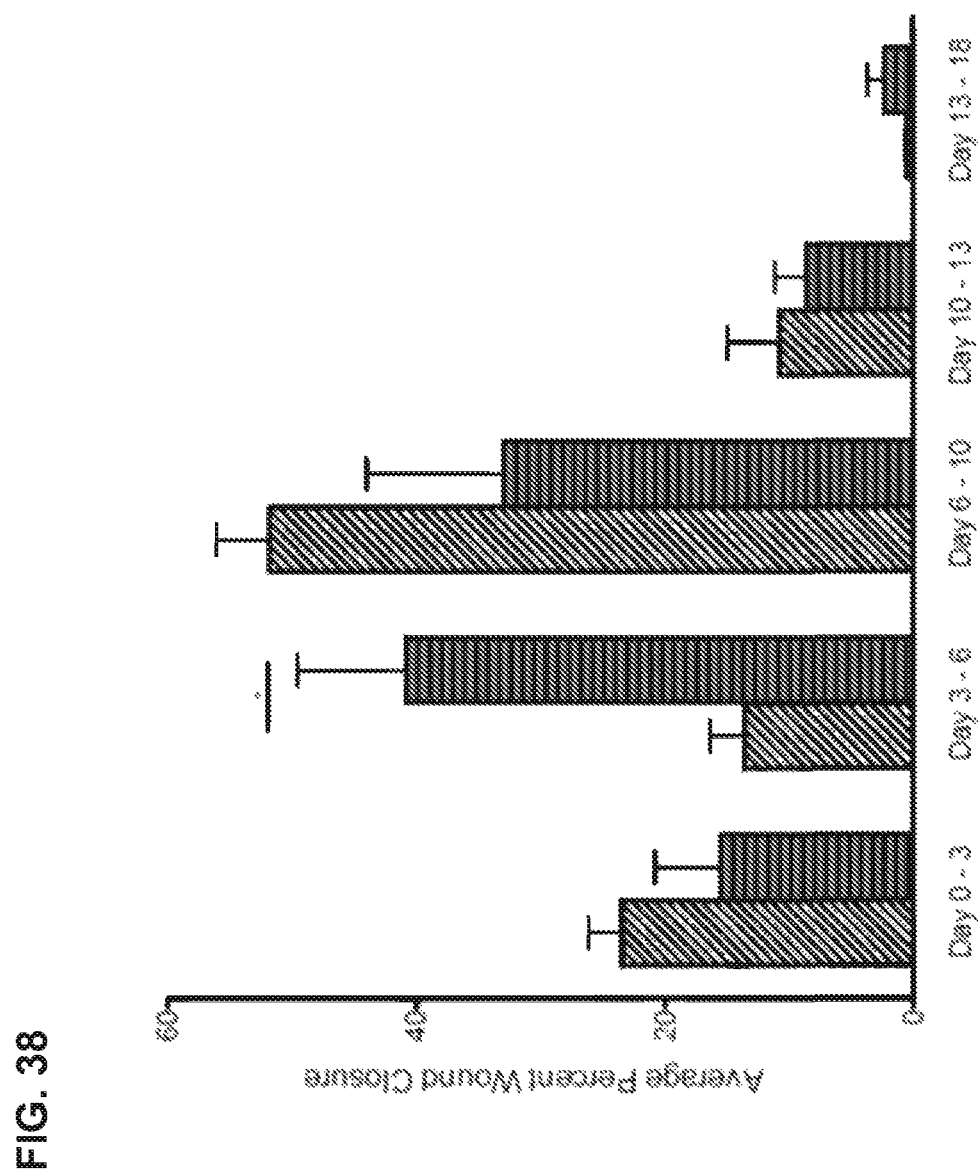

FIG. 38: Percent wound healing between time points in Trial 2 in Example 14. The average percent of wound closure was calculated between each time point using normalized wound area data. Data presented are means±SEM; *$p<0.05$ for higher average percent wound closure for VEGF-A modified RNA double injection (right bar) vs vehicle double injection (left bar) for day 3-6.

Figure 39:
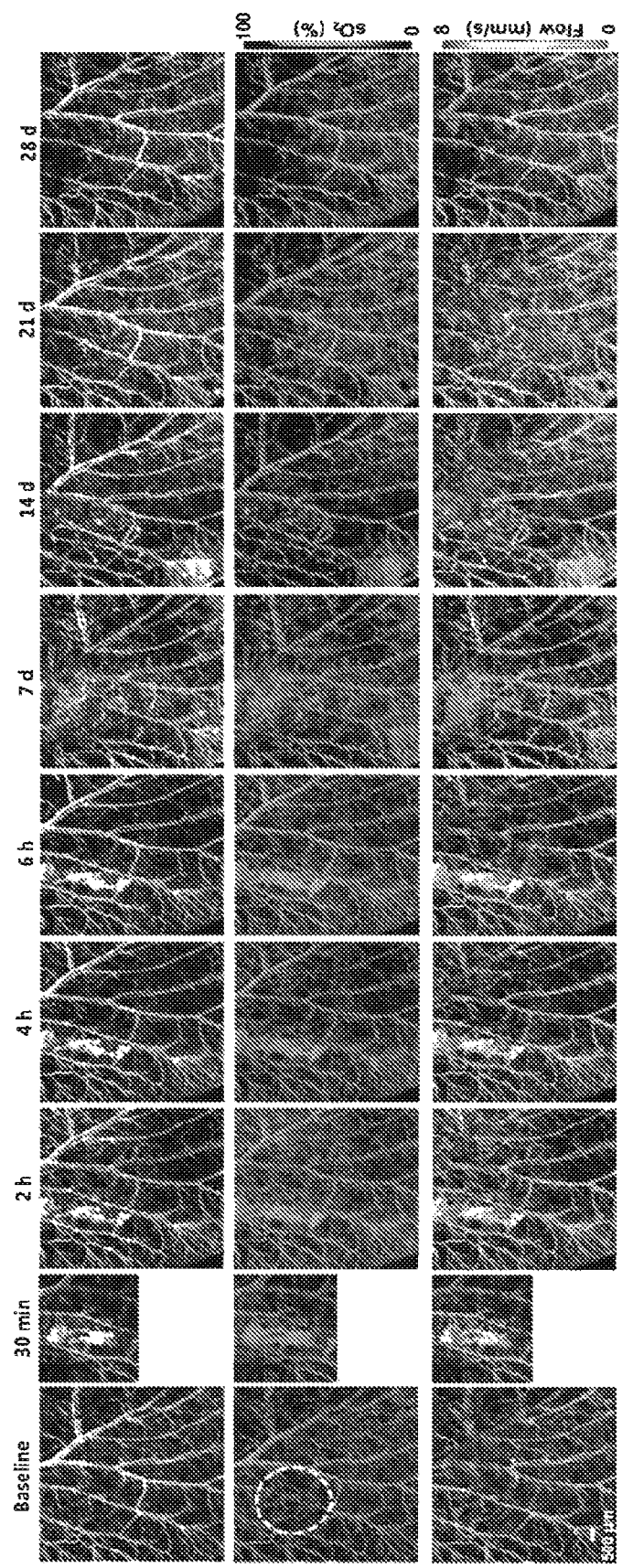

FIG. 39: Photoacoustic microscopy of vascular responses to high-dose VEGF-A modified RNA in the mouse ear. First row; vascular structure; second row; $sO_2$ (%); third row; blood flow speed (mm/s). Dashed circle; injection site. Arrows in row 3; vessels with significantly upregulated blood flow. Labels on top of first row indicate time from intradermal injection of VEGF-A modified RNA (100 μg).

Figure 40:
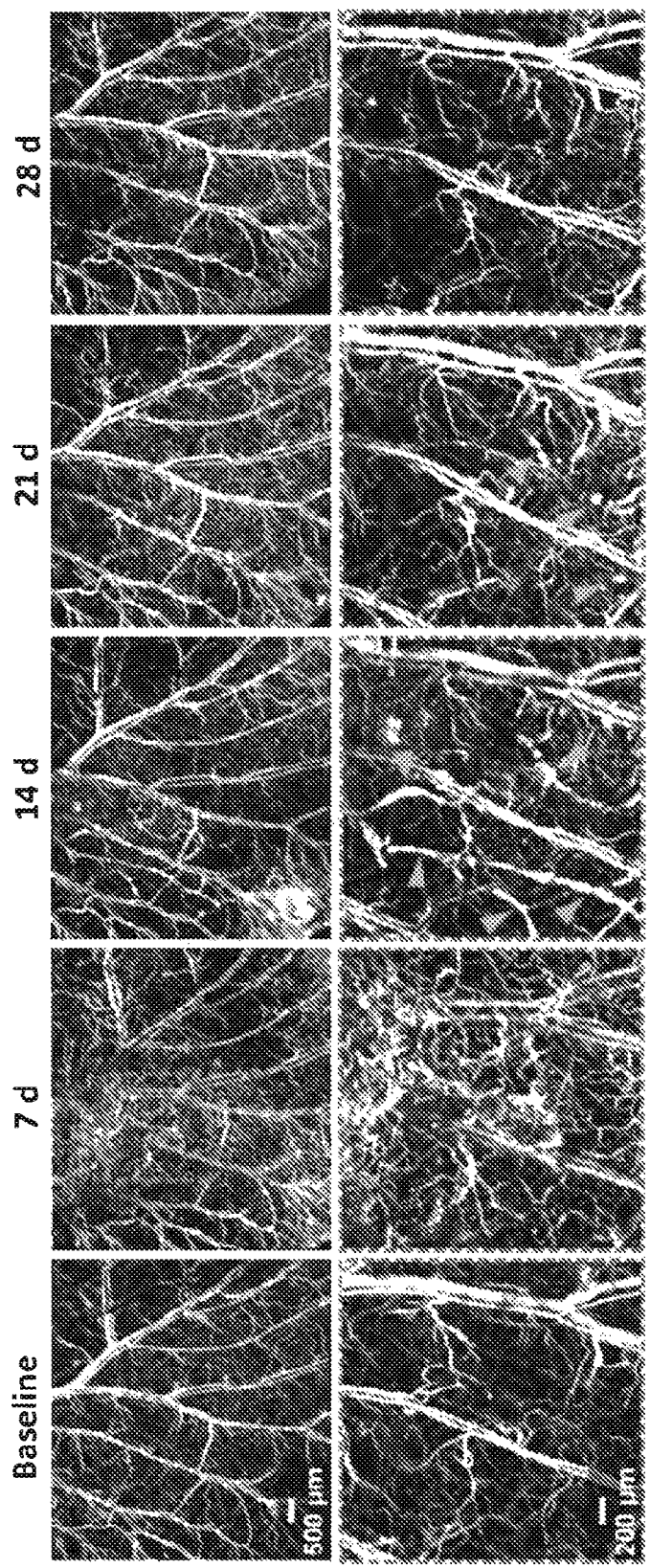

FIG. 40: Neovessel formation and angiogenesis in the mouse ear intradermally injected with a high-dose VEGF-A modified RNA. Zoomed-in images of neovessels (labelled by arrows, second row) and angiogenesis in the ear of mouse intradermally injected with 100 μg VEGF-A modified RNA. Region zoomed in is indicated by dash square in the first row. Labels on top of first row indicate time from intradermal injection of VEGF-A modified RNA (100 μg).

Figure 41:
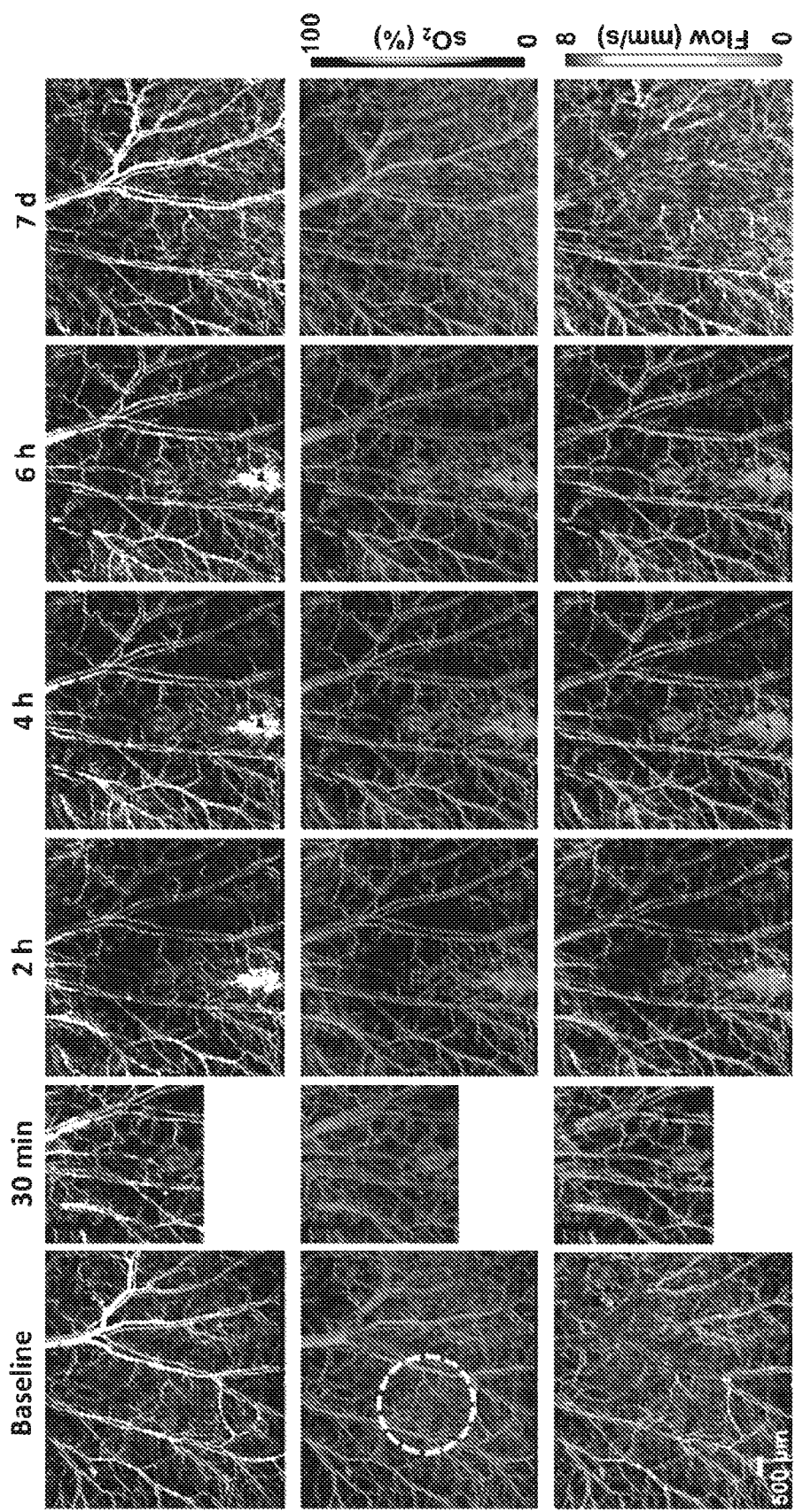

FIG. 41: Photoacoustic microscopy of vascular responses to low-dose VEGF-A modified RNA in the mouse ear. First row; vascular structure; second row; $sO_2$ (%); third row; blood flow speed (mm/s). Dashed circle; injection site. Labels on top of first row indicate time from intradermal injection of VEGF-A modified RNA (10 μg).

Figure 42:
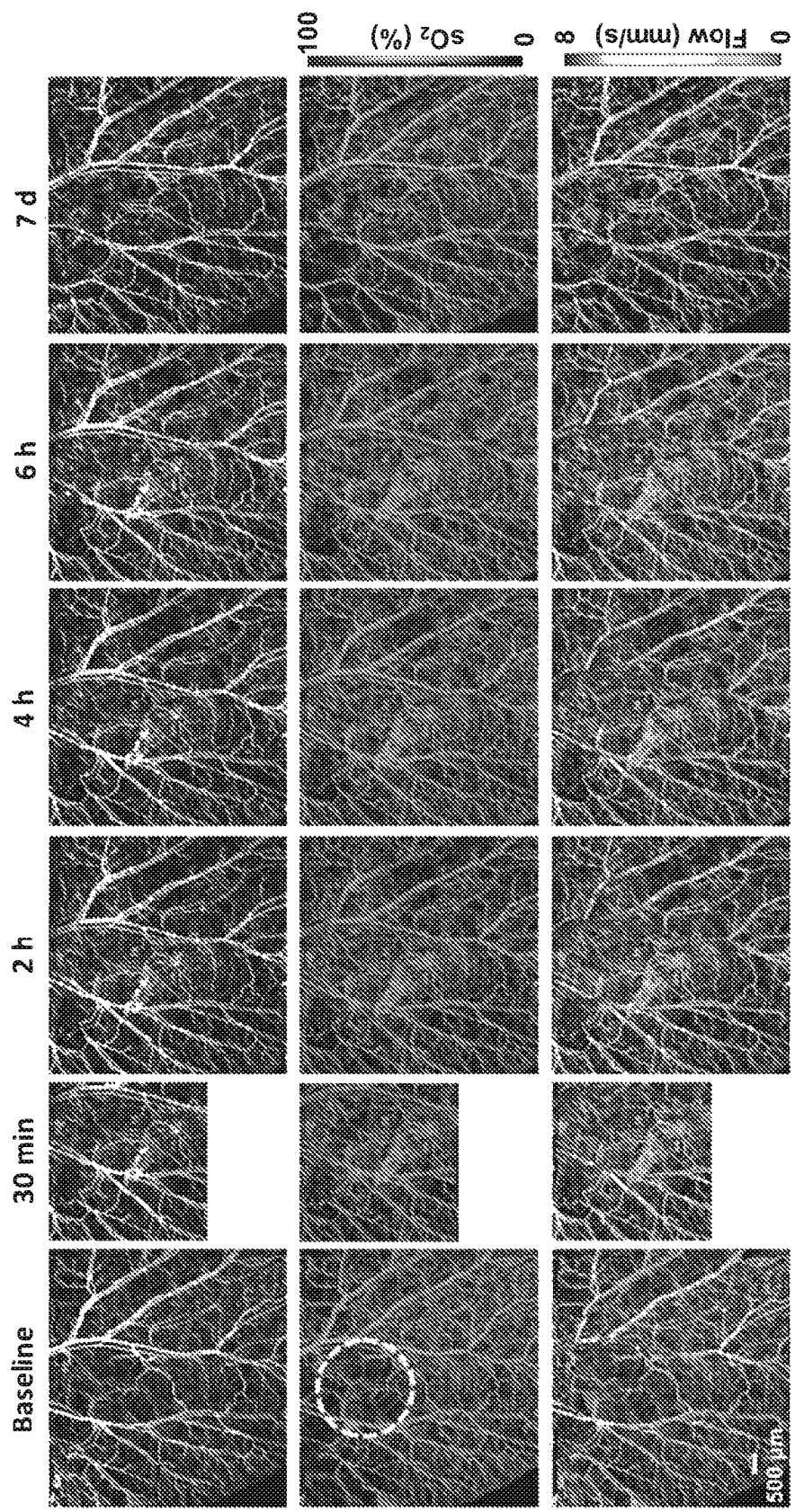

FIG. 42: Photoacoustic microscopy of vascular responses to human recombinant VEGF-A protein in the mouse ear. First row; vascular structure; second row; $sO_2$ (%); third row; blood flow speed (mm/s). Dashed circle; injection site. Labels on top of first row indicate time from intradermal injection of the human recombinant VEGF-A protein (1 μg). Vessels with obvious flow upregulation are indicated with arrows in third row.

Figure 43:
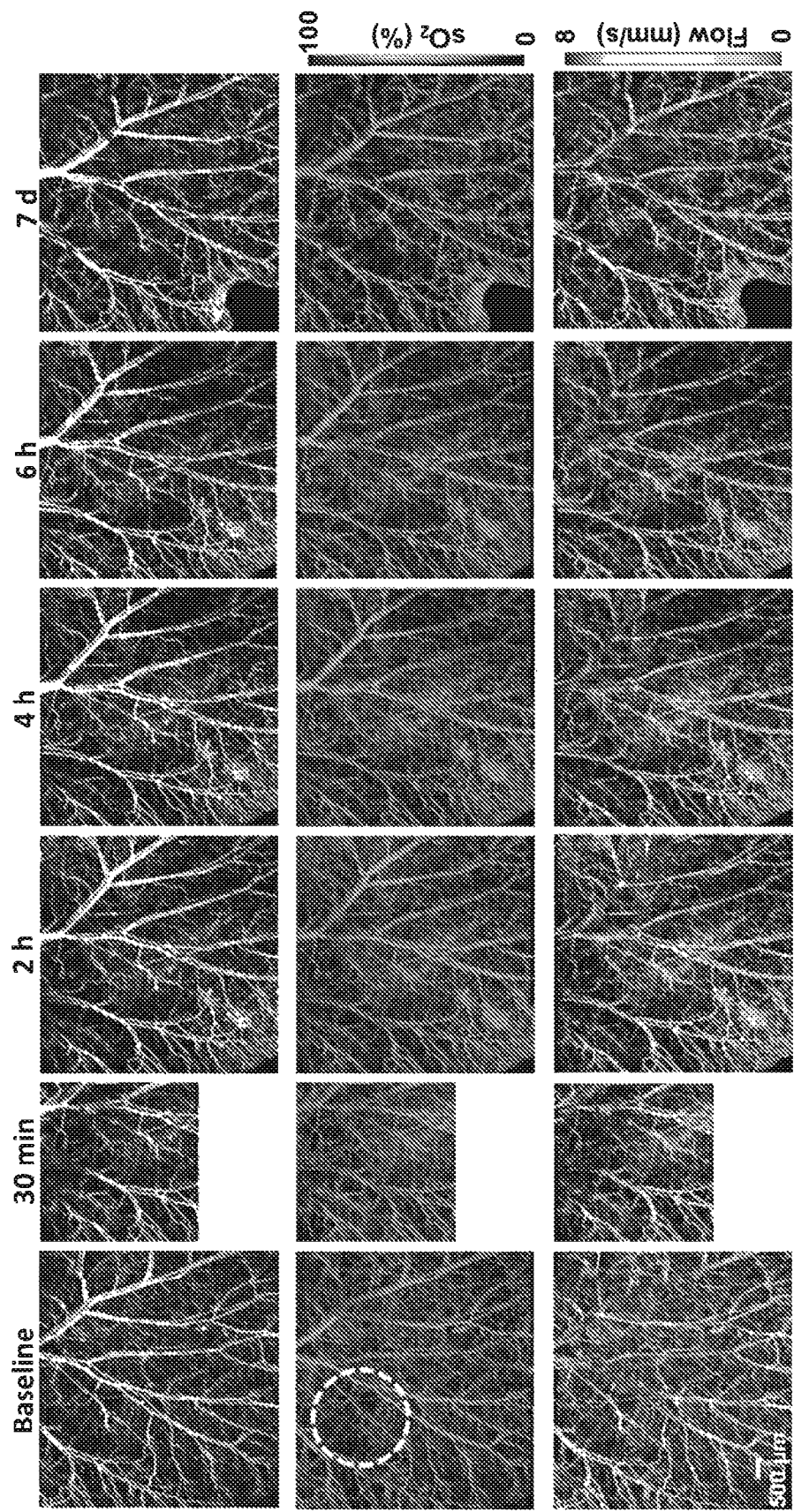

FIG. 43: Photoacoustic microscopy of vascular responses to citrate/saline in the mouse ear. First row; vascular structure; second row; $sO_2$ (%); third row; blood flow speed (mm/s). Dashed circle; injection site. Labels on top of first row indicate time from intradermal injection of citrate/saline (10 μL).

Figure 44:
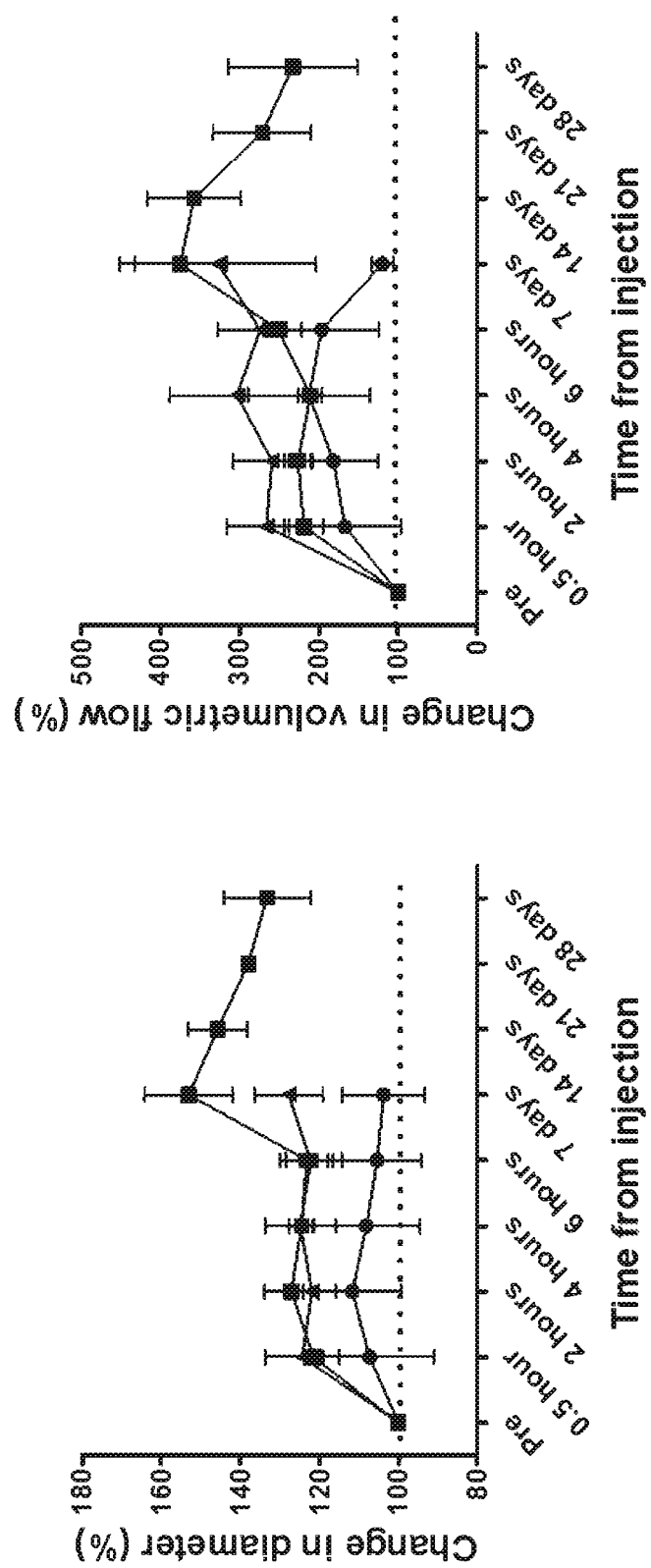

FIG. 44: Effects of VEGF-A modified RNA, human recombinant VEGF-A protein, and citrate/saline on vascular responses in the mouse ear. Quantitative analysis of the acute and long-term vascular responses (vessel diameter, left panel, and volumetric blood flow, right panel) induced by the intradermal injection of VEGF-A modified RNA (100 μg, filled squares), human recombinant VEGF-A protein (1 μg, filled triangles) or citrate/saline (10 μL filled circles) in the mouse ear. Values shown are means±SD, n=3/group.

Figure 45:
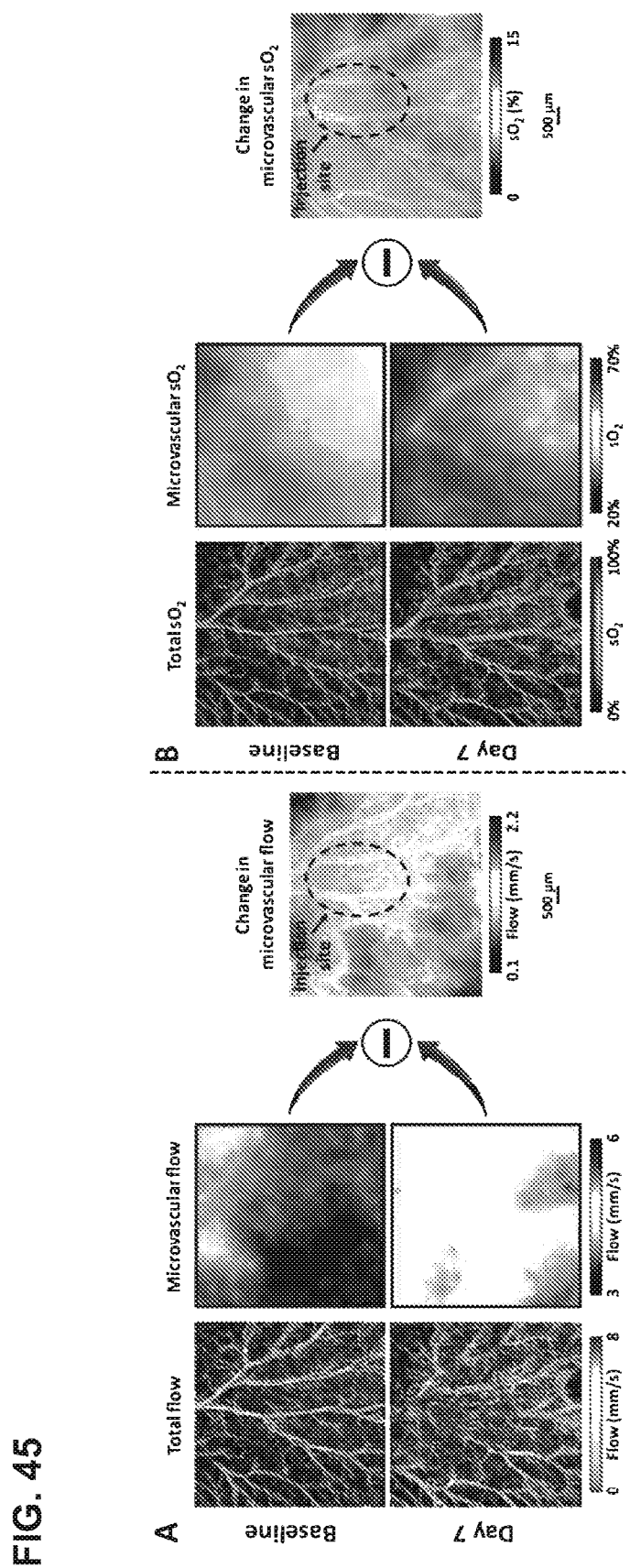

FIG. 45: Influence on microvascular flow and oxygen saturation following injection of VEGF-A modified RNA in the mouse ear. VEGF-A modified RNA (100 μg) was intradermally injected in the mouse ear. Microvascular flow (panel A) and oxygen saturation (panel B) were assessed before injection (baseline) and 7 days later.

Figure 46:
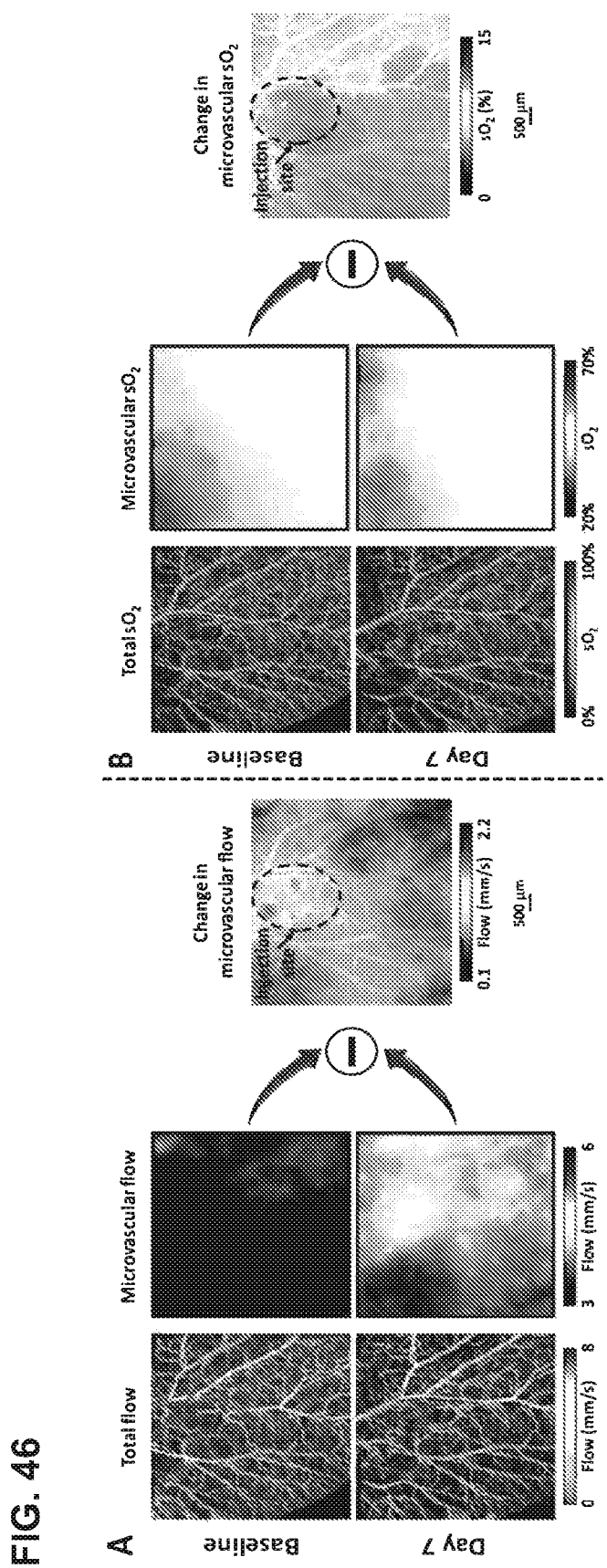

FIG. 46: Influence on microvascular flow and oxygen saturation following injection of recombinant human VEGF-A protein in the mouse ear. Recombinant human VEGF-A protein (1 μg) was intradermally injected in the mouse ear. Microvascular flow (panel A) and oxygen saturation (panel B) were assessed before injection (baseline) and 7 days later.

Figure 47:
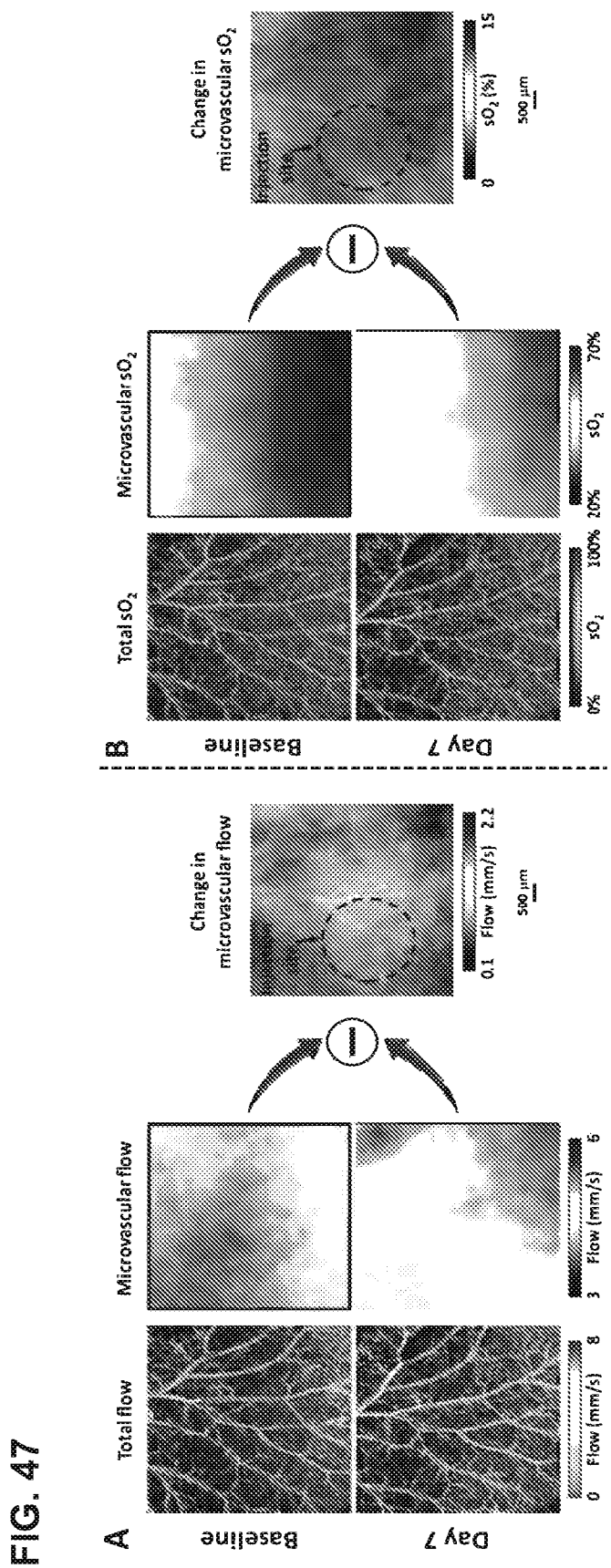

FIG. 47: Influence on microvascular flow and oxygen saturation following injection of citrate/saline vehicle in the mouse ear. Citrate/saline vehicle (10 µL) was intradermally injected in the mouse ear. Microvascular flow (panel A) and oxygen saturation (panel B) were assessed before injection (baseline) and 7 days later.

Figures 48A, 48B:
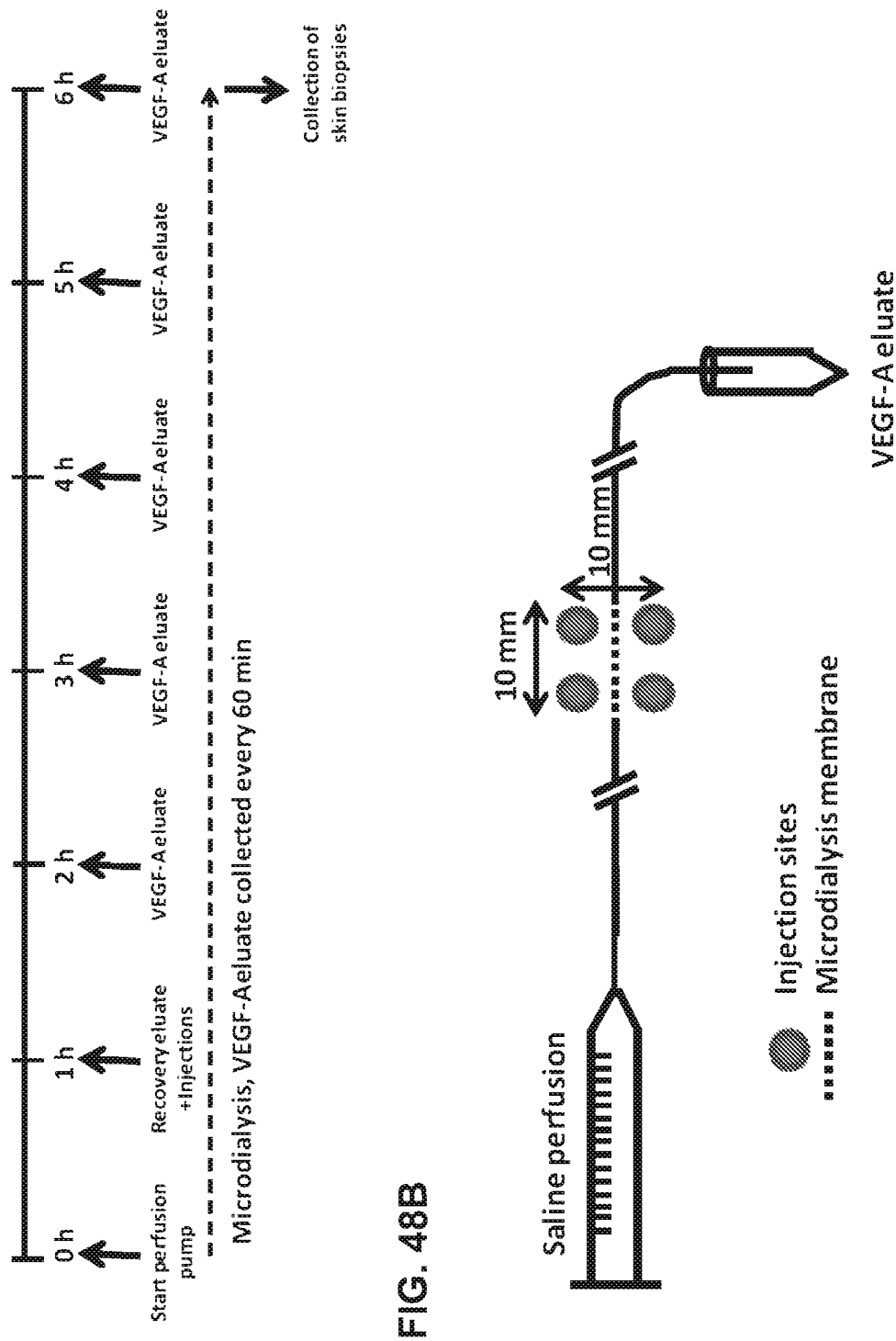

FIG. 48A and FIG. 48B: The experimental design for Example 16 is illustrated in FIG. 48A. Placement of VEGF-A modified RNA injections for Example 16 is illustrated in FIG. 48B.

Figure 49:
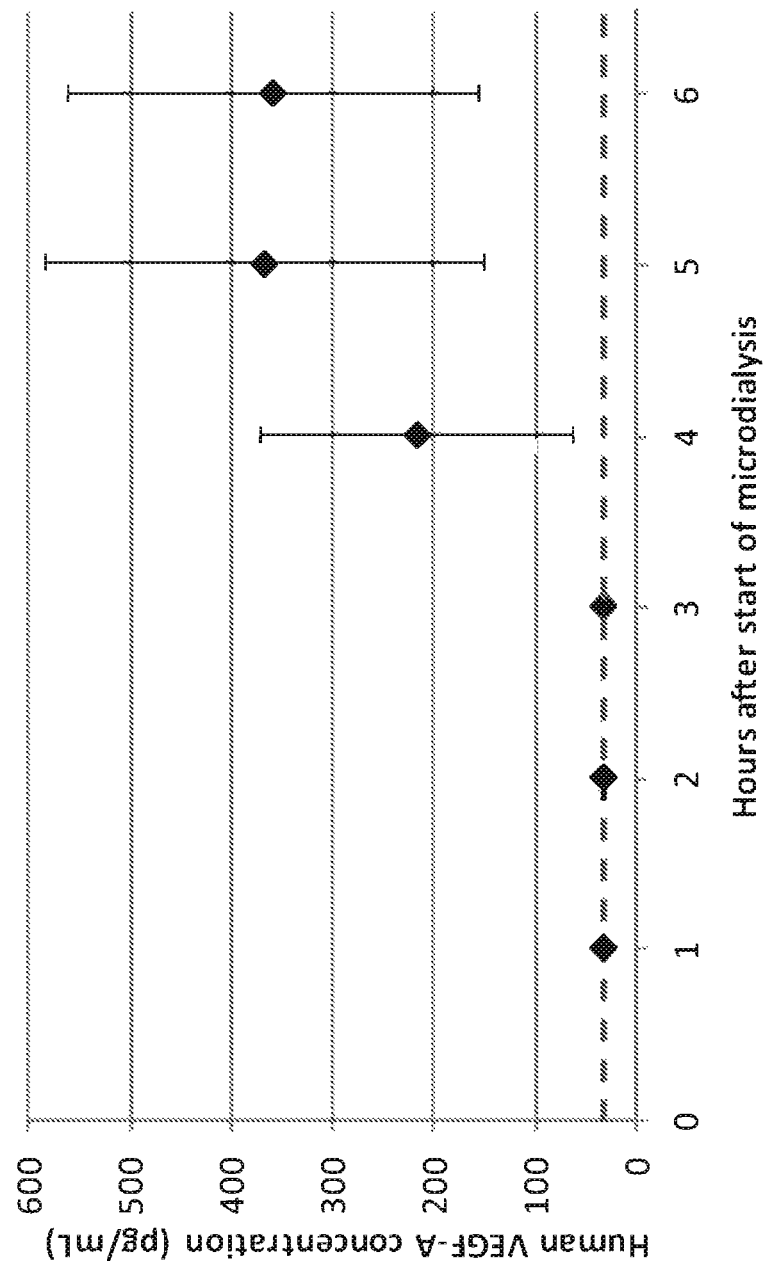

FIG. 49: Human VEGF-A concentrations in microdialysis eluates from rabbits intradermally injected with VEGF-A modified RNA. Concentrations of human VEGF-A in eluates from 100 kDa microdialysis probes intradermally inserted in the rabbit hind leg. Values presented are mean±SEM. Microdialysis was started at t=0 h and four id injections of VEGF-A modified RNA injections (50 µg each) were given at t=1 h. Dotted line indicates Lower Limit of Quantification (LLOQ, 33.4 pg/mL). Two probes were inserted in each rabbit, n=4 rabbits.

Figure 50A:
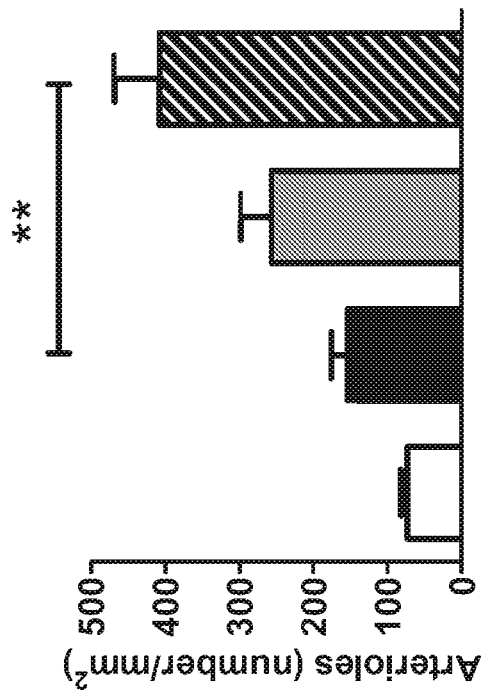
Figure 50B:
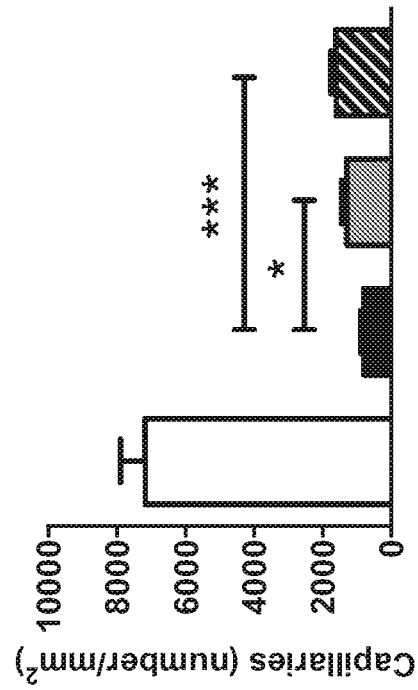
Figure 50C:
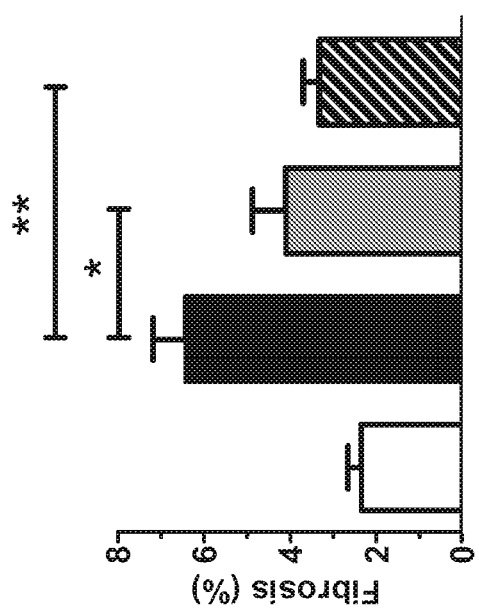

FIG. 50A, FIG. 50B, and FIG. 50C: Effects on capillary density (FIG. 50A), arteriole density (FIG. 50B), and fibrosis (FIG. 50C) following intracardiac injection of human VEGF-A modified RNA in pigs subjected to myocardial infarction in vivo. Mini pigs were subjected to permanent ligation of the left anterior descending coronary artery and 7 days later epicardially injected with VEGF-A modified RNA (1 mg, filled grey bar (n=8), or 10 mg, hatched bar (n=8)) or citrate/saline (filled black bar, n=8). A separate group of animals underwent a sham procedure (coronary artery not ligated and epicardial injections not given (open bar, n=5). Two months after the ligation, the animals were terminated and cardiac tissue harvested for assessment of capillary density (FIG. 50A) in the peri-infarct (border) zone. Shown are means±SEM. *; $P<0.05$ and *; $P<0.001$ vs the citrate/saline-treated animals (one-way ANOVA and Dunnett's post test). In FIG. 50B, two months after the ligation, the animals were terminated and cardiac tissue harvested for assessment of arteriole density in the peri-infarct (border) zone. Shown are means±SEM. ; $P<0.0$ vs the citrate/saline-treated animals (one-way ANOVA and Dunnett's post test). In FIG. 50C, two months after the ligation, the animals were terminated and cardiac tissue harvested for assessment of fibrosis (collagen deposition) remote from the infarcted area. Shown are means±SEM. *; $P<0.05$ and **; $P<0.01$ vs the citrate/saline-treated animals (one-way ANOVA and Dunnett's post test).

Figure 51:
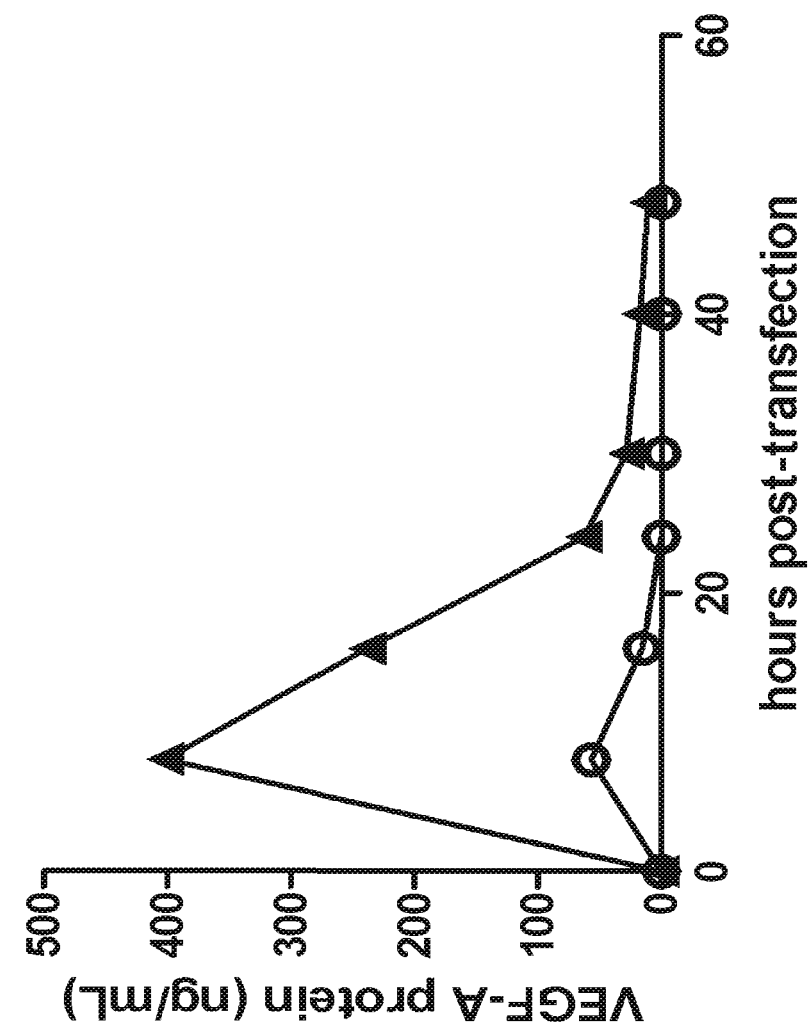

FIG. 51: Time profile of human VEGF-A protein production after VEGF-A modified RNA transfection in human aortic smooth muscle cells (hAoSMC, open circles) and in human cardiomyocytes derived from induced pluripotent cells (hiPS-CM, filled triangles). Data shown are means±SEM.

Figure 52A:
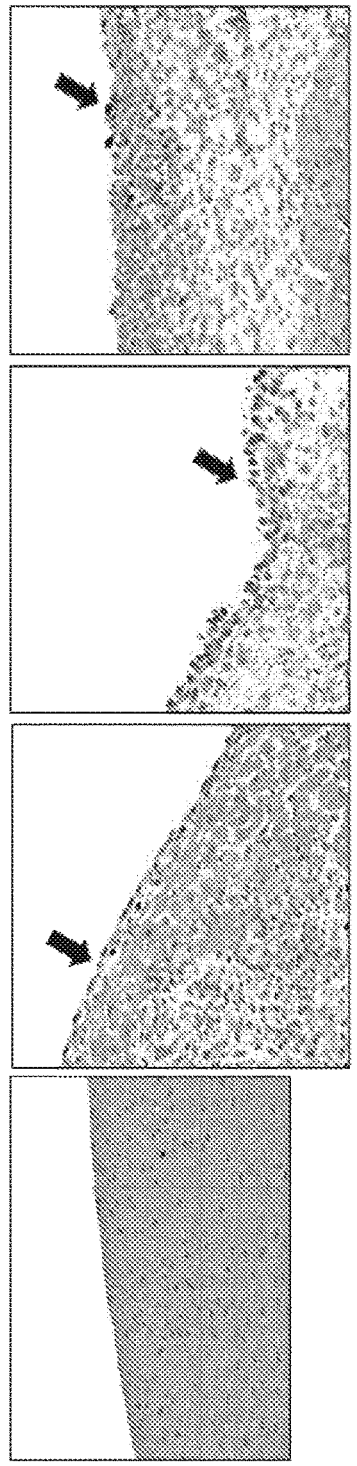
Figure 52B:
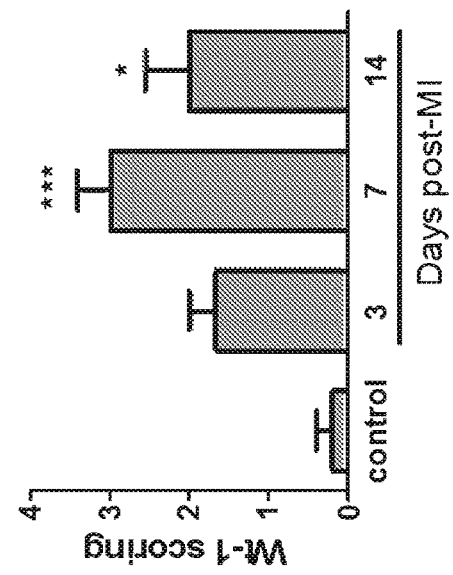

FIG. 52A and FIG. 52B: FIG. 52A illustrates immunohistochemistry of Wilms tumor 1 transcription factor (Wt-1) as a marker of Epicardium-Derived Cells (EPDC) in the normal non-infarcted mouse heart (control) and in hearts subjected to permanent occlusion of the left anterior descending coronary artery for 3, 7 or 14 days before tissue harvesting. Arrows indicate Wt-1 expression. FIG. 52B illustrates scoring of occurrence of Wt-1+ cells in the normal non-infarcted mouse heart (control) and in hearts subjected to permanent occlusion of the left anterior descending coronary artery for 3, 7 or 14 days before tissue harvesting.

MI; Myocardial Infarction. *; $P<0.05$, ***; $P<0.001$ vs Control, n=3-5 within each study group.

5. DETAILED DESCRIPTION

All references referred to are incorporated herein by reference in their entireties.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

5.1. Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range.

Unless otherwise indicated herein, each individual value is incorporated into the specification as if it were individually recited herein.

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

As used herein, the term "administering" refers to the placement of a pharmaceutical composition or a pharmaceutical formulation comprising at least one modified RNA, into a subject by a method or route that results in at least partial localization of the pharmaceutical composition or the pharmaceutical formulation, at a desired site or tissue location. In some embodiments, the pharmaceutical composition or the pharmaceutical formulation comprising modified RNA can be administered by any appropriate route that results in effective treatment in the subject, i.e. administration results in delivery to a desired location or tissue in the subject where at least a portion of the protein expressed by the modified RNA is located at a desired target tissue or target cell location.

Administration can be intramuscular, transarterial, intraperitoneal, intravenous, intraarterial, subcutaneous, intraventricular, intradermal, intracardiac, epicardiac, through a portal vein catheter, through a coronary sinus catheter, and/or direct administration into the area to be treated. Pharmaceutical compositions are specially formulated for each route of administration resulting in administration-specific pharmaceutical formulations.

The term "composition" used herein is generally understood to mean a combination of at least two parts or elements that make up something. For example, a composition as used herein usually comprises at least a polynucleotide, primary construct or modified RNA according to the disclosure and a suitable carrier or excipient.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

The term "consisting essentially of" limits the scope of a claim to the specified materials or steps "and those that do not materially affect the basic and novel characteristic(s)" of the claimed invention. In re *Herz*, 537 F.2d 549, 551-52, 190 USPQ 461, 463 (CCPA 1976) (emphasis in original) (Prior art hydraulic fluid required a dispersant which appellants argued was excluded from claims limited to a functional fluid "consisting essentially of" certain components.

The term "consisting of" refers to compositions, methods, and respective components thereof as described herein, which are exclusive of any element not recited in that description of the embodiment.

The terms "disease" or "disorder" are used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, sickness, illness, complaint, indisposition, or affection.

As used herein, the term "disease responsive to VEGF-A therapy" refers to a disorder that shows improvement of one or more symptoms or clinical markers after administration of a pharmaceutical composition or a pharmaceutical formulation comprising VEGF-A protein or an agent capable of producing VEGF-A protein, such as the modified RNA disclosed herein. Alternatively, a disease is "responsive" to VEGF-A therapy if the progression of the disease is reduced or halted with the administration of a pharmaceutical composition or a pharmaceutical formulation comprising VEGF-A protein or an agent capable of producing VEGF-A protein. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total).

As used herein, the term "divalent cation" refers to an ionic species with a positive valence of 2. For example, a magnesium ion, $Mg^{2+}$, and a calcium ion, $Ca^{2+}$ are divalent cations.

A "dosage form" is the physical form in which a drug (for example, a modified RNA) is produced and dispensed, such as a tablet (coated, delayed release, dispersible, etc.), a capsule, an ointment, or an injectable (powder, solution).

The phrase "drug product" means a finished dosage form, for example, tablet, capsule, solution, etc., that contains an active drug ingredient (for example, a modified RNA) generally, but not necessarily, in association with inactive ingredients.

The term "effective amount" as used herein refers to the amount of therapeutic agent (for example, a modified RNA), pharmaceutical composition, or pharmaceutical formulation, sufficient to reduce at least one or more symptom(s) of the disease or disorder, or to provide the desired effect. For example, it can be the amount that effects a therapeutically or prophylactically significant reduction in a symptom or clinical marker associated with a cardiac dysfunction or other disorder when administered to a typical subject who has a cardiovascular condition, or other disease or disorder.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

The term "formulation" or "pharmaceutical formulation" as used herein refers to a type of composition that comprises a pharmaceutical mixture or solution containing an active pharmaceutical ingredient (for example, a modified RNA), together with pharmaceutically acceptable carriers/diluents/excipients suitable to be administered to a mammal (e.g., a human in need thereof) via a particular route of administration. For example, a "formulation" as used herein can be specifically formulated to include suitable delivery agents and/or other pharmaceutically acceptable carriers for administration via one or more of a number of routes, such as via intramuscular, intradermal, subcutaneous, or intracardiac route, through a portal vein catheter, through a coronary sinus catheter, and/or by direct administration into the area to be treated. A "formulation" can therefore be understood to be a composition specially formulated for a particular route of administration. Formulations can be the compositions present in a particular dosage form.

As used herein, the term "modified RNA" refers to RNA molecules containing one, two, or more than two nucleoside modifications comparing to adenosine (A) ((2R,3R,4S,5R)-2-(6-amino-9H-purin-9-yl)-5-(hydroxymethyl)oxolane-3,4-diol), guanosine (G) (2-Amino-9-[3,4-dihydroxy-5-(hydroxymethyl)oxolan-2-yl]-3H-purin-6-one), cytidine (C) (4-amino-1-[3,4-dihydroxy-5-(hydroxymethyl)tetrahydrofuran-2-yl] pyrimidin-2-one), and uridine (U) (1-[(3R,4S,5R)-3,4-dihydroxy-5-(hydroxymethyl)oxolan-2-yl]pyrimidine-2,4-dione), or compared to AMP, GMP, CMP, and UMP, in RNA molecules, or a portion thereof. Non-limiting examples of nucleoside modifications are provided elsewhere in this specification. Where the nucleotide sequence of a particular claimed RNA is otherwise identical to the sequence of a naturally-existing RNA molecule, the modified RNA is understood to be an RNA molecule with at least one modification different from those existing in the natural counterpart. The difference can be either in the chemical change to the nucleoside/nucleotide or in the position of that change within the sequence. In one embodiment, the modified RNA is modified messenger RNA (or "modified mRNA").

As used herein, the term "modulating a physiological process" refers to a regulation of diverse functions and physical or chemical operations of living organisms and their parts, such as cells or tissues. For example, for physiological processes where VEGF-A plays central roles, the modulation may include inducing angiogenesis, stimulating vascular cell proliferation, increasing proliferation and/or altering the fate of epicardial derived progenitor cells, upregulating endothelialization, inducing cardiac regeneration, increasing revascularization of tissue grafts for wound healing, improving vascular function, increasing tissue perfusion and new vessel formation, reducing scar tissue, increasing preload recruitable stroke work (PRSW), increasing maximal pressure development, increasing inotropic function, increasing left ventricle ejection fraction (LVEF), decreasing levels of biomarkers associated with cardiac dysfunction (e.g., NT-proBNP, BNP, hsTnT and hsTnI), reducing infarct size, reducing fibrosis of cardiac tissue and/or improving cardiac function.

As used herein, the term "nucleic acid," in its broadest sense, includes any compound and/or substance that comprises a polymer of nucleotides linked via a phosphodiester bond. These polymers are often referred to as oligonucleotides or polynucleotides, depending on the size. The terms "polynucleotide sequence" and "nucleotide sequence" are also used interchangeably herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Drug-approval agencies (e.g., EMA, US-FDA) provide guidance and approve pharmaceutically acceptable compounds, materials, compositions, and/or dosage forms. Examples can be listed in Pharmacopeias.

The phrase "pharmaceutically acceptable excipient" is employed herein to refer to a pharmaceutically acceptable material chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent.

As used herein, "polypeptide" means a polymer of amino acid residues (natural or unnatural) linked together most often by peptide bonds. The term, as used herein, refers to proteins, polypeptides, and peptides of any size, structure, or function. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are sometime used interchangeably herein.

The term "recombinant," as used herein, means that a protein is derived from a prokaryotic or eukaryotic expression system through the use of a nucleic acid that has been genetically manipulated by the introduction of a "heterologous nucleic acid" or the alteration of a native nucleic acid.

The term "statistically significant" or "significantly" refers to statistical significance. The term refers to statistical evidence that there is a difference. It can be defined as the probability of making a decision to reject the null hypothesis when the null hypothesis is actually true. The decision is often made using the p-value. Any other measure of significant significance that is well-known in the art can be used.

The terms "subject" and "individual" are used interchangeably herein, and refer to an animal, for example a human, to whom treatment, including prophylactic treatment, with methods and compositions described herein, is or are provided. For treatment of those conditions or disease states which are specific for a specific animal such as a human subject, the term "subject" refers to that specific animal.

The term "substantially free of" refers to a condition in which a composition or formulation has no significant amounts of specific elements. For example, a composition or formulation "substantially free of" divalent cations contains little or no divalent cations.

As used herein, a subject or individual who is "suffering from" a disease, disorder, and/or condition has been diagnosed with or displays one or more symptoms of a disease, disorder, and/or condition. In some embodiments, a subject may be at risk of suffering from a disease, disorder and/or condition.

The term "tissue" refers to a group or layer of similarly specialized cells which together perform certain special functions. The term "tissue-specific" refers to a source or defining characteristic of cells from a specific tissue.

As used herein, the terms "treat" or "treatment" or "treating" refers to therapeutic treatment, wherein the object is to prevent or slow the development of the disease, such as slow down the development of a cardiac disorder, or reducing at least one adverse effect or symptom of a vascular condition, disease or disorder, such as, any disorder characterized by insufficient or undesired cardiac function.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

5.2. Modified RNA Encoding VEGF-A Polypeptides

It is of great interest in the fields of therapeutics, diagnostics, reagents and for biological assays to be able to deliver a nucleic acid, e.g., a ribonucleic acid (RNA) inside a cell, whether in vitro, in vivo, in situ, or ex vivo, such as to cause intracellular translation of the nucleic acid and production of an encoded polypeptide of interest.

Naturally occurring RNAs are synthesized from four basic ribonucleotides: ATP, CTP, UTP and GTP, but may contain post-transcriptionally modified nucleotides. Further, approximately one hundred different nucleoside modifications have been identified in RNA (Rozenski, J, Crain, P, and McCloskey, J., The RNA Modification Database: 1999 update, Nucl Acids Res, (1999) 27: 196-197).

According to the present disclosure, these RNAs are preferably modified as to avoid the deficiencies of other RNA molecules of the art (e.g., activating the innate immune response and rapid degradation upon administration). Hence, these polynucleotides are referred to as modified RNA. In some embodiments, the modified RNA avoids the innate immune response upon administration to a subject. In some embodiments, the half-life of the modified RNA is extended compared to an unmodified RNA.

In preferred embodiments, the RNA molecule is a messenger RNA (mRNA). As used herein, the term "messenger RNA" (mRNA) refers to any polynucleotide that encodes a polypeptide of interest and that is capable of being translated to produce the encoded polypeptide of interest in vitro, in vivo, in situ or ex vivo.

As depicted in FIG. 1A, traditionally, the basic components of an mRNA molecule include at least a coding region, a 5' untranslated region (UTR), a 3' untranslated region (UTR), a 5' cap and a poly-(A) tail. Building on this wild type modular structure, the present disclosure expands the scope of functionality of traditional mRNA molecules by providing polynucleotides or primary RNA constructs which maintain a modular organization, but which comprise one or more structural and/or chemical modifications or alterations that impart useful properties to the polynucleotide including, in some embodiments, the lack of a substantial induction of the innate immune response of a cell into which the polynucleotide is introduced.

The modified RNAs can include any useful modification relative to the standard RNA nucleotide chain, such as to the sugar, the nucleobase (e.g., one or more modifications of a nucleobase, such as by replacing or substituting an atom of a pyrimidine nucleobase with optionally substituted amino, optionally substituted thiol, optionally substituted alkyl (e.g., methyl or ethyl), or halo (e.g., chloro or fluoro), or the internucleoside linkage (e.g., one or more modification to the phosphodiester backbone). The modified RNAs can optionally include other agents (e.g., RNAi-inducing agents, RNAi agents, siRNA, shRNA, miRNA, antisense RNA, ribozymes, catalytic DNA, tRNA, RNA that induce triple helix formation, aptamers, vectors, etc.).

U.S. Patent Application Publication No. 2014/0073687 discloses exemplary modified RNAs with several useful modifications, for example, at least one or more modified nucleosides chosen from 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G). Additional modifications are described in U.S. Patent Application Publication No. 2015/0051268, filed on Oct. 7, 2014 and U.S. Pat. No. 9,061,059, filed on Feb. 3, 2014. Accordingly, all of these modifications are incorporated herein in their entirety by reference. Additional modifications are described herein.

As non-limiting examples, in some embodiments, a modified RNA can include, for example, at least one uridine monophosphate (UMP) that is modified to form N1-methyl-pseudo-UMP. In some embodiments, the N1-methyl-pseudo-UMP is present instead of UMP in a percentage of the UMPs in the sequence of 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all UMP have been replaced by N1-methyl-pseudo-UMP.

In some embodiments, a modified RNA can (further) include, for example, at least one cytidine monophosphate (CMP) that is modified to form methyl-CMP. In some embodiments, the methyl-CMP is present instead of CMP in a percentage of the CMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all CMP have been replaced by 5-methyl-CMP.

In some embodiments, a modified RNA can (further) include, for example, at least one adenosine monophosphate (AMP) that is modified to form N6-methyl-AMP. In some embodiments, the N6-methyl-AMP is present instead of AMP in a percentage of the AMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all AMP have been replaced by N6-methyl-AMP.

In some embodiments, a modified RNA can (further) include, for example, at least one guanosine monophosphate (GMP) that is modified to form 7-methyl-GMP. In some embodiments, the 7-methyl-GMP is present instead of GMP in a percentage of the GMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all GMP have been replaced by 7-methyl-GMP.

In some embodiments, a modified RNA can (further) include, for example, at least one or more modified nucleosides chosen from 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and N1-methyl-pseudouridine, or any combination thereof. Each possibility and combination represents a separate embodiment of the present disclosure.

In some embodiments, modified RNAs comprise a modification to 5' cap, such as a 5' diguanosine cap. In some embodiments, modified RNAs comprise a modification to a coding region. In some embodiments, modified RNAs comprise a modification to a 5' UTR. In some embodiments, modified RNAs comprise a modification to a 3' UTR. In some embodiments, modified RNAs comprise a modification to a poly-(A) tail. In some embodiments, modified RNAs comprise any combination of modifications to a coding region, 5' cap, 5' UTR, 3' UTR, or poly-(A) tail. In some embodiments, a modified RNA can optionally be treated with an alkaline phosphatase.

In some embodiments, a modified RNA encodes a Vascular Endothelial Growth Factor (VEGF) polypeptide, any one of a large family of VEGF proteins that play a central role in the control of cardiovascular physiological function in general, and arteriogenesis in particular (Holmes D. I. et al., Genome Biol., (2005)6(2):209). VEGF's roles also include activation of nitric oxide (NO) signaling, vascular permeability, developmental and post-natal angiogenesis, tumor angiogenesis, arteriogenesis, endothelial replication, and as cell fate switch for multipotent cardiovascular progenitors.

It will be appreciated by those of skill in the art that for any particular VEGF gene there may exist one or more variants or isoforms. Non-limiting examples of the VEGF-A polypeptides in accordance with the present disclosure are listed in Table 1. It will be appreciated by those of skill in the art that the sequences disclosed in the Table 1 contain potential flanking regions. These are encoded in each nucleotide sequence either to the 5' (upstream) or 3' (downstream) of the open reading frame. The open reading frame is definitively and specifically disclosed by teaching the nucleotide reference sequence. It is also possible to further characterize the 5' and 3' flanking regions by utilizing one or more available databases or algorithms. Databases have annotated the features contained in the flanking regions of the NCBI sequences and these are available in the art.

TABLE 1

Homo sapiens VEGF-A mRNA isoforms.

| Description | NM Ref. | NP Ref. |
|---|---|---|
| Homo sapiens vascular endothelial growth factor A (VEGF-A), transcript variant 1, mRNA | NM_001171623.1 | NP_001165094.1 |
| Homo sapiens vascular endothelial growth factor A (VEGF-A), transcript variant 1, mRNA | NM_001025366.2 | NP_001020537.2 |
| Homo sapiens vascular endothelial growth factor A (VEGF-A), transcript variant 2, mRNA | NM_001171624.1 | NP_001165095.1 |
| Homo sapiens vascular endothelial growth factor A (VEGF-A), transcript variant 2, mRNA | NM_003376.5 | NP_003367.4 |
| Homo sapiens vascular endothelial growth factor A (VEGF-A), transcript variant 3, mRNA | NM_001171625.1 | NP_001165096.1 |
| Homo sapiens vascular endothelial growth factor A (VEGF-A), transcript variant 3, mRNA | NM_001025367.2 | NP_001020538.2 |
| Homo sapiens vascular endothelial growth factor A (VEGF-A), transcript variant 4, mRNA | NM_001171626.1 | NP_001165097.1 |

TABLE 1-continued

Homo sapiens VEGF-A mRNA isoforms.

| Description | NM Ref. | NP Ref. |
|---|---|---|
| Homo sapiens vascular endothelial growth factor A (VEGF-A), transcript variant 4, mRNA | NM_001025368.2 | NP_001020539.2 |
| Homo sapiens vascular endothelial growth factor A (VEGF-A), transcript variant 4, mRNA | NM_001317010.1 | NP_001303939.1 |
| Homo sapiens vascular endothelial growth factor A (VEGF-A), transcript variant 5, mRNA | NM_001171627.1 | NP_001165098.1 |
| Homo sapiens vascular endothelial growth factor A (VEGF-A), transcript variant 5, mRNA | NM_001025369.2 | NP_001020540.2 |
| Homo sapiens vascular endothelial growth factor A (VEGF-A), transcript variant 6, mRNA | NM_001171628.1 | NP_001165099.1 |
| Homo sapiens vascular endothelial growth factor A (VEGF-A), transcript variant 6, mRNA | NM_001025370.2 | NP_001020541.2 |
| Homo sapiens vascular endothelial growth factor A (VEGF-A), transcript variant 7, mRNA | NM_001171629.1 | NP_001165100.1 |
| Homo sapiens vascular endothelial growth factor A (VEGF-A), transcript variant 7, mRNA | NM_001033756.2 | NP_001028928.1 |
| Homo sapiens vascular endothelial growth factor A (VEGF-A), transcript variant 8, mRNA | NM_001171630.1 | NP_001165101.1 |
| Homo sapiens vascular endothelial growth factor A (VEGF-A), transcript variant 8, mRNA | NM_001171622.1 | NP_001165093.1 |
| Homo sapiens vascular endothelial growth factor A (VEGF-A), transcript variant 9, mRNA | NM_001204385.1 | NP_001191314.1 |
| Homo sapiens vascular endothelial growth factor A (VEGF-A), transcript variant 9, mRNA | NM_001204384.1 | NP_001191313.1 |
| Homo sapiens vascular endothelial growth factor A (VEGF-A), transcript variant 10, mRNA | NM_001287044.1 | NP_001273973.1 |

It will be appreciated by those of skill in the art that RNA molecules encoding a VEGF-A polypeptide, e.g., a human VEGF-A polypeptide, can be designed according to the VEGF-A mRNA isoforms listed in the Table 1. One of ordinary of skill in the art is generally familiar with the multiple isoforms of the remaining VEGF family members.

In one embodiment, the present disclosure provides for a modified RNA encoding a VEGF-A polypeptide (e.g., SEQ ID NO: 2). In some embodiments, a modified RNA encodes a VEGF-A polypeptide, wherein the modified RNA comprises SEQ ID NO: 1. In some embodiments, the modified RNA further comprises a 5' cap, a 5' UTR, a 3' UTR, a poly(A) tail, or any combination thereof. In some embodiments, the 5' cap, the 5' UTR, the 3' UTR, the poly(A) tail, or any combination thereof may include one or more modified nucleotides.

In some embodiments, a modified RNA encoding a VEGF-A polypeptide can have the structure as depicted in FIG. 1B, which is SEQ ID NO: 1.

In some embodiments, a modified RNA encodes a VEGF polypeptide, wherein the modified RNA comprises one or more modified UMP nucleotides within the nucleic acid sequence of SEQ ID NO: 1. In some embodiments, a modified RNA encoding a VEGF-A polypeptide can include, for example, at least one of the UMP is modified to form N1-methyl-pseudo-UMP. In some embodiments, the N1-methyl-pseudo-UMP is present instead of UMP in a percentage of the UMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all UMP have been replaced by N1-methyl-pseudo-UMP.

In some embodiments, a modified RNA encodes a VEGF polypeptide, wherein the modified RNA (further) comprises one or more CMP modified nucleotides within the nucleic acid sequence of SEQ ID NO: 1. In some embodiments, the modified RNA encoding a VEGF-A polypeptide can include, for example, at least one of the CMP is modified to form methyl-CMP. In some embodiments, the methyl-CMP is present instead of CMP in a percentage of the CMPs in the sequence chosen from 0.1%, 2%, 3%, 4%, 1%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all CMP have been replaced by 5-methyl-CMP.

In some embodiments, a modified RNA encodes a VEGF polypeptide, wherein the modified RNA (further) comprises one or more AMP modified nucleotides within the nucleic acid sequence of SEQ ID NO: 1. In some embodiments, the modified RNA encoding a VEGF-A polypeptide can include, for example, at least one of the AMP is modified to form N6-methyl-AMP. In some embodiments, the N6-methyl-AMP is present instead of AMP in a percentage of the AMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all AMP have been replaced by N6-methyl-AMP.

In some embodiments, a modified RNA encodes a VEGF polypeptide, wherein the modified RNA (further) comprises one or more modified GMP nucleotides within the nucleic acid sequence of SEQ ID NO: 1. In some embodiments, the modified RNA can include, for example, at least one of the GMP is modified to form 7-methyl-GMP. In some embodiments, the 7-methyl-GMP is present instead of GMP in a percentage of the GMPs in the sequence chosen from 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all GMP have been replaced by 7-methyl-GMP.

In some embodiments, a modified RNA encodes a VEGF polypeptide, wherein the modified RNA (further) comprises one or more modified nucleotides within the nucleic acid sequence of SEQ ID NO: 1. In some embodiments, the modified RNA encoding a VEGF-A polypeptide can include, for example, at least one or more modified nucleosides chosen from 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and N1-methyl-pseudouridine, or any combination thereof. Each possibility and combination represents a separate embodiment of the present disclosure.

5.3. Compositions Comprising Modified RNA

Some embodiments relate to compositions, including specific formulations, comprising disclosed modified RNAs. In some embodiments, a formulation comprises a pharmaceutically effective amount of one or more modified RNAs.

In some embodiments, a pharmaceutical composition can comprise at least one or more modified RNAs in a lipid-based complex, such as liposomes, lipoplexes, and lipid nanoparticles. In general, liposomes, lipoplexes, or lipid nanoparticles may be used to improve the efficacy of polynucleotide, primary construct, or modified RNA directed protein production as these formulations may be able to increase cell transfection by the polynucleotide, primary construct, or modified RNA; and/or increase the translation of encoded protein. One such example involves the use of lipid encapsulation to enable the effective systemic delivery of polyplex plasmid DNA (Heyes et al., Mol Ther. (2007) 15:713-720; herein incorporated by reference in its entirety). The liposomes, lipoplexes, or lipid nanoparticles may also be used to increase the stability of the polynucleotide, primary construct, or modified RNA.

Accordingly, in some embodiments, pharmaceutical compositions of modified RNAs include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical compositions.

In some embodiments, pharmaceutical compositions of modified RNA include a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res., (2008) 68:9788-9798; Strumberg et al. Int J Clin Pharmacol Ther, (2012) 50:76-78; Santel et al., Gene Ther, (2006) 13:1222-1234; Santel et al., Gene Ther, (2006) 13:1360-1370; Gutbier et al., Pulm Pharmacol. Ther., (2010) 23:334-344; Kaufmann et al. Microvasc Res, (2010) 80:286-293; Weide et al. J Immuno Ther., (2009) 32:498-507; Weide et al. J Immunother., (2008) 31:180-188; Pascolo Expert Opin. Biol. Ther. 4:1285-1294; Fotin-Mleczek et al., J. Immunother, (2011)34:1-15; Song et al., Nature Biotechnol., (2005) 23:709-717; Peer et al., Proc Natl Acad Sci USA., (2007) 6; 104:4095-4100; deFougerolles Hum Gene Ther., (2008) 19:125-132; all of which are incorporated herein by reference in its entirety).

In some embodiments, pharmaceutical compositions of modified RNA include a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, (2008), 2 (8), pp 1696-1702; herein incorporated by reference in its entirety).

Additional lipid-based compositions are discussed in U.S. Patent Application Publication No. 2015/0051268; herein incorporated by reference in its entirety. Accordingly, in some embodiments, pharmaceutical formulations of the modified RNA in accordance with this disclosure are formulated in lipid-based formulations as discussed in U.S. Patent Application Publication No. 2015/0051268.

In some embodiments of the present disclosure, pharmaceutical formulations of modified RNA do not include any lipid-based complex (such as liposomes, lipoplexes, or lipid nanoparticles) and are herein referred to as naked RNA formulations. WO 2012/103985 has suggested that naked RNA can penetrate cells only when it is formulated in the presence of divalent cations, preferably calcium. Furthermore, other studies have suggested and showed that calcium is needed for directing naked RNA molecules into animal tissues in vivo (Wolff J. A. et al., Science, (1999), 247, 1465-1468). Similarly, Probst et al. showed that injection of naked RNA in vivo strongly depends on the presence of calcium in the injection solution (Probst J. et al., Gene Ther, (2007) 14, 1175-1180). Accordingly, these studies dealing with delivery of naked RNA to cells and tissues have strongly suggested the need for calcium in the formulation.

Yet in some embodiments of the present disclosure, naked modified RNA is formulated with phosphate-buffered saline (PBS) buffer. For example, a modified RNA can be formulated with pH 7.4 PBS buffer substantially free of divalent cations. In some embodiments, a modified RNA can be formulated with pH 7.4 PBS buffer substantially free of calcium or magnesium. In some embodiments, a modified RNA can be formulated with pH 7.4 PBS buffer containing no calcium or magnesium.

In some embodiments, naked modified RNA is formulated with citrate saline buffer. For example, a modified RNA can be formulated with pH 7.0 citrate saline buffer substantially free of divalent cations. In some embodiments, a modified RNA can be formulated with pH 7.0 citrate saline buffer substantially free of calcium or magnesium. In some embodiments, a modified RNA can be formulated with pH 7.0 citrate saline buffer containing no calcium or magnesium. For example, a modified RNA can be formulated with pH 7.0 citrate saline buffer containing 10 mmol/L citrate, 130 mmol/L sodium chloride in Hyclone water, wherein the citrate saline buffer does not contain calcium or magnesium.

In some embodiments, naked modified RNA is formulated with tromethamine (THAM) buffer. For example, a modified RNA can be formulated with pH 8.0 THAM buffer substantially free of divalent cations. In some embodiments, a modified RNA can be formulated with THAM buffer substantially free of calcium or magnesium. In some embodiments, a modified RNA can be formulated with pH 8.0 THAM buffer containing no calcium or magnesium. For example, a modified RNA can be formulated with pH 8.0 THAM buffer (tromethamine AKA 2-amino-2-(hydroxymethyl)-1,3-propanediol, 300 mmol/L Tris-HCl), wherein the THAM buffer does not contain calcium or magnesium.

In some embodiments, naked RNA pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Excipients can also include, without limitation, polymers, core-shell nanoparticles, peptides, proteins, cells, hyaluronidase, nanoparticle mimics and combinations thereof. Various excipients for formulating pharmaceutical compositions and techniques for preparing the composition are known in the art (see Remington: The Science and Practice of Pharmacy, $22^{nd}$ Edition, Edited by Allen, Loyd V., Jr, Pharmaceutical Press; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, a naked RNA formulation comprises a pharmaceutically effective amount of one or more modified RNAs, wherein the formulation comprises a phosphate-buffered saline buffer and further comprises a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent. In some embodiments, the solvent is a non-aqueous solvent.

In some embodiments, a naked RNA formulation comprises a pharmaceutically effective amount of one or more modified RNAs, wherein the formulation comprises a THAM buffer and further comprises a pharmaceutically acceptable excipient. In some embodiments, the pharmaceutically acceptable excipient is chosen from solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent.

In some embodiments, a naked RNA formulation comprises a pharmaceutically effective amount of one or more modified RNAs, wherein the formulation comprises a citrate saline buffer and further comprises a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent.

In certain embodiments, formulations comprising the modified RNA in accordance with the present disclosure are in a lipid-based complex (such as liposomes, lipoplexes, and lipid nanoparticles), phosphate-buffered saline buffer, THAM buffer, or citrate saline buffer at a concentration of between 0.1 and 1 µg/µL. In some embodiments, formulations comprising the modified RNA in accordance with the present disclosure are formulated in a lipid-based complex (such as liposomes, lipoplexes, and lipid nanoparticles), phosphate-buffered saline buffer, THAM buffer, or citrate saline buffer at a concentration of between 1 and 10 µg/µL. In some embodiments, formulations comprising the modified RNA in accordance with the present disclosure are formulated in a lipid-based complex (such as liposomes, lipoplexes, and lipid nanoparticles), phosphate-buffered saline buffer, THAM buffer, or citrate saline buffer at a concentration of between 10 and 50 µg/µL.

In preferred embodiments, naked RNA formulations comprising the modified RNA in accordance with the present disclosure comprise a citrate saline buffer. In some embodiments, the formulation comprises a concentration of the modified RNA formulated in citrate saline buffer of between 0.1 and 1 µg/µL. In some embodiments, the formulation comprises a concentration of the modified RNA formulated in citrate saline buffer of between 1 and 10 μg/μL. In some embodiments, the formulation comprises a concentration of the modified RNA formulated in citrate saline buffer of between 10 and 50 μg/μL.

In some embodiments, a naked RNA formulation comprising a modified RNA encoding a VEGF-A polypeptide formulated in citrate saline buffer is less toxic to the subject than a lipid-based formulation.

5.4. Treating Subjects Suffering from Diseases Responsive to VEGF-A Therapy

Subjects with insufficient expression of VEGF-A can suffer from many vascular diseases including, without limitation, heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, and peripheral arterial disease. It is an aim of the present disclosure to treat subjects suffering from diseases responsive to VEGF-A therapy by direct administration of one or more modified RNA molecules encoding VEGF-A polypeptides. In some embodiments, naked VEGF-A RNA is administered to the subject in a citrate saline buffer without lipids and calcium.

In general, exogenous nucleic acids introduced into cells induce an innate immune response, resulting in interferon (IFN) production and cell death. However, modified RNAs have overcome at least some of these issues and are of great interest for therapeutics, diagnostics, reagents and for biological assays to deliver a nucleic acid, e.g., a ribonucleic acid (RNA) inside a cell, either in vivo or ex vivo, such as to cause intracellular translation of the nucleic acid and production of the encoded protein.

The modified RNAs and the proteins translated from the modified RNAs described herein can be used as therapeutic agents. For example, a modified RNA described herein can be administered to a subject, wherein the modified RNA is translated to produce a therapeutic protein of any VEGF family member, or a fragment thereof in the subject. Provided are methods for treatment of disease or conditions in humans and other mammals. All the formulations described herein for VEGF-A can be agreeably used with any other VEGF family member.

In some embodiments, compositions and particular formulations comprising one or more modified RNAs encoding VEGF-A polypeptides may be used for treatment of a disease such as heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, healing wounds, such as lacerations, critical limb ischemia, pulmonary hypertension, and peripheral arterial disease.

In some embodiments, formulations comprising one or more modified RNAs encoding VEGF-A polypeptides may be used to treat heart failure with reduced or preserved ejection fraction. In some embodiments, formulations comprising one or more modified RNA encoding VEGF-A polypeptides may be used to treat post-MI cardiac dysfunction. In some embodiments, formulations comprising one or more modified RNA encoding VEGF-A polypeptides may be used to treat ischemic heart disease. In some embodiments, formulations comprising one or more modified RNA encoding VEGF-A polypeptides may be used to treat a vascular injury from trauma or surgery. In some embodiments, formulations comprising one or more modified RNA encoding VEGF-A polypeptides may be used to treat a skin ulcer including a diabetic ulcer. In some embodiments, the formulations comprising one or more modified RNA encoding VEGF-A polypeptides may be used in wound healing, for example, in healing lacerations. In some embodiments, formulations comprising one or more modified RNA encoding VEGF-A polypeptides may be used to critical limb ischemia. In some embodiments, formulations comprising one or more modified RNA encoding VEGF-A polypeptides may be used to treat pulmonary hypertension. In some embodiments, formulations comprising one or more modified RNA encoding VEGF-A polypeptides may be used to treat peripheral arterial disease. In some embodiments, formulations comprising one or more modified RNA encoding VEGF-A polypeptides may be used to treat kidney disease. In some embodiments, formulations comprising one or more modified RNA encoding VEGF-A polypeptides may be used to treat a disease involving skin grafting and tissue grafting.

Other aspects of the disclosure relate to administration of the formulations comprising modified RNAs to subjects in need thereof. Administration of the formulation can be intramuscular, transarterial, intraperitoneal, intravenous, intraarterial, subcutaneous, intraventricular, intradermal, intracardiac, epicardiac, through a portal vein catheter, through a coronary sinus catheter, and/or direct administration into the area to be treated.

However, the present disclosure also encompasses the delivery of naked modified RNA molecules or modified RNA complexes, and/or pharmaceutical, prophylactic, or diagnostic formulations thereof, by any appropriate route taking into consideration likely advances in the sciences of drug delivery.

As non-limiting examples, in some embodiments, formulations in accordance with the present disclosure are administered to the subject via intramuscular, intradermal, subcutaneous, intracardiac or epicardiac route, through a portal vein catheter, through a coronary sinus catheter, and/or by direct administration into the area to be treated. In some embodiments, the formulation is administered to the subject intramuscularly. In some embodiments, the formulation is administered to the subject intradermally. In some embodiments, the formulation is administered to the subject subcutaneously.

In some embodiments, the formulation is administered to the subject intracardially, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, the formulation is administered to the subject through a portal vein catheter, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, the formulation is administered to the subject through a coronary sinus catheter, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, the formulation is administered to the subject by direct administration into the area to be treated, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. For example, the formulation is administered to the subject by direct injection to the damaged area during open heart surgery, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, the formulation is administered to the subject epicardially, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. For example, in patients undergoing coronary artery by-pass grafting (CABG), the formulation is administered to the patient from the external side of the heart, preferably at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In each of the embodiments in this paragraph, the "multiple administrations" can be separated from each other by short (1-5 mins), medium (6-30 minutes), or long (more than 30 minutes, hours, or even days) intervals of time.

The formulation may be administered to a subject using any amount of administration effective for treating a disease, disorder, and/or condition. The exact amount required will vary from subject to subject, depending on the species, age, and general condition of the subject, the severity of the disease, the particular formulation, its mode of administration, its mode of activity, and the like. It will be understood, however, that the total daily usage of the formulations may be decided by the attending physician within the scope of sound medical judgment. The specific pharmaceutically effective, dose level for any particular patient will depend upon a variety of factors including the disease being treated and the severity of the disease; the activity of the specific compound employed; the specific formulation employed; the age, body weight, general health, sex and diet of the patient; the time of administration, route of administration, and rate of excretion of the specific compound employed; the duration of the treatment; drugs (for example, a modified RNA) used in combination or coincidental with the specific compound employed; and like factors well known in the medical arts.

In certain embodiments, formulations in accordance with the present disclosure are administered to a subject, wherein the formulations comprise a lipid-based complex (such as liposomes, lipoplexes, and lipid nanoparticles). In other embodiments, naked modified RNA is administered in phosphate-buffered saline buffer, THAM buffer, or citrate saline buffer. In other embodiments, naked modified RNA is administered in the absence of divalent cations, including calcium. In preferred embodiments, formulations for intra-cardiac or intradermal administration comprising the modified RNA are formulated in citrate saline buffer containing no calcium or magnesium. In some embodiments, the formulation comprises a concentration of the modified RNA formulated in citrate saline buffer of between 0.1 and 1 µg/µL. In some embodiments, the formulation comprises a concentration of the modified RNA formulated in citrate saline buffer of between 1 and 10 µg/µL. In some embodiments, the formulation comprises a concentration of the modified RNA formulated in citrate saline buffer of between 10 and 50 µg/µL.

In certain embodiments, formulations in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of modified RNA per subject body weight per day, one or more times a day, to obtain the desired therapeutic or prophylactic effect. The desired dosage may be delivered three times a day, two times a day, once a day, every other day, every third day, every week, every two weeks, every three weeks, every four weeks or once as a single dose, either in a bolus dose or in multiple administrations over a period of second, minutes or hours in a 24 hour period. In certain embodiments, the desired dosage may be delivered using multiple administrations (e.g., two, three, four, five, six, seven, eight, nine, ten, eleven, twelve, thirteen, fourteen, fifteen, sixteen, seventeen, eighteen, nineteen, twenty, or more administrations).

In some embodiments, formulations in accordance with the present disclosure may be administered at fixed-dosage levels. For example, formulations in accordance with the present disclosure may be administered at fixed-dosage levels from about 0.1 mg to about 1 mg, either per administration or per total dose. In some embodiments, formulations in accordance with the present disclosure may be administered at fixed-dosage levels from about 1 mg to about 10 mg, either per administration or per total dose. In some embodiments, formulations in accordance with the present disclosure may be administered at fixed-dosage levels from about 10 mg to about 25 mg, either per administration or per total dose. In some embodiments, formulations in accordance with the present disclosure may be administered at fixed-dosage levels from about 25 mg to about 50 mg, either per administration or per total dose. In some embodiments, formulations in accordance with the present disclosure may be administered at fixed-dosage levels from about 50 mg to about 100 mg, either per administration or per total dose. In some embodiments, formulations in accordance with the present disclosure may be administered at fixed-dosage levels from about 0.1 to about 25 mg, either per administration or per total dose. In some embodiments, formulations in accordance with the present disclosure may be administered at a fixed-dosage, preferably in multiple (e.g., two, three, four, five, six, seven, eight, nine, ten, eleven, twelve, thirteen, fourteen, fifteen, sixteen, seventeen, eighteen, nineteen, twenty, or more) administrations. For example, in some embodiments, formulations in accordance with the present disclosure may be administered at 0.1 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, formulations in accordance with the present disclosure may be administered at 1 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, formulations in accordance with the present disclosure may be administered at 10 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, formulations in accordance with the present disclosure may be administered at 25 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, formulations in accordance with the present disclosure may be administered at 50 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In some embodiments, formulations in accordance with the present disclosure may be administered at 100 mg fixed-dosage, either per administration or per total dose, preferably in multiple (e.g., two, three, four, five, six, seven, eight, nine, ten, eleven, twelve, thirteen, fourteen, fifteen, sixteen, seventeen, eighteen, nineteen, twenty, or more) administrations.

In some embodiments, formulations in accordance with the present disclosure are administered to a subject, wherein the formulation comprising a naked modified RNA encoding a VEGF-A polypeptide formulated in citrate saline buffer is less toxic to the subject than a lipid-based formulation. The assessments of toxicity due to RNA delivery in formulations in accordance with the present disclosure can be evaluated by methods well-known in the art. For example, cationic lipids are typically included in lipid formulations of RNA therapeutics to improve RNA encapsulation and stability. However, some cationic lipids may, in a dose-dependent manner, disrupt the integrity of a membrane structure, cause cell lysis and necrosis, and/or alter the expression of multiple genes in undesirable manner (Xue H. Y., Curr Pharm Des., (2015) 21(22):3140-7; its entirety is incorporated herein by reference). Accordingly, examples of toxicity can be assessed by measuring the degree of cell lysis and necrosis, and/or alteration to the expression of multiple genes due to RNA delivery in formulations in accordance with the present disclosure. At preclinical and clinical levels, systemic dose-dependent toxicities of some lipoplexes have been well-documented. Capture of some lipoplexes by Kupffer cells in the liver can trigger inflammatory responses, which may inflict damages to liver and result in elevated levels in major liver function indicators. Leukopenia and thrombocytopenia may also occur (Zhang J., Adv Drug Deliv Rev., (2005) 57(5):689-698; its entirety is incorporated herein by reference). Accordingly, examples of toxicity can be assessed by measuring the inflammatory responses due to RNA delivery in formulations in accordance with the present disclosure. In addition, examples of toxicity can be assessed by measuring infusion related reactions such as dyspnea, hypoxia, rigors, back pain, hypotension, and liver injury.

A subject suffering from a vascular disease is "responsive" to the treatment if one or more symptoms or clinical markers are reduced. Alternatively, a treatment is working if the progression of a disease is reduced or halted. For example, heart failure (HF) occurs when the heart is weakened and is not filled with, or cannot pump, enough blood to meet the body's needs for blood and oxygen. Likewise, a patient with ischemic heart disease (IHD) has heart problems caused by narrowed heart arteries. When arteries are narrowed, less blood and oxygen reaches the heart muscle. As a consequence of microvascular dysfunction, loss of functional vessels, and/or loss of cardiac tissue, a patient usually develops cardiac dysfunction post-MI. Furthermore, vascular structures are most commonly injured by penetrating trauma or surgery. Diabetes impairs numerous components of wound healing, and a patient with diabetic wound healing generally has altered blood flow due to vascular dysfunction. Accordingly, a patient with skin ulcer including diabetic ulcers usually has decreased or delayed would healing. Critical limb ischemia (CLI) is a severe obstruction of the arteries which markedly reduces blood flow to the extremities (hands, feet and legs) and has progressed to the point of severe pain and even skin ulcers, sores, or gangrene. Pulmonary hypertension (PH or PHTN) is an increase of blood pressure in the pulmonary artery, pulmonary vein, or pulmonary capillaries, together known as the lung vasculature, leading to shortness of breath, dizziness, fainting, leg swelling and other symptoms. Peripheral artery disease (PAD) is a narrowing of the peripheral arteries to the legs, stomach, arms, and head—most commonly in the arteries of the legs. These conditions are routinely clinically diagnosed based on various physical examinations with confirmation by echocardiography, blood tests, magnetic resonance imaging (MRI) electrocardiography, and other suitable tests. For example, the diagnosis of significant vascular injury rests upon close physical examination and imaging tests. Accordingly, a treatment for any one of these conditions is working if the patient shows less severe symptoms by physical examinations and/or improvements in testing results from echocardiography, blood tests, MRI, electrocardiography, or any other suitable and/or routine tests.

In some embodiments, the subject suffering from a vascular disease has suffered a myocardial infarction. In some embodiments, the subject suffered a myocardial infarction within about one month prior to treatment with the formulations disclosed herein.

In some embodiments, the myocardial infarction triggers activation of Epicardium-derived cells (EPDC) over time. In some embodiments, the subject suffering a myocardial infarction is treated with the formulations disclosed herein several days after the myocardial infarction, preferably at the peak time of EPDC activation. In some embodiments, the subject suffering a myocardial infarction is treated with the formulations disclosed herein about 7 days after the myocardial infarction. In some embodiments, the subject suffering a myocardial infarction is treated with the formulations disclosed herein about 10 days after the myocardial infarction, 2 weeks after the myocardial infarction, 3 weeks after the myocardial infarction, or 6 weeks after the myocardial infarction.

In some embodiments, therapy with the compositions or formulations described herein comprises treating myocardial infarction with reduced ejection fraction. In other embodiments, therapy comprises treating heart failure with preserved ejection fraction. In some embodiments, the composition or formulation is injected at the border zone between healthy and infarcted tissue.

In some embodiments, the subject suffering from a vascular disease also suffers from coronary artery disease, high blood pressure, diabetes, atrial fibrillation, valvular heart disease, cardiomyopathy or an infection.

In some embodiments, the subject suffering from a vascular disease is suffering from left ventricular dysfunction. In some embodiments, the subject has a left ventricular ejection fraction (LVEF) of less than about 40%. In some embodiments, the subject has a LVEF of less than about 45%.

In some embodiments, the subject is suffering from heart failure with reduced or preserved ejection fraction. In some embodiments, the subject with heart failure with reduced or preserved ejection fraction is classified as stage II-IV of the New York Heart Association Functional Classification (NYHAFC) guidelines.

In some embodiments, the subject has elevated levels of one or more biomarkers indicative of heart failure with reduced or preserved ejection fraction (e.g., NT-proBNP, BNP, hsTnT or hsTnI). In some embodiments, the subject has elevated BNP (b-type Natriuretic Peptide) levels. In some embodiments, the subject has BNP levels of about 100 pg/mL. In some embodiments, the subject has BNP levels of between about 100-300 pg/mL. In some embodiments, the subject has BNP levels of about 300-600 pg/mL. In some embodiments, the subject has BNP levels of about 600 pg/mL. In some embodiments, the subject BNP levels of between about 600-900 pg/mL. In some embodiments, the subject has elevated NT-proBNP (n-terminal pro b-type Natriuretic Peptide) levels. In some embodiments, the subject has NT-proBNP levels of about 450 pg/mL. In some embodiments, the subject is less than 50 years old and NT-proBNP levels of about 450 pg/mL. In some embodiments, the subject has NT-proBNP levels of about 900 pg/mL. In some embodiments, the subject is between about 50 and 75 years old and NT-proBNP levels of about 900 pg/mL. In some embodiments, the subject has NT-proBNP levels of at least 1800 pg/mL. In some embodiments, the subject is about 75 years old and NT-proBNP levels of about 1800 pg/mL. In some embodiments, the subject has elevated levels of hsTnT (high sensitivity Troponin T). In some embodiments, the subject has elevated levels of hsTnI (high sensitivity Troponin I).

In some embodiments, the subject has suffered a myocardial infarction within about a month prior to treatment with the formulations herein with an LVEF of less than about 45%.

In some embodiments, the subject is suffering from chronic ischemic heart failure with reduced or preserved ejection fraction with an LVEF of less than about 40%, an NT-proBNP level of at least about 600 pg/mL and is classified as stage II-IV on the NYHAFC guidelines.

Additionally, molecular measurements for vascular functions can be used to assess the improvements of the general pathophysiology. Examples of these measurements include enhanced nitric oxide (NO) availability, increased angiogenesis/arteriogenesis, and recruitment of stem cells to cardiac tissue. A patient suffering from a vascular disease is therefore "responsive" to the treatment if the patient shows improved molecular functions in these measurements.

5.5. Modulating a Physiological Process in a Mammalian Cell, Tissue, or Subject Another aspect of the present disclosure relates to the administration of a composition or a particular formulation comprising a modified RNA encoding a VEGF-A polypeptide for modulating a physiological process in a mammalian cell, tissue, or subject. In some embodiments, a method for modulating a physiological process in a mammalian cell, tissue, or subject comprises contacting the mammalian cell, tissue, or subject with a composition comprising the modified RNA in accordance with the present disclosure. As non-limiting examples, the modulation of a physiological process can include inducing angiogenesis, stimulating vascular cell proliferation, increasing proliferation and/or altering the fate of epicardial derived progenitor cells, upregulating endothelialization, inducing cardiac regeneration, increasing revascularization of tissue grafts for wound healing, improving vascular function, increasing tissue perfusion and new vessel formation, reducing scar tissue, increasing preload recruitable stroke work, increasing maximal pressure development, increasing inotropic function, increasing left ventricle ejection fraction (e.g., by between about 5 and 10%), decreasing levels of biomarkers associated with cardiac dysfunction (e.g., NT-proBNP, BNP, hsTnT and hsTnI), reducing infarct size, reducing fibrosis of cardiac tissue and/or improving cardiac function.

The term "contacting" or "contact" as used herein as in connection with contacting a cell, tissue, or subject with modified RNA as disclosed herein, includes touching or extremely close proximity of modified RNA with the cell, tissue, or subject. Accordingly, in some embodiments, the phrase "contacting" refers to a method of exposure, which can be direct or indirect. In one method such contact comprises direct injection of the composition into the cell, tissue, or subject through any means well known in the art. In another embodiment, contacting also encompasses indirect contacting, such as via topical medium that surrounds the tissue, or via any route known in the art. Each possibility represents a separate embodiment of the present disclosure.

In some embodiments, a method for inducing angiogenesis in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on inducing angiogenesis can be evaluated by methods well-known in the art (see, e.g., Lopez J. J. et al., Cardiovasc Res, (1998) 40, 272-281; Galiano R. D. et al., Am J Pathol., (2004) 164, 1935-1947; Lin Y. D. et al., Sci Transl Med., (2012) 4(146):146ra109; Zangi L. et al., Nat Biotechnol., (2013) 10, 898-907; all of which are incorporated herein by reference).

In some embodiments, a method for stimulating vascular cell proliferation in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on stimulating vascular cell proliferation can be evaluated by methods well-known in the art (see, e.g., Galiano R. D. et al., Am J Pathol, (2004) 164, 1935-1947; its entirety is incorporated herein by reference).

In some embodiments, a method for increasing proliferation and/or altering the fate of epicardial derived progenitor cells in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing proliferation and/or altering the fate of epicardial derived progenitor cells can be evaluated by methods well-known in the art (see, e.g., Zangi L. et al., Nat Biotechnol., (2013) 10, 898-907; its entirety is incorporated herein by reference).

In some embodiments, a method for upregulating endothelialization in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on upregulating endothelialization can be evaluated by methods well-known in the art (see, e.g., Galiano R. D. et al., Am J Pathol, (2004) 164, 1935-1947; its entirety is incorporated herein by reference).

In some embodiments, a method for inducing cardiac regeneration in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on inducing cardiac regeneration can be evaluated by methods well-known in the art (see, e.g., Zangi L. et al., Nat Biotechnol., (2013) 10, 898-907; Lin Y. D. et al., Sci Transl Med., (2012) 4(146):146ra109; both of which are incorporated herein by reference).

In some embodiments, a method for increasing revascularization of tissue grafts for wound healing in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing revascularization of tissue grafts for wound healing can be evaluated by methods well-known in the art (see, e.g., Tohyama H. et al., Chang Gung Med J, (2009) 32, 133-139; Chen J. et al., Exp Ther Med, (2012) 4, 430-434; both of which are incorporated herein by reference).

In some embodiments, a method for improving vascular function in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on improving vascular function can be evaluated by methods well-known in the art (see, e.g., Lopez J. J. et al., Cardiovasc Res, (1998) 40, 272-281; Tio R. A. et al., Hum Gene Ther., (1999) 10, 2953-2960; Sato K. et al., J Am Coll Cardiol., (2001) 37, 616-23; all of which are incorporated herein by reference).

In some embodiments, a method for increasing tissue perfusion and new vessel formation in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing tissue perfusion and new vessel formation can be evaluated by methods well-known in the art (see, e.g., Chiappini C., et al., Nat Mater., (2015) 14, 532-539; Lin Y. D. et al, Sci Transl Med., (2012) 4(146):146ra109; Zangi L. et al, Nat Biotechnol., (2013) 10, 898-907; all of which are incorporated herein by reference).

In some embodiments, a method for reducing scar tissue in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on reducing scar tissue can be evaluated by methods well-known in the art (see, e.g., Rosano J. M. et al., Cardiovasc Eng Technol., (2012) 3, 237-247; Galiano R. D. et al., Am J Pathol, (2004) 164, 1935-1947; Lin Y. D. et al., Sci Transl Med., (2012) 4(146):146ra109; Zangi L. et al., Nat Biotechnol. (2013) 10, 898-907; all of which are incorporated herein by reference).

In some embodiments, a method for improving cardiac function in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on improving cardiac function can be evaluated by methods well-known in the art (see, e.g., Rosano J. M. et al., Cardiovasc Eng Technol., (2012) 3, 237-247; Lin Y. D. et al, Sci Transl Med., (2012) 4(146):146ra109; Zangi L. et al, Nat Biotechnol., (2013) 10, 898-907; all of which are incorporated herein by reference).

In some embodiments, a method for increasing preload recruitable stroke work (PRSW) in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing preload recruitable stroke work can be evaluated by methods well-known in the art (see e.g., Fenely et al., JACC, (1992), 19(7):1522-30).

In some embodiments, a method for increasing maximal pressure development in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing maximal pressure development can be evaluated by methods well-known in the art, such as left ventriculography, coronary angiography, echocardiography, MRI scans, CT scans, gated myocardial SPEC scans or gated myocardial PET scans.

In some embodiments, a method for increasing inotropic function in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing inotropic function can be evaluated by methods well-known in the art, such as left ventriculography, coronary angiography, echocardiography, MRI scans, CT scans, gated myocardial SPEC scans or gated myocardial PET scans.

In some embodiments, a method for increasing left ventricular ejection fraction (LVEF) in a mammalian cardiac cell or tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. The effects of modified RNA on increasing left ventricular ejection fraction can be evaluated by methods well-known in the art, such as left ventriculography, coronary angiography, echocardiography, MRI scans, CT scans, gated myocardial SPEC scans or gated myocardial PET scans. In some embodiments, the LVEF is increased by between about 4% and 10%. In some embodiments, the LVEF is increased by between about 5% and 8%.

In some embodiments, a method for decreasing one or more biomarkers associated with cardiac dysfunction (e.g., NT-proBNP, BNP, hsTnT and hsTnI) in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium.

In some embodiments, a method for reducing infarct size in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. In some embodiments, the infarct size is reduced. In some embodiments, the infarct is eliminated. The effects of modified RNA on infarct size can be evaluated by methods well-known in the art, such as left ventriculography, coronary angiography, echocardiography, MRI scans, CT scans, gated myocardial SPEC scans or gated myocardial PET scans.

In some embodiments, a method for reducing fibrosis in a mammalian cell, tissue, or subject comprises contacting the mammalian cell, tissue, or subject with a composition comprising the modified RNA in accordance with the present disclosure. In some embodiments, the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium. In some embodiments, the fibrosis is reduced. In some embodiments, the fibrosis is eliminated. The effects of modified RNA on fibrosis can be evaluated by methods well-known in the art, such as left ventriculography, coronary angiography, echocardiography, MRI scans, CT scans, gated myocardial SPEC scans or gated myocardial PET scans.

5.6. Expressing VEGF-A in a Mammalian Cell or Tissue

Another aspect of the present disclosure relates to the administration of a composition or a particular formulation comprising a modified RNA encoding a VEGF-A polypeptide for in vivo, in vitro, in situ, or ex vivo protein expression in a mammalian cell or tissue.

Some embodiments relate to a method for expressing VEGF-A in a mammalian cell or tissue, comprising contacting the mammalian cell or tissue in vivo, in vitro, or ex vivo with a composition comprising the modified RNA.

In some embodiments, a method for expressing VEGF-A in a mammalian cell or tissue comprises contacting the mammalian cell or tissue with a composition comprising the modified RNA in accordance with the present disclosure.

In some embodiments, a method for expressing VEGF-A in a mammalian cell or tissue comprises contacting the mammalian cell or tissue with a composition comprising the modified RNA in accordance with the present disclosure, wherein the composition is formulated in a phosphate-buffered saline buffer, THAM buffer, or citrate saline buffer. In preferred embodiments, compositions comprising the modified RNA comprise a citrate saline buffer. In some embodiments, the citrate saline buffer is substantially free of divalent cations, including calcium and magnesium. In some embodiments, the citrate saline buffer contains no calcium or magnesium.

In some embodiments, a method for expressing VEGF-A in a mammalian cell or tissue comprises contacting the mammalian cell or tissue with a composition comprising the modified RNA in accordance with the present disclosure, wherein the composition comprises a concentration of the modified RNA formulated in citrate saline buffer of between 0.1 and 1 µg/µL. In some embodiments, the composition comprises a concentration of the modified RNA formulated in citrate saline buffer of between 1 and 10 µg/µL. In some embodiments, the composition comprises a concentration of the modified RNA formulated in citrate saline buffer of between 10 and 50 µg/µL.

In some embodiments, a method for expressing VEGF-A in a mammalian cell or tissue comprises contacting the mammalian cell or tissue with a composition comprising the modified RNA in accordance with the present disclosure, wherein the composition is formulated in a lipid-based complex (such as liposomes, lipoplexes, and lipid nanoparticles).

In some embodiments, a method for expressing VEGF-A in a mammalian cell or tissue comprises contacting the mammalian cell or tissue with a composition comprising the modified RNA formulated in citrate saline buffer, wherein the composition is less toxic to the subject than a lipid-based formulation.

5.7. Method of Producing VEGF-A in a Subject

Some embodiments relate to a method of producing VEGF-A in a subject, comprising administering to the subject a composition or a particular formulation comprising the modified RNA in accordance with this disclosure.

As non-limiting examples, in some embodiments, a method of producing VEGF-A in a subject comprises administering to the subject a formulation comprising the modified RNA in accordance with this disclosure. In some embodiments, formulations are formulated in citrate saline buffer. In some embodiments, the formulation further comprises a pharmaceutically acceptable excipient. In some embodiments, the formulation further comprises a pharmaceutically acceptable excipient chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent.

In some embodiments, the formulation further comprises a pharmaceutically acceptable excipient selected from lipid, lipidoid, liposome, lipid nanoparticle, lipoplex, and mixtures thereof.

In some embodiments, a method of producing VEGF-A in a subject comprises administering to the subject a formulation comprising the modified RNA in accordance with this disclosure, wherein the subject is suffering from a disease responsive to VEGF-A therapy. In some embodiments, the subject is suffering from a disease chosen from heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, and peripheral arterial disease. In some embodiments, the disease is heart failure with reduced or preserved ejection fraction. In some embodiments, the disease is post-MI cardiac dysfunction. In some embodiments, the disease is ischemic heart disease. In some embodiments, the disease is a vascular injury from trauma or surgery. In some embodiments, the disease is a skin ulcer including a diabetic ulcer. In some embodiments, the disease is critical limb ischemia. In some embodiments, the disease is pulmonary hypertension. In some embodiments, the disease is peripheral arterial disease. In some embodiments, the disease is kidney disease. In some embodiments, the disease is a disease involving skin grafting and tissue grafting.

In some embodiments, a method of producing VEGF-A in a subject comprises administering to the subject a formulation comprising the modified RNA in accordance with this disclosure, wherein the formulation is administered to the subject via intramuscular, intradermal, subcutaneous, or intracardiac route, through a portal vein catheter, through a coronary sinus catheter, and/or by direct administration into the area to be treated. In some embodiments, the formulation is administered to the subject intramuscularly. In some embodiments, the formulation is administered to the subject intradermally. In some embodiments, the formulation is administered to the subject subcutaneously. In some embodiments, the formulation is administered to the subject intracardially, preferably in multiple (e.g., two, three, four, five, six, seven, eight, nine, ten, eleven, twelve, thirteen, fourteen, fifteen, sixteen, seventeen, eighteen, nineteen, twenty, or more) administrations at a fixed-dosage. In some embodiments, the formulation is administered to the subject through a portal vein catheter. In some embodiments, the formulation is administered to the subject through a coronary sinus catheter. In some embodiments, the formulation is administered to the subject by direct administration into the area to be treated.

In some embodiments, a method of producing VEGF-A in a subject comprises administering to the subject a formulation comprising the modified RNA in accordance with this disclosure, wherein the formulation comprises a lipid-based complex (such as liposomes, lipoplexes, and lipid nanoparticles), phosphate-buffered saline buffer, THAM buffer, or citrate saline buffer. In preferred embodiments, formulations comprising the modified RNA are formulated in citrate saline buffer. In some embodiments, the citrate saline buffer is substantially free of calcium and magnesium. In some embodiments, the citrate saline buffer contains no calcium or magnesium.

In some embodiments, a method of producing VEGF-A in a subject comprises administering to the subject a formulation comprising the modified RNA in accordance with this disclosure, wherein the formulation comprises a concentration of the modified RNA formulated in citrate saline buffer of between 0.1 and 1 µg/µL. In some embodiments, the formulation comprises a concentration of the modified RNA formulated in citrate saline buffer of between 1 and 10 µg/µL. In some embodiments, the formulation comprises a concentration of the modified RNA formulated in citrate saline buffer of between 10 and 50 µg/µL.

In some embodiments, a method of producing VEGF-A in a subject comprises administering to the subject a formulation comprising the modified RNA in accordance with this disclosure, wherein the formulation comprises a in citrate saline buffer and is less toxic to the subject than a lipid-based formulation.

5.8. Method for Preparing a Formulation

Some embodiments relate to a method for preparing a formulation, comprising combining the modified RNA in accordance with this disclosure with a lipid-based complex (such as liposomes, lipoplexes, and lipid nanoparticles), phosphate-buffered saline buffer, THAM buffer, or citrate saline buffer.

Some embodiments relate to a method for preparing a formulation, comprising combining the modified RNA with citrate saline buffer, wherein the formulation is effective for treating a subject suffering from a disease responsive to VEGF-A therapy; modulating a physiological process in mammalian cell, tissue, or subject; expressing VEGF-A in a mammalian cell or tissue; and/or producing VEGF-A in a subject.

In some embodiments, a method for preparing a formulation comprises combining the modified RNA in accordance with this disclosure with citrate saline buffer, wherein the formulation comprises a concentration of the modified RNA formulated in citrate saline buffer of between 0.1 and 1 μg/μL. In some embodiments, the formulation comprises a concentration of the modified RNA formulated in citrate saline buffer of between 1 and 10 μg/μL. In some embodiments, the formulation comprises a concentration of the modified RNA formulated in citrate saline buffer of between 10 and 50 μg/μL.

In some embodiments, a method for preparing a formulation comprises combining the modified RNA with citrate saline buffer in accordance with this disclosure, wherein the formulation comprises a citrate saline buffer and is less toxic to the subject than a lipid-based formulation.

In some embodiments, a method for preparing a formulation comprises combining the modified RNA with citrate saline buffer in accordance with this disclosure, wherein the citrate saline buffer is substantially free of divalent cations, including calcium and magnesium. In some embodiments, the citrate saline buffer contains no calcium or magnesium.

In some embodiments, a method for preparing a formulation comprises combining the modified RNA with citrate saline buffer in accordance with this disclosure, wherein the formulation comprises a citrate saline buffer and further comprises a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent.

Formulations can be administered to a subject via a number of routes in accordance with this disclosure. Special formulations suitable for intradermal, intracardiac, subcutaneous, and intramuscular injections are known in the art. For example, in order to prolong the effect of an active ingredient, it is often desirable to slow the absorption of the active ingredient from intramuscular injection. Delayed absorption of an intramuscularly administered drug form is accomplished by dissolving or suspending the drug (for example, a modified RNA) in an oil vehicle. Injectable depot forms are made by forming microencapsule matrices of the drug (for example, a modified RNA) in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). For intradermal and subcutaneous injections, the formulations are preferably formulated so that they do not induce an immune response when delivered to the intradermal compartment. Additives may be used in the formulations for intradermal injections include for example, wetting agents, emulsifying agents, or pH buffering agents. The formulations for intradermal injections may also contain one or more other excipients such as saccharides and polyols. For intracardiac injections, the formulations are preferably formulated so that they do not cause additional damages to the heart muscle and coronary arteries after the use of an injection needle. Suitable formulations for intracardiac injection are provided herein.

5.9. Method of Reducing Toxicity of Modified RNA Compositions

Some embodiments relate to a method of reducing toxicity of a modified RNA treatment in a subject, comprising formulating the modified RNA with citrate saline buffer. In some embodiments, the formulation of modified RNA with citrate saline buffer is less toxic to the subject than a lipid-based formulation. In some embodiments, the toxicity of the lipid-based formulation is a dose-dependent toxicity. In some embodiments, the toxicity of the lipid-based formulation is a dose-limiting toxicity.

In some embodiments, a method of reducing toxicity of a treatment in a subject comprises formulating the modified RNA in accordance with this disclosure with citrate saline buffer and further comprises a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent. In some embodiments, the solvent is a non-aqueous solvent.

In some embodiments, a method of reducing toxicity of a treatment in a subject comprises formulating the modified RNA in accordance with this disclosure with citrate saline buffer, wherein the subject is suffering from a disease responsive to VEGF-A therapy. In some embodiments, the subject is suffering from a disease chosen from heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, and peripheral arterial disease. In some embodiments, the disease is heart failure with reduced or preserved ejection fraction. In some embodiments, the disease is post-MI cardiac dysfunction. In some embodiments, the disease is ischemic heart disease. In some embodiments, the disease is a vascular injury from trauma or surgery. In some embodiments, the disease is a skin ulcer including a diabetic ulcer. In some embodiments, the disease is critical limb ischemia. In some embodiments, the disease is pulmonary hypertension. In some embodiments, the disease is peripheral arterial disease. In some embodiments, the disease is peripheral arterial disease. In some embodiments, the disease is kidney disease. In some embodiments, the disease is a disease involving skin grafting and tissue grafting.

5.10. Nucleic Acid Sequences

Some embodiments relate to a nucleic acid sequence comprising an in vitro transcription template for the generation of the modified RNA. In some embodiments, a nucleic acid sequence comprises an in vitro transcription template for the generation of the modified RNA in accordance with this disclosure.

Once a transcription template for the generation of the modified RNA is available, modified RNAs in accordance with this disclosure may be prepared according to any available technique well known in the art, using commercially available starting materials (see, e.g., U.S. Patent Application Publication No. 2015/0051268; U.S. Pat. No. 8,710,200; U.S. Patent Application Publication No. 2013/0259923; all of which are incorporated by reference).

All of the claims in the claim listing are herein incorporated by reference into the specification in their entireties as additional embodiments.

6. EXAMPLES

6.1. Example 1

Transfection of VEGF-A Modified RNA and Production of VEGF-A Protein

For investigating the transfection potential of the VEGF-A modified RNA, 10,000 cells were seeded into 96-well plates in regular culture medium. For preparing conditioned media containing modified RNA-produced VEGF-A, 250,000 human umbilical vein endothelial cells (HUVEC) (Lonza, Basel, Switzerland) were seeded in six-well plates in endothelial growth medium (EGM) medium (Lonza). The next day transfection was undertaken in serum-free endothelial basal medium (EBM) media (Lonza). VEGF A modified RNA (amounts indicated) were mixed with Lipofectamine 2000 (Invitrogen, Carlsbad, Calif., USA) according the manufacturer's instructions and added to the cells. As a transfection control, Lipofectamine 2000 mixed with water was used. After 4 hours the transfection medium was removed and changed to fresh serum-free EBM medium and media was collected at specified time points. Conditioned medium was collected after 24 hours and kept at −80° C. Human VEGF A concentration was measured with ELISA as described below.

The amount of human VEGF-A in the cell culture medium post transfection was measured with a human VEGF-A ELISA kit (Novex, Invitrogen) according to the manufacturer's instructions. Absorbance was read at 450 nm in a SpectraMax reader and the VEGF A concentration in the samples was calculated.

For all transfections of the VEGF-A modified RNA into cells in vitro, lipofectamine 2000 was required. VEGF-A modified RNA could be transfected into multiple human cardiac cell types. A higher dose of modified RNA resulted in production of more VEGF-A protein (FIG. 2A). The protein production from the modified RNA peaked approximately 8 hours after transfection, and then declined (FIG. 2B). In addition, the modified RNA transfection and protein production worked across species and both mouse cardiac fibroblasts and pig endothelial cells could be transfected, which resulted in translation of the VEGF-A protein (FIG. 2C).

6.2. Example 2

Activation of VEGF Receptor 2 Signalling by Recombinant and Modified RNA-Produced VEGF-A One hundred thousand HUVEC were seeded into 12-well plates in EGM medium. The next day, cells were starved for 24 hours in EBM and then exposed to 100 ng/mL VEGF-A, either recombinant (R&D Systems, Minneapolis, Minn., USA) or modified RNA-produced (added as conditioned media) or to media without VEGF-A. Stimulation was terminated after 2, 10 and 20 min and the medium was removed. Total protein was prepared from cultured cells with lysis buffer containing protease and phosphatase inhibitors (Mesoscale Discovery, Rockville, Md., USA). Protein concentrations were measured using the BCA Protein Assay kit (Pierce, Rockford, Ill., USA) according to the manufacturer's protocol.

Fifteen micrograms of protein was loaded on a 4 to 12% Bis-Tris gradient gel and electrophoresis was carried out using MES SDS running buffer (Invitrogen). Fractionated protein was electroblotted onto a polyvinyl difluoride (PVDF) membrane (Invitrogen). Membranes were blocked in 5% BSA in TBS Tween (0.1%) and, subsequently, incubated with primary antibodies at 4° C. overnight. Primary antibodies used were against VEGF Receptor 2 (VEGFR2), phosphorylated VEGFR2 (p-VEGFR2), Akt, phosphorylated Akt (p-Akt), eNOS (all from CellSignaling, Danvers, Mass., USA), and phosphorylated eNOS (p-eNOS, BD Biosciences, Franklin Lakes, N.J., USA). Membranes were incubated with a horseradish peroxidase-labelled secondary antibody (Dako, Glostrup, Denmark) and immunoreactions were detected using the ECL Western blotting substrate (Pierce). Chemiluminescent signals were visualized using a ChemiDoc Touch Imaging System (BioRad, Hercules, Calif., USA).

To verify that the VEGF-A protein produced from the modified RNA was active, conditioned medium from cells transfected with VEGF-A modified RNA was added to cultured cells. This resulted in phosphorylation of the main VEGF-A receptor, VEGF receptor 2, in human endothelial cells (FIG. 3A). In addition, conditioned medium also induced phosphorylation of the downstream signalling pathways eNOS in human endothelial cells (FIG. 3B) and Akt in mouse cardiac fibroblasts (FIG. 3C), respectively.

6.3. Example 3

The Modified RNA Produced VEGF-A Protein is an Active Protein that Stimulated Several Critical Steps in the Angiogenic Process HUVEC were seeded in 96-well plates, at a density of 3000 cells per well, in EGM medium (Lonza). The next day, medium was changed to basal EBM medium supplemented with 2% fetal bovine serum (FBS) and recombinant VEGF-A (R&D Systems) or to conditioned medium containing modified RNA-produced VEGF-A, supplemented with 2% FBS. VEGF-A concentrations were 10 ng/mL, 50 ng/mL and 100 ng/mL, respectively. Medium without VEGF-A was used as control. Plates were kept at 37° C. in 5% $CO_2$ and two days later fixed in 4% buffered formaldehyde (Histolab, Gothenburg, Sweden) and nuclei stained with Hoechst (Invitrogen) for 10 min. Nuclear count was determined in the Image Express High Content Analysis System.

HUVEC were stained with Cell Tracker Red (Molecular Probes, Eugene, Oreg., USA) according to the manufacturer's instruction and seeded in EBM medium supplemented with 2% serum in transwell inserts with a FloroBlok membrane with 8 μm pore size in a 24-well plate (Corning, N.Y., USA). EBM with 2% serum with human recombinant VEGF-A (R&D Systems) or conditioned medium containing modified RNA-produced VEGF-A with 2% serum were added to the lower chamber. VEGF-A as chemoattractant was studied at concentrations of 10 ng/mL and 100 ng/mL, respectively. Medium without VEGF-A was used as control. After 24 hours, cells that had migrated to the lower side of the membrane were counted with the Image Express High Content Analysis System.

HUVEC were mixed with Cytodex 3 microcarrier beads (GE Healthcare, Little Chalfont, United Kingdom) in EBM and tubes were kept at 37° C. and flicked regularly to allow for even coating. After 4 hours, beads coated with endothelial cells were seeded in flasks and kept at 37° C. and 5% $CO_2$ overnight. Beads were suspended at 500 beads/mL in a fibrinogen solution (2 mg/mL, Sigma Aldrich, St. Louis, Mo., USA) containing aprotinin (0.15 Units/mL, Sigma Aldrich), and then added to wells containing thrombin (0.625 Units/mL, Sigma Aldrich) in 96-well plates. After 15 min the fibrin gel had formed a clot and EGM medium with recombinant VEGF-A or conditioned medium containing modified RNA-produced VEGF-A was added. As a control, medium without VEGF-A was used. Plates were kept at 37° C. and 5% $CO_2$ for 2 days when angiogenic sprout formation was evaluated. Cells were stained with calcein for 30 min and plates were read in Image Express High Content Analysis System and sprout formation was determined.

As depicted, several critical steps in the angiogenic process were affected by the modified RNA-produced VEGF-A protein. VEGF-A increased proliferation (FIG. 4A) and migration (FIG. 4B) of cultured human endothelial cells. In addition, angiogenic sprout formation in 3D culture with beads coated with endothelial cells was increased by modified RNA-produced VEGF-A (FIG. 4C and FIG. 5). Importantly, in endothelial cells the modified RNA-produced VEGF-A protein induced similar responses compared to recombinant VEGF-A protein, which shows that the modified RNA-produced VEGF-A retains its properties and ability to affect angiogenesis.

6.4. Example 4

Assessment of β-Galactosidase Protein Following Single Intracardiac Injection of LacZ Modified RNA in the Mouse Male C57Bl/6 mice (10 to 12 weeks old) were anesthetized with isoflurane. The left thoracic region was shaved and sterilized and following intubation the heart was exposed through a left thoracotomy. LacZ modified RNA formulated in citrate/saline (10 mmol/L citrate, 130 mmol/L sodium chloride in Hyclone water, pH adjusted to approximately 7.5 with sodium hydroxide) or Lipofectamine® (RNAiMAX Transfection Reagent, Thermo Fisher Scientific Inc. NY, USA), was injected (50 μL) in the left ventricular free wall from the apex towards the base of the heart. After the injection, the thorax and the skin were closed by suturing and excess air was removed from the thoracic cavity by gentle chest compression. Subsequently, when normal breathing was established the mouse was disconnected from the ventilator and brought back to its home cage. At predefined time points following the cardiac injection, the mouse was anesthetized and the chest opened a second time. The heart was excised and the transfection efficiency and presence of the reporter β-galactosidase enzyme were examined by 5-bromo-4-chloro-3-indolyl-β-D-galactopyranoside (X-gal) staining. X-gal is hydrolyzed by the enzyme yielding an intensely blue insoluble product indicative of the presence of an active β-galactosidase. Briefly, the organ or tissue was rinsed in phosphate buffer and fixated in 4% paraformaldehyde for 15 min and the washed 3 times (20 to 30 min) with 0.1 mmol/L phosphate (pH 7.3) wash buffer containing 2 mmol/L $MgCl_2$, 0.01% sodium deoxycholate and 0.02% Nonidet P40. Subsequently, freshly prepared X-gal solution (phosphate wash buffer containing 5 mmol/L $K_4Fe(CN)_6$, 5 mmol/L $K_3Fe/CN)_6$ and 1 mg/mL X-gal) was added to the specimen which then was wrapped in foil and incubated at 37° C. overnight. The specimen was then washed with phosphate wash buffer 3 times and photographed.

Following a left thoracotomy, anaesthetized mice were given a single intracardiac injection of citrate/saline or LacZ modified RNA. Approximately 24 hours later the mice were sacrificed and hearts excised. The hearts were then subjected to X-gal staining overnight. FIGS. 6B and 6C illustrate efficient, and qualitatively similar, transfection and production of β galactosidase enzyme in the apical area injected with modified RNA formulated in lipofectamine (FIG. 6B) or citrate/saline buffer (FIG. 6C). No staining was observed in hearts injected with citrate/saline only (FIG. 6A).

6.5. Example 5

Assessment of Luciferase Protein Expression Following Intracardiac Injection of Luciferase Modified RNA in Naive Mice Male C57Bl/6 mice (10 to 12 weeks old) were anesthetized with a mix of ketamine (10 mg/kg) and xylazine (3.5 to 4 mg/kg) administered via intraperitoneal injection. The left thoracic region was shaved and sterilized and following intubation the heart was exposed through a left thoracotomy.

The firefly luciferase modified RNA was formulated with the following buffers:
1. PBS buffer (1×PBS, no calcium, no magnesium, pH 7.4)
2. Citrate saline buffer (C/S, 10 mmol/L citrate, 130 mmol/L sodium chloride in Hyclone water, pH 7.0)
3. THAM buffer (tromethamine AKA 2-amino-2-(hydroxymethyl)-1,3-propanediol), 300 mmol/L Tris-HCl, pH 8.0)

A total of 25 μg of luciferase modified RNA was injected (50 μL) in the left ventricular free wall from the apex towards the base of the heart. After the injection, the thorax and the skin were closed by suturing and excess air was removed from the thoracic cavity by gentle chest compression. Post-surgery, the mouse received an intraperitoneal injection atipamezole hydrochloride (1 mg/kg) and a subcutaneous injection of buprenorphine hydrochloride (0.02 mg/kg). Subsequently, when normal breathing was established, the mouse was disconnected from the ventilator and brought back to its home cage.

Following a left thoracotomy, anaesthetized mice were given a single intracardiac injection of buffer only (PBS, C/S or THAM controls) or firefly luciferase modified RNA formulated in PBS, C/S, or THAM buffer. The hearts were excised for luciferase protein expression assessment via bioluminescence IVIS imaging. The results presented below are the combination of two staggered mouse studies. Table 2 reports the individual raw IVIS bioluminescence flux values and FIG. 7 illustrates the graphed average values for all treatment groups, respectively.

TABLE 2

Raw IVIS bioluminescence data in mice hearts injected with control buffers only or luciferase modified RNA formulated in any of the buffers.

| | Average Flux | n | #1 | #2 | #3 | #4 |
|---|---|---|---|---|---|---|
| C/S | 6.24E+03 | 2 | 5.05E+03 | 7.42E+03 | | |
| C/S + Luc | 6.43E+06 | 3 | 2.26E+06 | 1.41E+05 | 1.69E+07 | |
| THAM | 5.32E+03 | 2 | 4.03E+03 | 6.61E+03 | | |
| THAM + Luc | 3.62E+06 | 3 | 1.82E+06 | 2.93E+06 | 6.10E+06 | |
| PBS | 1.02E+04 | 2 | 2.39E+03 | 1.79E+04 | | |
| PBS + Luc | 1.01E+07 | 3 | 7.84E+06 | 3.14E+06 | 1.94E+07 | |
| C/S + Luc | 4.91E+06 | 3 | 2.49E+06 | 1.93E+06 | 1.03E+07 | |

As depicted in FIG. 7, luciferase protein expression was detected in all hearts injected with luciferase modified RNA, whereas the negative controls (PBS, C/S and THAM) show little to no signal. Baseline IVIS bioluminescent signal in these controls fluctuates from ~4 to 7.5+E03 units bioluminescent flux, expressed as photons/second. A 3 to 4 order of magnitude in luciferase signal was detected in all hearts injected with luciferase modified RNA. No statistical difference was detected between the various buffers.

6.6. Example 6

Assessment of Human VEGF-A Protein Production Following Intracardiac Injection of Human VEGF-A Modified RNA in the Rat Male Sprague Dawley rats (body weight 250 to 300 g) were anesthetized with isoflurane and subcutaneously injected with marcaine (25 mg/kg) and buprenorphine (0.05 mg/kg) for analgesia. The left thoracic region was shaved and sterilized and following intubation the heart was exposed through a left thoracotomy at the fifth intercostal space. Human VEGF-A modified RNA (1800, 150 or 15 µg) formulated in citrate saline (10 mmol/L citrate, 130 mmol/L sodium chloride in Hyclone water, pH adjusted to approximately 7.5 with sodium hydroxide) was injected as six separate injections (15 µL each, total volume 90 µL) along a line in the left ventricular free wall. After the injection, the thorax and the skin were closed by suturing and excess air was removed from the thoracic cavity by gentle chest compression. Subsequently, when normal breathing was established the rat was disconnected from the ventilator and brought back to its home cage. At predefined time points following the cardiac injection, the rat was anesthetized and the chest opened a second time for heart tissue sampling. The heart was excised and the right ventricle and the left and the right atria trimmed off. A transverse slice including the injection sites was excised, divided in two parts that were snap frozen in liquid nitrogen and stored at −80° C. until analysis of VEGF-A protein. A separate tissue sample was taken from the apex remote from the injections site as a negative control.

Anaesthetized rats were intracardially injected with 3 different doses (15, 150 or 1800 µg) of VEGF-A modified RNA formulated in citrate/saline. Each dose was administered as six separate injections across the left ventricular free wall at one single time point. The animals were sacrificed at different time points following the injections, the hearts were excised and ventricular tissue harvested for VEGF-A protein content analysis. FIG. 8A summarizes the time profiles and the magnitude of VEGF-A protein produced for each of the three doses injected. As can be seen the protein production was not dose linear and a 10-fold increase in dose from 15 to 150 µg gave rise to a 1.6-fold increase in the area under the curve (AUC) only, and a similar AUC was observed for the 150 and 1800 µg dose groups (1.1-fold difference).

6.7. Example 7

Effects on of Left Ventricular Function and Infarct Size Following Intracardiac Injection of Human VEGF-A Modified RNA in Rats Subjected to Myocardial Infarction Male Sprague Dawley rats (body weight 250 to 300 g) were anesthetized, pretreated and thoracotomized as described above. The animals were subsequently subjected to permanent ligation of the left anterior descending coronary artery to induce myocardial infarction. The ligation was followed by intracardiac injection of 90 µL of either citrate/saline (10 mmol/L citrate, 130 mmol/L sodium chloride in Hyclone water, pH adjusted to approximately 7.5 with sodium hydroxide), or 150 or 1800 µg human VEGF-A modified RNA formulated in citrate/saline. The entire volume was delivered as six separate epicardial injections along the border zone of the infarct. After the injections, the thorax and the skin were closed by suturing and excess air was removed from the thoracic cavity by gentle chest compression. Subsequently, when normal breathing was established the rat was disconnected from the ventilator and brought back to its home cage.

One and eight days after the procedure the animals were brought to the imaging facilities for assessment of left ventricular function and infarct size via magnetic resonance imaging (MRI). Furthermore, the day after the procedure a blood sample was drawn from the tail vein for analysis of cardiac troponin I (i-STAT® cardiac troponin I diagnostic test, Abbott Point of Care Inc., Abbott Park, Ill. 60064, USA) as a biomarker for cardiac damage. The MRI scanning was undertaken using a dedicated small animal MRI system at a field strength of 4.7 T. The images were acquired in the short-axis orientation, and stacks of images covering the left ventricle were acquired. Electrocardiography was used for triggering imaging at specific phases in the cardiac cycle. Cardiac function was evaluated from an image series demonstrating the movement of the left ventricular wall during one heartbeat. The imaging sequence used when acquiring the image series was a gradient-echo sequence with a transversal repetition time of 10 ms and a flip angle of 25. The volume of the left ventricle was assessed via manual delineation at different time points by an experienced reader using dedicated image analysis software. The end-systolic (ESV) and end-diastolic (EDV) volumes were identified as the smallest and the largest left ventricular volumes. The ejection fraction (EF), reflecting cardiac function, was assessed via the formula $EF=(EDV-ESV)/EDV$. Images demonstrating the extent of a cardiac infarct were acquired after administration of Gadodiamide, a contrast agent containing Gadolinium. Ten min prior to image acquisition 0.3 mmol/kg Gadodiamide was injected via a tail-vein catheter. Imaging was performed using a gradient-echo sequence, where contrast preparation included the use of an inversion pulse. The repetition time was minimum 900 ms, and the flip angle was 90. The volumes of the left ventricular wall (LVV) and of the infarct (IV) were assessed by an experienced reader via manual delineation using dedicated image analysis software. The infarct size (IS), expressed as the infarcted fraction of the left ventricular wall, was determined via the formula $IS=IV/LVV$.

Figure 8C:
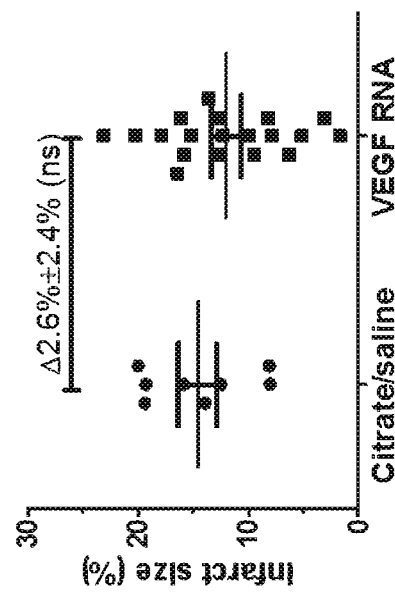

Twenty seven rats were subjected to permanent ligation of the left anterior descending coronary artery and intracardiac injections of citrate/saline (n=8) or a low (150 µg, n=9) or high (1800 µg, n=10) dose of VEGF-A modified RNA formulated in citrate/saline. The animals were followed for 8 days and effects on left ventricular ejection fraction and infarct size were assessed by MRI at day 1 and day 8 following the induction of the infarction. Cardiac TnI was measured in venous blood at day 1 as a biomarker of cardiomyocyte injury. As the two doses of VEGF-A modified RNA gave rise to similar amounts of VEGF-A produced, data from both groups were pooled in the efficacy analysis. As compared to the citrate/saline-treated rats, the animals administered VEGF-A modified RNA had a significantly higher left ventricular ejection fraction day 8 (FIG. 8B) and lower levels of cardiac TnI day 1 (FIG. 8D). Furthermore, the actively treated rats tended to have reduced infarct size vs the vehicle-treated rats (FIG. 8C).

6.8. Example 8

Assessment of β-Galactosidase and Human VEGF-A Protein Following Intracardiac Injection of LacZ Modified RNA or Human VEGF-A Modified RNA in Göttingen Mini Pigs Female Göttingen mini pigs (body weight ~25 kg) fasted overnight were sedated through an intramuscular injection of midazolam and ketamine. Following sedation, an intravenous line was placed in the auricular marginal vein for induction of anaesthesia by propofol and the pig was endotracheally intubated. The pig was then transferred to the laboratory and connected to a ventilator. General anesthesia was maintained by isoflurane delivered through a precision vaporizer and a circle absorption breathing system with periodic arterial blood gas monitoring. Vital signs (heart rate, blood pressure, respiration rate, $O_2$ pulse oxymeter, ECG and body temperature) were continuously monitored throughout the experiment. Intravenous fluid therapy was given throughout the procedure with the rate adjusted to replace blood loss or in case of low systemic blood pressure. A left thoracotomy to expose the heart was carried out and LacZ modified RNA or VEGF-A modified RNA (at varying volumes and doses) was injected in the left ventricular free wall at a depth approximately 5 mm from the epicardial surface. The injection site was marked with a small suture and 6 hours later the heart was excised. Transmural tissue slabs were harvested at the injection sites and X-gal stained for β-galactosidase as described above. For VEGF-A protein analysis, each tissue slab was divided in 6 separate specimens from epicardium to endocardium. These specimens were snap frozen in liquid nitrogen and stored at −80° C. until VEGF-A analysis as described below.

LacZ or VEGF-A modified RNA was epicardially injected in the left ventricular free wall and tissue sampled 6 hrs later for X-gal staining or VEGF-A protein analysis. In pigs administered LacZ modified RNA, the production of β-galactosidase was qualitatively similar when lipofectamine was used as transfection medium (FIG. 9A) as when citrate/saline was used (FIG. 9B).

6.9. Example 9

Quantification of Human VEGF-A Protein in Cardiac Tissue

Tris lysis buffer containing phosphatase inhibitors I and II and protease inhibitor (Meso Scale Discovery (MSD), Rockville, Md., USA) was added to the frozen tissue biopsies and frozen at approximately −20° C. prior to homogenization. Ceramic beads (3 mm) were then added and the samples homogenized using the Precellys homogenizer instrument. The homogenates were centrifuged and the supernatants stored at −80° C. prior to analysis.

VEGF-A concentrations were determined using a sandwich immunoassay with electrochemical luminescent detection. MSD V-PLEX cytokine Panel 1 (human) VEGF-A kits were used to measure the VEGF-A concentration in the tissue homogenates. The assay was performed as per the kit instructions. Standards were serially diluted 1 in 2 with the kit diluent and additional controls were included within each batch to monitor assay performance. Samples were diluted a minimum of 1 in 10 with the kit diluent prior to analysis and the plates read on the MSD Sector 600 instrument.

FIG. 10 summarizes the dose-dependent production of VEGF-A at 6 hours following epicardial injections of varying doses (50 to 2000 µg per injection) of VEGF-A modified RNA formulated in citrate/saline. The levels of protein produced indicate saturation at low doses of injected VEGF-A modified RNA, which is in line with the findings in the rat (FIG. 8A).

6.10. Example 10

LacZ and Luciferase Modified RNA Cardiac Transfection and Translation in a Citrate Saline Buffer As depicted, 75 µg of LacZ encoding modified RNA with cardiac injections was transfected and translated in approximately 10% of the left ventricle (FIGS. 11A, 11B, 11C, and 11D). RNA in situ hybridization for luciferase modified RNA revealed staining expression in the myocardium at the site of injection (FIGS. 11E and 11F) and correlative luciferase protein expression shown via immunohistochemical analysis in the serial section (FIG. 11G).

6.11. Example 11

VEGF-A Protein Expression after Modified RNA Injection to the Heart with Citrate Saline Buffer is Saturable and has Similar Pharmacokinetics Across Multiple Species To compare VEGF-A protein production, 150 µg of VEGF-A modified RNA in a citrate saline buffer and 100 µg of VEGF-A modified RNA using RNAiMax (a lipid-based formulation) as the delivery carrier were injected into a rat heart. After 24 hours, VEGF-A protein levels in the rats with the citrate saline buffer (NTB) was at a comparable level to rats injected with RNAiMax and the pharmacokinetic profile were similar (FIG. 12A). The protein expression was dose limited and saturable, which was seen across species (FIG. 12B). With a ten-fold increase in dose, there was only a 1.6-fold increase in the area under the curve (FIG. 12C).

6.12. Example 12

Assessment of Human VEGF-A Protein Production Following Intracardiac Injection of Human VEGF-A Modified RNA in the Mouse, Rat and Pig To compare VEGF-A protein production, 150 µg of VEGF-A modified RNA in a citrate saline buffer and 100 µg of VEGF-A modified RNA using RNAiMax (a lipid-based formulation) as the delivery carrier were injected into a rat heart. After 24 hours, VEGF-A protein levels in the rats with Male C57Bl/6 mice (10 to 12 weeks old) were anesthetized with isoflurane. The left thoracic region was shaved and sterilized and following intubation the heart was exposed through a left thoracotomy. One hundred µg VEGF-A modified RNA (encoding the human VEGF-A protein (VEGF-A)) formulated in citrate saline (10 mmol/L citrate, 130 mmol/L sodium chloride in Hyclone water, pH adjusted to approximately 7.5 with sodium hydroxide) was injected (50 µL) in the left ventricular free wall from the apex towards the base of the heart. After the injection, the thorax and the skin were closed by suturing and excess air was removed from the thoracic cavity by gentle chest compression. Subsequently, when normal breathing was established the mouse was removed from the ventilator and brought back to its home cage. At predefined time points following the cardiac injection, the mouse was anesthetized and the chest opened a second time for heart tissue sampling. The heart was excised and the right ventricle and the left and the right atria trimmed off. The remaining cardiac tissue (i.e., the left ventricular free wall and the intraventricular septum) was snap frozen in liquid nitrogen and stored at −80° C. until analysis of VEGF-A protein as described below.

Male Sprague Dawley rats (body weight 250 to 300 g) were anesthetized with isoflurane and subcutaneously injected with marcaine (25 mg/kg) and buprenorphine (0.05 mg/kg) for analgesia. The left thoracic region was shaved and sterilized and following intubation the heart was exposed through a left thoracotomy at the fifth intercostal space. Human VEGF-A modified RNA (100 µg) formulated in citrate saline (10 mmol/L citrate, 130 mmol/L sodium chloride in Hyclone water, pH adjusted to approximately 7.5 with sodium hydroxide) was injected as three separate injections (20 µL each, total volume 60 µL) along a line in the left ventricular free wall. After the injection, the thorax and the skin were closed by suturing and excess air was removed from the thoracic cavity by gentle chest compression. Subsequently, when normal breathing was established the rat was disconnected from the ventilator and brought back to its home cage. At predefined time points following the cardiac injection, the rat was anesthetized and the chest opened a second time for heart tissue sampling. The heart was excised and the right ventricle and the left and the right atria trimmed off. A transverse slice including the injection sites was excised, divided in two parts that were snap frozen in liquid nitrogen and stored at −80° C. until analysis of VEGF-A protein as described below.

Female Göttingen mini pigs (body weight ~25 kg) fasted overnight were sedated through an intramuscular injection of midazolam and ketamine. Following sedation, an intravenous line was placed in the auricular marginal vein for induction of anaesthesia by propofol and the pig was endotracheally intubated. The pig was then transferred to the laboratory and connected to a ventilator. General anesthesia was maintained by isoflurane delivered through a precision vaporizer and a circle absorption breathing system with periodic arterial blood gas monitoring. Vital signs (heart rate, blood pressure, respiration rate, $O_2$ pulse oxymeter, ECG and body temperature) were continuously monitored throughout the experiment. Intravenous fluid therapy was given throughout the procedure with the rate adjusted to replace blood loss or in case of low systemic blood pressure. A left thoracotomy to expose the heart was carried out and VEGF-A modified RNA (100 µg formulated in citrate saline (10 mmol/L citrate, 130 mmol/L sodium chloride in Hyclone water, pH adjusted to approximately 7.5 with sodium hydroxide) was injected in the left ventricular free wall at a depth approximately 5 mm from the epicardial surface. The injection site was marked with a small suture and 6 hours later the heart was excised. Transmural tissue slabs were harvested. For VEGF-A protein analysis, each tissue slab was divided in 6 separate specimens from epicardium to endocardium. These specimens were snap frozen in liquid nitrogen and stored at −80° C. until VEGF-A analysis as described below.

As illustrated in FIGS. 13 A and 13B, the amount of protein produced peaked approximately at 6 to 12 hours after injection and the magnitude of and the time profiles for VEGF A protein produced were similar across species. Human VEGF-A protein was still observed in cardiac tissue 192 hours after the injection in the rat (FIG. 13B).

6.13. Example 13

Effects on of Left Ventricular Function and Infarct Size Following Intracardiac Injection of Human VEGF-A Modified RNA in Pigs Subjected to Myocardial Infarction Thirty four sexually mature Lanyu mini-pigs (~5 months old) of either sex were fasted overnight and anaesthetised, endotracheally intubated and artificially ventilated through a respirator with a mixture of oxygen, air and isoflurane. Vital signs (heart rate, blood pressure, respiration rate, $O_2$ pulse oxymeter, ECG and body temperature) were continuously monitored throughout the experiment. Intravenous fluid therapy was given throughout the procedure with the rate adjusted to replace blood loss or in case of low systemic blood pressure. A left thoracotomy to expose the heart was carried out and a permanent occlusion of the mid-left anterior descending coronary artery was undertaken in all pigs except in 5 in which the artery was not occluded (sham group). Subsequently, the chest was closed and the pig transitioned to an intensive care unit for approximately 2 hours after it was brought back to its pen to. Before and after the surgery, analgesics and antibiotics were administered to relieve pain and prevent infection.

Seven days after the initial surgery, the pigs were prepared for a second surgery as described above and brought back to the operating theater. After the preparation, the infarcted pigs were randomised to a blinded treatment with citrate/saline (n=8), VEGF-A modified RNA low dose (1 mg, n=8), VEGF-A modified RNA high dose (10 mg, n=8) or recombinant human VEGF-A protein formulated in self-assembling nanofibers (n=5). Although not approved for clinical use the nanofiber construct was included as a positive control therapy (Lin Y. D. et al., Science Transl Med, (2012) 4:146ra109; its entirety is incorporated herein by reference). Following a left thoracotomy, the study drugs were administered as 20 epicardial injections distributed in the peri-infarct/infarct area, each injection volume being 100 µL. After the procedure, the pigs were treated as described above and left to recover for 2 months before the terminal experiments were carried out.

Throughout the study serial measurements of left ventricular function was assessed by means of echocardiography. Hence, measurements were undertaken under anesthesia in the closed-chest pigs immediately before and after induction of myocardial infarction, immediately before the intracardiac injection of the study drugs and on the day of sacrifice. Cardiac function was assessed by 2D echocardiography using Vivid Q with a 3.5 MHz probe (GE Healthcare, Horten, Norway). The pigs were placed in the left lateral decubitus position. Parasternal long-axis views were obtained by M mode to measure left ventricular volumes to derive left ventricular ejection fraction. At study end (i.e., 2 months after the study drug administration) the pigs were anaesthetised as described above and instrumented for an invasive hemodynamic assessment by means of a pressure-volume loop recording catheter (Millar Instruments, Houston, Tex., USA) positioned in the left ventricular cavity via right carotid artery catheterization. The hemodynamic data were analyzed with a commercial software (AD Instruments). After the hemodynamic assessment, the pig was sacrificed and the heart harvested. The heart was washed three times and processed into five slices from apex to the papillary muscle level. Images were taken of each slice and the infarct sizes were estimated using a commercial software (ImageJ). Infarct size was calculated as a percentage of the area of the whole ventricle minus the area of the inner space.

Serial assessments of left ventricular ejection fraction (EF) were carried out during the course of the study. As can be seen in FIG. 14, the permanent occlusion of the left anterior descending coronary artery was associated with an immediate reduction in EF from approximately 65% to below 45%, a decline that remained 7 days after the occlusion when the study drugs were injected. No such reduction was seen in the pigs subjected to the sham procedure. Two months after the injections, pigs administered with VEGF-A modified RNA or recombinant VEGF-A protein formulated in self-assembling nanofibers were observed to have an improved EF vs the citrate/saline-injected pigs. When comparing the changes in EF from the day of injection until study end, a statistically significant improvement was seen for both VEGF-A modified RNA groups and the VEGF-A protein group but not for the citrate/saline group. The invasive hemodynamic assessment of left ventricular function carried out at study termination showed similar improvement as evidenced by the differences in maximal left ventricular pressure development over time (dP/dt max, FIG. 15), minimal pressure development over time (dP/dt min, FIG. 16), endsystolic pressure volume relationship (ESPVR, FIG. 17), enddiastolic pressure volume relationship (EDPVR, FIG. 18) and preload recruitable stroke work (PRSW, FIG. 19), respectively.

Infarct size was measured after tissue harvesting at study end and was quantified as global left ventricular infarct size (slices 2, 3, 4 and 5, FIG. 20A), mid left ventricular infarct size (slices 3 and 4, FIG. 20B) and mid-most left ventricular infarct size (slice 4, FIG. 20C). As can be seen in FIGS. 20A, 20B and 20C, the VEGF-A modified RNA as well as the VEGF-A protein/nanofiber treatment were associated with a dose-dependent reduction in infarct size vs the citrate/saline-treated pigs.

6.14. Example 14

In Vivo Effect of Human VEGF-A Modified RNA in a Wound Healing Model in Diabetic Mice The purpose of this experiment was to determine if human VEGF-A modified RNA exhibits bioactivity in a diabetic mouse model of delayed cutaneous wound healing. Two trials were performed using the db/db mouse, which has a deficiency in leptin receptor expression due to a point mutation and experiences delayed cutaneous wound healing relative to healthy control mice. The db/db mouse has been widely used in the published literature to test therapeutic efficacy of various treatments aimed at accelerating wound healing. The first trial, Trial 1, included 32 male db/db mice and was designed to: 1) evaluate the effect of human VEGF-A modified RNA on wound healing rates, 2) determine if the treatment caused abnormalities in granulation tissue formation, and 3) determine the effect of human VEGF-A modified RNA on vascularity in the granulation tissue. The second trial, Trial 2, included 7 male db/db mice, and was designed to evaluate oxygenation of the wound over time using ratiometric imaging of a novel boron-based oxygen-sensing nanoparticle. Briefly, on the first day of the trial (Day 0), 1 cm diameter full-thickness cutaneous wounds were surgically made on the dorsum of each mouse, and human VEGF-A modified RNA or vehicle control (n=8 mice per group) was immediately injected intradermally in the perimeter of the wound. In a sub-set of mice (n=8 mice per group), either human VEGF-A modified RNA or vehicle control was also delivered on Day 3. The wounds were bandaged using Tegaderm, and mice were housed individually in cages. Serial photographs of the wounds were acquired at subsequent timepoints, and at the terminal endpoint (Day 18), wound tissues were harvested and processed for immunohistochemistry (CD31+ staining for endothelial cells and hematoxylin and eosin (H&E) staining). In Trial 2, serial images of fluorescence and phosphorescence were acquired after delivering the oxygen-sensing nanoparticles topically to the wound bed after an experimental procedure similar to Trial 1 except that only dosing at day 0 and 3 was done. The results from Trial 1 showed that the sequential dosing of human VEGF-A modified RNA (100 μg on Day 0 and 100 μg on Day 3) significantly (p<0.05) decreased the open wound area at day 6 and day 10, relative to sequential dosing of vehicle control while single dosing of either human VEGF-A modified RNA or vehicle control did not. The average percent of wound closure between early time points (day 3 to 6) was significantly increased compared to vehicle control. CD31+ staining in the granulation tissue was also increased in mice receiving sequential dosing of human VEGF-A modified RNA. In Trial 2 the oxygen levels in the wounds at Day 6 were also significantly (p<0.05) increased in mice receiving 2 sequential doses of 100 μg of human VEGF-A modified RNA relative to the double-injected vehicle group. This experiment supports that treatment of cutaneous wounds in the dorsum of diabetic mice with sequential dosing of human VEGF-A modified RNA significantly accelerates wound healing during the early, more clinically-relevant phase of wound healing. Accelerated healing is accompanied by increases in vascularization of the granulation tissue and increased oxygenation of the wound bed at early time points.

Test Compound and Formulation

| | |
|---|---|
| Test compound | Human VEGF-A modified RNA (FIG. 1B) (VEGF-A modified RNA as shown in figures accompanying Example 14) |
| Formulation | Citrate/saline (10 mmol/L/130 mmol/L, pH 7.5) |

Test System

| | |
|---|---|
| Justification for selection of test system | db/db mice used are an established model of Type II diabetes and a plethora of reports describe impaired wound healing as compared to wild type mice. Impaired wound healing of db/db mice allow for longer healing window to test drug bioactivity. |
| Strain | B6.BKS(D)-Lepr$^{db}$/J (db/db mice) |
| Sex | Male |
| Total No of animals | 39 (Trial 1: 32 mice, Trial 2: 7 mice) |

Study Design

| | |
|---|---|
| Dose(s) | Trial 1; 25 μg VEGF-A modified RNA per injection site (4 sites total at each injection time point, 100 μg/animal in total). VEGF-A modified RNA concentration 2.5 μg/μL. Trial 1; 10 μL vehicle injections of 10 mmol/L citrate, NaCl 130 mmol/L Trial 2; 50 μL of 1 mg/mL nanoparticle solution for each imaging time point |

| | |
|---|---|
| Volume(s) of administration | 10 µL of VEGF-A modified RNA or vehicle injected intradermally in four locations at the periphery of wound (40 µL total) Approximately 50 µL of nanoparticle solution added at each imaging time point for Trial 2. |
| Route(s) and frequency of administration | Intradermal injection of VEGF-A modified RNA or vehicle at Day 0 and Day 3. Day 0: injected at 0, 90, 180, and 270 degree positions. Day 3: injected at 45, 135, 225, and 315 degree position. No injections past Day 3. Nanoparticle solution applied topically to wound at each imaging time point (0, 3, 6, 10, 13, and 18 days). |
| Duration of treatment | 18 days |
| Number/group | Trial 1; 8 mice per group Trial 2; 3 and 4 mice per group (see below) |
| Number of groups | Trial 1 4 groups Group 1; single vehicle injection (Day 0, n = 8, 1 mouse died before conclusion of study) Group 2; double vehicle injection (Day 0 and 3, n = 8) Group 3; single human VEGF-A modified RNA injection (Day 0, n = 8) Group 4; double human VEGF-A modified RNA injection (Day 0 and 3, n = 8, 1 mouse died before conclusion of study) Trial 2 (with nanoparticles) 2 groups Group 1; double vehicle injection (Day 0 and 3, n = 4) Group 2; double human VEGF-A modified RNA injection (Day 0 and 3, n = 3) |

Experimental Procedures

The experiments were divided into two trials, Trial 1 and Trial 2. Trial 1 focused exclusively on evaluating the bioactivity of the human VEGF-A modified RNA in the context of diabetic wound healing. Trial 2 again tested the bioactivity of the human VEGF-A modified RNA in the same wound healing model, but also employed the use of oxygen-sensitive nanoparticles to determine the oxygenation within the wound bed. Procedures listed below are common to both Trials unless otherwise noted.

Full thickness skin wound (Day 0): Mice were anesthetized with a 2% inhalable isoflurane/oxygen mixture and were then depilated and sterilized prior to surgery. A 1 cm diameter circle was marked on the dorsum of the mouse using a stencil. Skin (including dermis and epidermis) was carefully excised from the outlined area to form the full thickness skin wound. Human VEGF-A modified RNA or vehicle was injected intradermally. An analgesic (buprenorphine, 0.1 mg/kg) was administered following surgery, and the wounds were covered with a Tegaderm dressing and a self-adhering wrap.

Intradermal injections (Days 0 and 3): Ten µL×4 of human VEGF-A modified RNA or vehicle (outlined above) were injected immediately after excision of skin. At Day 0 (day of wounding), human VEGF-A modified RNA or vehicle was injected into the dermal layer of the skin at 0, 90, 180, and 270 degree positions around the perimeter of the wounds. At Day 3, the human VEGF-A modified RNA or vehicle was injected intradermally at 45, 135, 225, and 315 degree positions around the perimeter of the wound to avoid injection in the same location twice.

Imaging procedure (Days 0, 3, 6, 10, 13 and 18): The self-adhering wrap and Tegaderm dressings were removed prior to imaging the wounds. Body masses were recorded each day before imaging (Day 0, 3, 6, 10, 13, and 18). Images were acquired at a fixed distance above the wound with a twelve megapixel camera while mice were anesthetized with a 2% inhalable isoflurane/oxygen mixture. After imaging, the wounds were covered with a new Tegaderm dressing and wrapped with the existing self-adhering wrap (unless nanoparticle imaging was to be performed).

Imaging procedure with oxygen-sensitive nanoparticles (Day 0, 3, 6, 10, 13, and 18): Imaging for oxygen levels was only performed in Trial 2. After imaging as described above, mice were kept anesthetized and placed on a temperature controlled microscope stage with a custom designed imaging platform. M-JPEGs were acquired under UV illumination for each wound consisting of 1) 10 frames (acquired at 3 frames/second) of wound prior to application of boron-based nanoparticles (BNP) and 2) 60 frames (acquired at 3 frames/second) after superfusion of 50 µL of nanoparticle solution within the wound bed. After imaging, the wounds were covered with a new Tegaderm dressing and wrapped with the existing self-adhering wrap.

Wound oxygenation image analysis: Imaging for oxygen levels was only performed in Trial 2. The UV-illuminated wound images (acquired as described above) were analyzed using custom written MATLAB programs. To account for background signal, selected points within the wound bed were analyzed for the red and blue channel intensity prior to the addition of the nanoparticles. These background intensity values were subtracted from red and blue intensity values acquired after the addition of the nanoparticles. The ratio of blue channel intensity to red channel intensity was computed for each pixel to represent the ratio of fluorescence (constant in the presence of BNP) to phosphorescence (quenched in the presence of oxygen). The ratiometric images were then qualitatively displayed using a 256-value color map scaled to the ratio bounds to spatiotemporally resolve fluorescence-to-phosphorescence ratios. To quantify the amount of oxygen within the wound bed, the raw blue and red channel intensity values were used to construct a grayscale image (low oxygen; black pixels, high oxygen; white pixels). The wound bed was selected as the area of interest and quantified the mean gray pixel value was quantified using ImageJ software.

Harvest of tissue, histological sectioning, and staining (Day 18): Mice were euthanized via $CO_2$ asphyxiation and the final image was acquired of the wound. A 1.5 cm×1.5 cm area around the wound center was excised and divided into longitudinal thirds for three separate analyses. One third of the tissue was snap frozen in liquid nitrogen and sent for assessment of downstream VEGF signaling proteins. The middle third of the tissue was fixed in 10% formalin for 1 week and processed for paraffin embedding. Five µm sections were cut and stained with hematoxylin and eosine (H&E) and for CD31 (Santa Cruz Biotechnology, sc-1506, PECAM-1 (M-20)).

Blood glucose measurements (Day 0 and Day 18): Prior to initial wounding at Day 0, all mice were fasted for four hours in paper bedding cages without food. Initial fasted glucose measurements were taken before wounding. While harvesting the blood at Day 18, unfasted glucose measurements were undertaken and a small sample of blood sampled.

Data Analysis

Wound area quantification: time point for Trials 1 and 2. Using ImageJ, the observers traced the perimeter wound and ImageJ calculated the area of the open wound. To account for differences between observers' judgment, the median value of the three wound areas was reported for each wound. Wound areas at each time point were normalized to the initial wound area (Day 0) to account for minor differences in the initial wound sizes. Data was statistically analysed using a repeated measures two-way ANOVA with significance asserted at p<0.05. Cubic spline interpolation of these data was performed to compute the estimated time to 25%, 50%, and 75% closure of the wound, respectively. The average percent healing between time points was calculated by subtracting the percent of wound area remaining from the previous percent of wound area remaining. Data was analysed using a repeated measures two-way ANOVA with significance asserted at p<0.05.

CD31 staining analysis (Trial 1): Histological cross-sections of the wound tissue were immunostained for CD31, and imaged using transmitted light microscopy with a 40× objective. The brown channel (positive CD31 labeling) was thresholded to white and black to remove background and non-specific labelling. The thresholded percent area of CD31 positive staining was calculated for each of the treatment groups with n=3.

Hematoxylin and eosin staining analysis (Trial 1): Paraffin sections from each wound were stained with H&E and imaged using transmitted light microscopy using a 4× objective. Granulation tissue was visually inspected to qualitatively assess the thickness and continuity of the epidermis, cross-sectional area of granulation tissue (width and thickness), and presence or absence of any abnormal tissue structures, such as hemangiomas.

Downstream VEGF signalling analysis (Western blot) (Trial 1): Skin tissue samples were homogenized with RIPA Lysis Buffer (sc-24948, Santa Cruz Biotechnology, Santa Cruz, Calif.), and centrifuged, the protein concentrations of the supernatant was determined by Bradford protein assay (#5000112, Bio-Red, Hercules, Calif.). Total protein 30 µg were loaded on a polyacrylamide gel (#3450124, Bio-Red, Hercules, Calif.) and transferred to membrane (#1620232, Bio-Red, Hercules, Calif.). The membrane was probed with the following antibodies: anti-pAKT antibody (S473, #4060, Cell Signaling, Danvers, Mass.) and anti-AKT antibody (#4691, Cell Signaling Technology, Danvers, Mass.), anti-rabbit IgG secondary antibody (IRDye 800CW, LI-COR biosciences, Lincoln, Nebr.). Quantification of the pAKT and AKT bands was performed using the ImageJ program 29.

Body mass and blood glucose analysis: Body masses and blood glucose levels were statistically analysed using a repeated measures two-way ANOVA with significance asserted at p<0.05.

Oxygen quantification analysis (Trial 2): The mean gray values of the raw nanoparticle images were statistically analysed using a repeated measures two-way ANOVA with significance asserted at p<0.05.

Results

Results from Wound Area Measurements (Trial 1)

The body mass for the db/db mice in all groups included in Trial 1 are shown in FIG. 21. The body masses were similar for all groups at all time points except the single injected vehicle group and single injected VEGF-A modified RNA group for which there was a significant (p<0.05) difference at day 13. This difference is not thought to have an impact on the study results.

Fasted and fed glucose levels in the db/db mice for all groups at day 0 and at day 18 are shown in FIG. 22. All groups were similar except the single injected vehicle group and single injected VEGF-A modified RNA group for which there was a significant (p<0.05) difference of 85 mg/dL at day 0. This difference is not thought to have an impact on the study results.

The results from measurements of the wound area during the 18 days observation time are shown in FIGS. 23-25. In terms of closure of open wound area, the single injected VEGF-A modified RNA group dose at day 0 did not show any significant effect compared to its single injected vehicle equivalent during the 18 days observation time. On the other hand, the group double injected with VEGF-A modified RNA at day 0 and 3 did show a significantly (p<0.05) faster closure at day 6 with 55% open wound area and at day 10 with 27% open wound area compared to the group with double injected vehicle with day 6 open wound area of 71% and day 10 open wound area of 49%, respectively (FIG. 23). Area under curve was for vehicle single injection 962.83, vehicle double injection 998.21, VEGF-A modified RNA single injection 895.12, VEGF-A modified RNA double injection 792.79, respectively. Time to 25% closure were for single injected vehicle 6.2 days, double injected vehicle 5.4 days, single injected VEGF-A modified RNA 5.1 days and double injected VEGF-A modified RNA 4.2 days, respectively (FIG. 24). Time to 50% closure were for single injected vehicle 8.9 days, double injected vehicle 9.8 days, single injected VEGF-A modified RNA 7.8 days and double injected VEGF-A modified RNA 6.3 days, respectively (FIG. 24) Time to 75% closure were for single injected vehicle 12.3 days, double injected vehicle 13.7 days, single injected VEGF-A modified RNA 12.5 days and double injected VEGF-A modified RNA 10.4 days, respectively (FIG. 24) When comparing the average percent of wound closure between time points the double injected VEGF-A modified RNA group showed significant (p<0.05) difference with 40% change between day 3 to 6 compared to double injected vehicle group with 20% change while the single injected VEGF-A modified RNA group did not show significance compared to the single injected vehicle group (FIG. 25).

Results from Histological Evaluation (Trial 1)

Representative results from H&E-stained sections of the wound area at day 18 are shown in FIG. 26. This staining showed normal granulation tissues without any signs of abnormal tissue structures. In FIG. 27 representative CD31 positive stains are shown for the wound area sections after single and double injected vehicle and VEGF-A modified RNA, respectively. The quantification of the endothelial cell-based vessels in the wound area shown in FIG. 28 resulted in an increased thresholded percent area with CD31 positive stains for both single (4.3±4.0, mean±SD) and double (8.4±4.4) injected VEGF-A modified RNA in comparison to single (3.2±0.6) and double (3.2±0.6) injected vehicle, respectively.

Downstream VEGF Signaling Analysis with Western Blot (Trial 1)

The results of the analysis of downstream VEGF signaling at day 18 including AKT and VEGFR2 are shown in FIG. 29 and FIG. 30. These results did not show any ongoing downstream signaling at day 18 (study end).

Results from Measurements with Oxygen Sensing Nanoparticles (Trial 2)

The body mass for the db/db mice included in the two groups, ie double injected vehicle and VEGF-A modified RNA, in Trial 2 are shown as a function of time in FIG. 31. The body masses were similar for all groups at all time points. Fasted and fed glucose levels at day 0 and day 18 respectively in the db/db mice for double injected vehicle and VEGF-A modified RNA in Trial 2 are shown in FIG. 32. The fasted and fed glucose levels were similar in both groups.

In Trial 2, oxygen sensitive nanoparticles were put into the wounds to estimate the oxygenation. In FIG. 33 a schematic of the technology behind the nanoparticle oxygen quantification is shown. At room temperature and after excitation the nanoparticles emit fluorescence captured by a blue channel signal and an oxygen-dependent phosphorescence captured by a red signal channel. When these signals are put together the result is an image of relative oxygenation in the wound. In FIG. 34 representative images for a double injected vehicle mouse and a double injected VEGF-A modified RNA mouse are shown as a function of time. The yellow and red colour is already at day 3 more prominent in the wound area of the double injected VEGF-A modified RNA mouse compared to the double injected vehicle mouse. At day 6 there is a significant ($p<0.05$) increase in the oxygenation for the double injected VEGF-A modified RNA group compared to the double injected vehicle group (FIG. 35).

The results from measurements of the wound area during the 18 days observation time are shown in FIGS. 36-38. The group with double injected VEGF-A modified RNA at day 0 and 3 did show a significantly ($p<0.05$) faster closure at day 6 with 45% open wound area compared to the group with double injected vehicle with 62% open wound area, respectively. Time to 25% closure were for double injected vehicle 3.4 days and double injected VEGF-A modified RNA 3.8 days, respectively. Time to 50% closure were for double injected vehicle 7.1 days and double injected VEGF-A modified RNA 5.6 days, respectively. Time to 75% closure were for double injected vehicle 8.9 days and double injected VEGF-A modified RNA 7.8 days, respectively. When comparing the average percent of wound closure between time points the double injected VEGF-A modified RNA group did show significant ($p<0.05$) difference with 40% change between day 3 to 6 compared to double injected vehicle group with 14% change, respectively.

CONCLUSIONS

Intradermal administration of 100 µg VEGF-A modified RNA divided on 4 injection sites near the wound perimeter on both Day 0 and Day 3 post injury, significantly decreased the open wound area in db/db mice at Day 6 and Day 10 relative to vehicle control.

Intradermal administration of 100 µg VEGF-A modified RNA divided on 4 injection sites near the wound perimeter on both Day 0 and Day 3 post injury, significantly increased the average percent of wound closure between early time points (Day 3 to 6) compared to vehicle control.

Intradermal administration of 100 µg VEGF-A modified RNA divided on 4 injection sites near the wound perimeter on both Day 0 and Day 3 post injury, increases the area of CD31+ immunostaining in histological cross-sections of granulation tissue at Day 18 relative to vehicle control and relative to dosing with VEGF-A modified RNA at the initial time point (Day 0) only.

Intradermal administration of 100 µg VEGF-A modified RNA divided on 4 injection sites near the wound perimeter on both Day 0 and Day 3 post injury significantly increases the amount of oxygen in the wound at Day 6 relative to vehicle control.

6.15. Example 15

Photoacoustic Microscopy of the Effects of Human VEGF-A Modified RNA on Hemodynamics and Neovascularization in the Mouse Ear In Vivo In this experiment, acute and chronic vascular responses to human VEGF-A modified RNA (VEGF-A modified RNA) were monitored in the healthy mouse ear in vivo. The multi-parametric photoacoustic microscopy (PAM) technique was applied to dynamically characterize the effect of VEGF-A modified RNA on the vascular diameter, oxygen saturation of haemoglobin ($sO_2$), blood flow, and neovascularization. Side-by-side and quantitative comparisons of the responses to VEGF-A modified RNA, recombinant human VEGF-A protein, and citrate/saline/vehicle were performed. Furthermore, the dose dependence of the responses was explored by comparing the outcomes induced by high-dose (100 µg/ear) and low-dose (10 µg/ear) VEGF-A modified RNA. The studies showed that VEGF-A modified RNA induced marked upregulation of the local blood flow near the injection site shortly after injection (30 minutes to 6 hours). In addition, significant capillary angiogenesis and neovascularization 7 to 14 days after the injection of high-dose VEGF-A modified RNA, but not in ears injected with low-dose VEGF-A modified RNA, VEGF-A protein or citrate/saline, were noted. Furthermore, VEGF-A modified RNA induced a striking and spatially confined upregulation in the microvascular blood flow downstream of the injection site, which was distinctly different from the highly concentrated response to the human recombinant VEGF-A protein.

The aim of the present study was to dynamically characterize the effect of VEGF-A modified RNA on the vascular diameter, oxygen saturation of haemoglobin ($sO_2$), blood flow, and neovascularization by means of the multi-parametric photoacoustic microscopy (PAM) technique in the healthy mouse ear in vivo.

Compound and Formulation

| | |
|---|---|
| Test compound | Human VEGF-A modified RNA (FIG. 1B) (VEGF-A modified RNA as shown in figures accompanying Example 15) |
| Formulation | Citrate/saline (10 mmol/L/130 mmol/L, pH 6.5) |

The control/reference compound is recombinant human VEGF-A$_{165}$ protein from R&D Systems Inc, 614 McKinley Place Nebr., Minneapolis, Minn. 55413, USA.

Test System

| | |
|---|---|
| Justification for selection of test system | All animal experiments were performed using the multi-parametric PAM (Ning et al 2015). It is heretofore the only available microscopy platform that can dynamically and comprehensively characterize the blood flow, perfusion, oxygen saturation, and neovascularization in vivo, and is thus ideally suited for this study. |
| Strain | C57BL/6 |
| Sex | Female |
| Total No of animals | 12 |

Study Design

| | |
|---|---|
| Dose(s) | Citrate/saline; NA<br>High-dose VEGF-A modified RNA; 100 µg<br>Medium-dose VEGF-A modified RNA; 30 µg<br>Low-dose VEGF-A modified RNA; 10 µg<br>VEGF-A protein; 1 µg |

| | |
|---|---|
| Volume(s) of administration | 10 µL |
| Route(s) and frequency of administration | Intradermal, single injection |
| Duration of treatment | Acute (less than 5 minutes) |
| Number/group | 1 to 3 |
| Number of groups | 5 |
| Individual animal identification No/reference No | Group 1, high-dose (HD) VEGF-A modified RNA injected, 3 mice: HD no. 1, HD no. 2, HD no. 3 |
| | Group 2, low-dose (LD) VEGF-A modified RNA injected, 2 mice: LD no. 1, LD no. 2 |
| | Group 3, medium-dose (MD) VEGF-A modified RNA injected, 1 mouse: MD no.1 |
| | Group 4, VEGF-A protein (P) injected, 3 mice: P no. 1, P no. 2, P no. 3 |
| | Group 5, citrate/saline injected, 3 mice: C/S no. 1, C/S no. 2, C/S no. 3 |

Experimental Procedures

For the mouse ear imaging, which is completely non-invasive, the same mouse can be repeatedly imaged for time-lapse monitoring of the effects of different drugs on the vascular diameter, $sO_2$, blood flow, angiogenesis and neovascularization. A baseline image of the mouse ear was acquired prior to the intradermal injection of the study drugs. Then, the drug-treated ear was monitored for 6 hours to capture the acute vascular responses and reimaged on day 7 to record chronic hemodynamic responses and possible neovascularization. To examine the persistence of the VEGF-A modified RNA-induced vascular remodeling, the mice treated with high-dose VEGF-A modified RNA were further imaged on day 14, 21, and 28, respectively.

The detailed PAM imaging protocol was as follows: The mouse was anaesthetised in a small chamber flooded with 3% isoflurane inhalation gas (typical flow rate 1 to 1.5 L/min, depending on the body weight). Anaesthesia was maintained at 1.5% isoflurane throughout the experiment. Medical-grade air was used as the inhalation gas to maintain the mouse at normal physiological status. Pure oxygen is not suitable, because it elevates the venous blood oxygenation to be higher than the normal physiological level and biases the PAM measurement. Subsequently, the mouse was transferred from the anesthesia chamber to a nearby stereotaxic stage. The body temperature of the mouse was maintained at 37° C. using a heating pad. Following positioning in the stereotaxic stage a layer of ultrasound gel was applied on the surface of the ear to be imaged. Care was taken to avoid trapping of air bubbles inside the gel. Then the ear was placed beneath a tank filled with deionized water and slowly raised until the ultrasound gel gently came in contact with the tank bottom which was covered by a thin membrane of polyethylene. Ointment was applied to the eyes to prevent drying and accidental laser damage. The imaging head was then lowered until the acoustic lens was immersed in the water tank. Any air bubbles trapped under the lens were removed. Hence, vertically from top to bottom the set-up included the acoustic lens, the water tank, the ultrasound gel and the mouse ear. The laser fluence was then checked to make sure it operated within the laser safety standards of the American National Standards Institute (ie, 20 mJ/cm2). Following the image acquisition, the mouse ear was cleaned with deionized water and transported back to its home cage.

Three vascular parameters were simultaneously acquired by multi-parametric PAM (Ning et al., Simultaneous photoacoustic microscopy of microvascular anatomy, oxygen saturation, and blood flow. Opt Lett, 2015, 40:910-913). Vascular anatomy was directly generated by Hilbert-transformation of the PAM-acquired raw photoacoustic signals at each sampling position. Vascular $sO_2$ was acquired with dual-wavelength excitation to distinguish the oxy- and deoxy-hemoglobin via their optical absorption spectra. Blood flow speed was quantified by correlating 100 successive A-lines acquired at 532 nm. The time window for the correlation analysis was set to 10 ms. The time course of the computed correlation coefficient follows a second-order exponential decay and the decay constant, which is linearly proportional to the blood flow speed, was extracted for flow quantification. Further, the average diameter, s02, and blood flow of individual vessels were extracted with the aid of a documented vessel segmentation algorithm (Soetikno et al., Vessel segmentation analysis of ischemic stroke images acquired with photoacoustic microscopy. Proc. SPIE, 2012, 8223:822345). The measurements of different animals within each groups were combined for statistical analysis.

Data Analysis

Results shown are means±SD. To investigate the quantitative differences between citrate/saline, VEGF-A modified RNA, and human recombinant VEGF-A protein treated mice a mixed model for the repeated measurements was used for performing the statistical analysis. An individual intercept model with autoregressive structure of the covariance matrix was fitted to the difference in vessel diameter or volumetric flow from baseline. Additionally, baseline vessel diameter or volumetric flow was used as a covariate to correct for any differences.

Results

The high dose of VEGF-A modified RNA was intradermally injected in the ear of three healthy mice. Representative time-lapse PAM images of vascular structure, $sO_2$ and blood flow are shown in FIG. 39. Shortly (ie, up to 6 hours) after injection, significant upregulation in vascular $sO_2$ and blood flow were observed at the periphery of the injection site in all three mice. PAM images repeatedly acquired on day 7, 14, 21, and 28 showed that the previously upregulated $sO_2$ gradually regressed back, while the blood flow remained above the baseline. Besides the sustained upregulation in blood flow, striking angiogenesis and neovascularization were observed in two out of the three high-dose VEGF-A modified RNA-injected ears (FIG. 40). The strong contrast of these neovessels in the PAM images implies that they were highly perfused with red blood cells. Specifically, as seen in FIG. 40, the neovessels appeared 14 days after the injection, regressed on day 21, and "disappeared" on day 28. Similarly, in the 2nd high-dose mouse, the neovessels showed up on day 7 and "disappeared" 14 days after the injection. The "regression/disappearance" of the neovessels was likely due to the loss of blood perfusion.

To explore whether reduced VEGF-A modified RNA dosage could induce blood flow upregulation and neovascularization, the vascular responses to lower doses of VEGF-A modified RNA (30 µg and 10 µg) were assessed. In one mouse injected with 30 µg VEGF-A modified RNA a less sustained upregulation in $sO_2$ and blood flow was induced, which regressed back to the baseline on day 14. Although capable of producing capillary angiogenesis around the injection site, pronounced neovascularization was not observed. Reducing the VEGF-A modified RNA dosage even lower (to 10 µg) in two mice led to a further compromised vascular response (FIG. 41). Specifically, the acute upregulation in the vascular $sO_2$ and blood flow was slightly weaker and less sustained (regressed back to the baseline on day 7) and no notable neovascularization or angiogenesis was observed. These results further confirm the dose dependence of the vascular responses to VEGF-A modified RNA.

For comparison, the vascular responses to human recombinant VEGF-A protein were studied in three mice (FIG. 42). Similar to the high- and medium-dose VEGF-A modified RNA, the VEGF-A protein induced sustained upregulation in the local s02 and blood flow throughout the 7-day monitoring period. However, only very moderate capillary angiogenesis was observed in two out of the three mice on day 7 and no neovessel was observed in all cases.

Finally, three control experiments were performed to examine the vascular responses to citrate/saline. As shown in FIG. 43, the local $sO_2$ and blood flow were slightly upregulated shortly after the injection, likely due to an increase in interstitial fluid pressure, and returned to the baseline levels by day 7. No angiogenesis, neovascularization, or inflammatory response was observed.

Using vessel segmentation, the vascular responses to high-dose VEGF-A modified RNA, human recombinant VEGF-A protein, and citrate/saline were further quantitatively compared and are illustrated in FIG. 44. Acute and pronounced vasodilation and flow upregulation were observed shortly after the injection of VEGF-A modified RNA and the VEGF-A protein. Moderate responses in vessel diameter and blood flow were also observed in response to citrate/saline injection, likely a consequence of increased interstitial fluid pressure. As a response, the change from baseline (pre-injection) in vessel diameter (a mean over 4 vessels) was compared over time for the treatments and citrate/saline considered as control. The interaction between treatment and time was statistically significant ($p<0.0001$). All treatments differed statistically from each other at 7 days ($p=0.0009$) and VEGF-A modified RNA and human recombinant VEGF-A protein differed from saline at 6 hours ($p=0.004$). A similar analysis was conducted for the change in volumetric flow from baseline (a mean over 4 vessels). The change in volumetric flow was compared over time for the treatments and citrate/saline considered as control. The interaction between treatment and time was statistically significant ($p=0.02$). At day 7, VEGF-A modified RNA and human recombinant VEGF-A protein differed from citrate/saline ($p=0.0015$). Seven days after injection, the vessel diameter and blood flow in the citrate/saline group returned back to the baseline, which was in striking contrast to the sustained vasodilation and flow upregulation in the VEGF-A modified RNA and human recombinant VEGF-A protein groups.

The spatial dependence of the microvascular responses to the localized injection was further explored. To this end, all major vessels with diameters larger than 50 µm was removed using vessel segmentation and subsequently, the remaining micro vessels were divided into microsegments. Then, the microvascular $sO_2$ and blood flow were extended to the tissue level by superposing the values of individual micro segments. The weighting factor in the superposition was defined as the reciprocal of the distance between the centroid of the microsegment and the location of the tissue of interest. Subtracting the tissue-level flow and $sO_2$ maps acquired before the injection of VEGF-A modified RNA (ie, baseline) from that acquired on day 7 showed a striking (ie, ~4 fold) and spatially confined upregulation in the microvascular blood flow downstream of the injection site (FIG. 45) whereas the change in microvascular $sO_2$ was moderate (FIG. 45). In contrast, the VEGF-A protein-induced upregulation in microvascular flow was less pronounced and more concentrated around the injection site (FIG. 46), but the increase in microvascular $sO_2$ was more significant. As expected, the microvascular responses to saline injection was abolished on day 7 (FIG. 47).

Conclusions

Using multi-parametric photoacoustic microscopy and vessel segmentation, the spatiotemporal vascular responses to intradermal injection of VEGF-A modified RNA, human recombinant VEGF-A protein and citrate/saline were monitored and compared. It was demonstrated that VEGF-A modified RNA can induce dose-dependent, pronounced and sustained vasodilation, flow upregulation, capillary angiogenesis, and neovascularization in vivo. Furthermore, VEGF-A modified RNA induced a striking and spatially confined upregulation in the microvascular blood flow downstream of the injection site, which was distinctly different from the highly concentrated response to the human recombinant VEGF-A protein.

6.16. Example 16

Expression and Detection of Human VEGF-A Protein Following Intradermal Injection of VEGF-A Modified RNA in the Rabbit In Vivo In this experiment, the production of VEGF-A protein in rabbit skin after intradermal (id) injections of human VEGF-A modified RNA (VEGF-A modified RNA) formulated in citrate/saline was studied with microdialysis technique.

Two microdialysis probes were inserted id on the left hind leg in each of 4 anaesthetized rabbits. At t=0 hour (h), the recovery time for both microdialysis probes was started. One hour later, 4 injections of VEGF-A modified RNA (50 µL and 50 µg each) were given close to each microdialysis-probe. Protein-containing eluate was collected on ice every h, starting at t=2 h, for up to t=6 h. After the last eluate collection, the area surrounding the injection sites was excised.

Three hours after the injections of VEGF-A modified RNA, detectable levels (218±155, mean±SEM) of human VEGF-A were found in eluates from 3 out of the 8 probes. Correspondingly, at 4 and 5 hours after the injection, VEGF-A protein was detected in the eluate from 5 out of 8 and 5 out of 8 probes, respectively. Despite large variation in the concentrations observed; the protein levels tended to plateau at these time points (369±217 and 360±203 pg/mL, respectively).

It is concluded that human VEGF-A protein can be detected with microdialysis technique in rabbit skin three to five hours after id injection of VEGF-A modified RNA.

Compound and Formulation

| | |
|---|---|
| Test compound | Human VEGF-A modified RNA (FIG. 1B) (VEGF-A modified RNA as shown in figures accompanying Example 16) |
| Formulation | Citrate/saline (10 mmol/L/130 mmol/L, pH 6.5) |

Test System

|  |  |
|---|---|
| Species | Rabbit |
| Sex | Male |
| Total No of animals | 4 |

Study Design

| | |
|---|---|
| Dose(s) | A total of 200 µg VEGF-A modified RNA divided by four injections at each probe-site Microdialysis probes per animal: 2 |
| Volume(s) of administration | Four times 50 µL at each probe-site |
| Route(s) and frequency of administration | Intradermal |
| Duration of treatment | Acute |
| Number/group | 4 |
| Number of groups | 1 |

Experimental Procedures

Anaesthesia and maintenance of homeostasis: New Zealand White (NZW) male rabbits were anaesthetised with ketamine (5 mg/kg, Ketalar®, Pfizer AB, Sollentuna, Sweden) and medetomidine (0.15 mg/kg, Domitor®, Orion Pharma, Espoo, Finland) administered as an intravenous bolus injection followed by a maintenance infusion (11 and 0.33 mg/kg*h), respectively. The rabbits were intubated and artificially ventilated with a mixture of room air and 10% 02 with a Servo ventilator (900 D, Siemens Elema, Solna, Sweden). The respiratory rate was kept constant at 30 cycles/min. Before and during the experiment, the blood gases and pH in arterial blood were measured by a blood gas analyzer (ABL800 Flex, Radiometer, Copenhagen, Denmark) and, if necessary, adjusted to fall within normal physiological ranges for rabbits by adjusting the tidal volume. The rectal temperature was kept between 38 and 39.5° C. by covering the animals and by external heating.

Animal preparation: A percutaneous polyethylene catheter (Venflon 0.8 mm, Viggo, Helsingborg, Sweden) for administration of anaesthetics was inserted into a marginal vein on the left ear. A polyethylene catheter (Intramedic PE-90 Clay Adams, Becton Dickinson, Sparks, Md., USA) was inserted into the right carotid artery for arterial blood pressure recording (by means of a pressure transducer, Peter von Berg Medizintechnik Gmbh, Kirchseeon/Englharting, Germany) and for blood sampling, respectively. Signals from blood pressure measurements were recorded and sampled by using a computer and software (PharmLab V6.6, AstraZeneca R&D Mölndal, Sweden). The fur on the left hind leg was removed with an electric razor.

Microdialysis: Two 100 kDa linear microdialysis probes, named A and B in each experiment, (66 linear catheter & 66 high cut off linear catheter, M Dialysis AB, Hammarby, Stockholm, Sweden) were inserted id on the upper part of the left hind leg of the rabbit according to the instructions provided by the supplier. The microdialysis probes were perfused with 0.5 µL/min physiological saline (9 mg/mL, Fresenius Kabi AG, Bad Homburg, Germany) and the eluate samples were collected on ice in pre-weighed 0.5 mL tubes (Protein LoBind, Eppendorf AG, Hamburg, Germany). Dead space between the dialysis membrane and the collection tube outlet was about 1.5 µL. The volume of each eluate was determined and 2% bovine serum albumin (BSA, A7979, Sigma-Aldrich, St. Louis, Mo., USA) in phosphate buffered saline (PBS pH 7.4, Gibco® by life Technologies™, Paisley, UK) was added at 1:1 conditions. The samples were stored at −80° C. until analyzed.

Experimental protocol: The experimental design is illustrated in FIG. 48A. At t=0 h, the recovery period for both microdialysis probes was started. One hour later (ie, t=1 h), recovery eluate was collected and subsequently 4 injections at the microdialysis-probe sites were carried out as depicted in FIG. 48B. Protein-containing eluate was collected every hour from t=2 h to t=6 h and handled as described above. At study end the animals were terminated by a lethal iv dose of pentobarbital sodium (Allfatal vet, Omnidea AB, Stockholm, Sweden).

Assessment of human VEGF-A protein in microdialysis eluates: The Gyrolab platform was used for determination of expressed human VEGF-A concentrations in microdialysis eluate samples. The Gyrolab uses an affinity flow-through format with microstructure wells (Gyros, Uppsala, Sweden). A Gyrolab bioaffy 1000 CD consisting of 96 microstructure wells containing an affinity capture column with streptavidin coated material (Gyros) was used. First, a biotinylated capture polyclonal antibody against human VEGF A (AF-293-NA, R&D systems, Abingdon, UK) was immobilized on the streptavidin column, where samples are flowed through by rotation gravity and the analyte is captured on the antibodies. An Alexa-labelled detection antibody against human VEGF-A (R&D systems) was then flowed through the column and the florescence intensity was used for quantification of the ligand. A standard curve was created using a five parametric linear fit and the sample concentrations were calculated from the standard curve according to their absorbance. A standard curve ranging from 16.7 pg/mL to 12170 pg/mL was prepared with human VEGF-A165 (293-VE-010, R&D systems) in MSD diluent 9 (Meso Scale Discovery, Rockville, Md., USA). Quality controls were prepared from the WHO standard of human VEGF-A165 (National Institute for Biological Standards and Control, Hertfordshire, UK) in MSD diluent 9. All standard, QCs, and samples were mixed 1:1 with Rexxip HN-max (Gyros) before analysis.

Data Analysis: Results are Presented as Mean±SEM.

Results

The individual human VEGF-A protein levels from the four rabbits (with two inserted probes each, A and B) are presented as mean±SEM in FIG. 49. Three hours after the injections of VEGF-A modified RNA, detectable levels (218±155, mean±SEM) of human VEGF-A were found in eluates from 3 out of the 8 probes. Correspondingly, at 4 and 5 hours after the injection, VEGF-A protein was detected in the eluate from 5 out of 8 and 5 out of 8 probes, respectively. Despite large variation in the concentrations observed, the protein levels tended to plateau at these time points (369±217 and 360±203 pg/mL, respectively).

Conclusion

Human VEGF-A protein, detected with microdialysis technique, is expressed in rabbit skin 3 to 5 hours after intradermal injection of VEGF-A modified RNA.

6.17. Example 17

Effects on Capillary and Arteriole Density and Fibrosis Following Intracardiac Injection of Human VEGF-A Modified RNA in Pigs Subjected to Myocardial Infarction In Vivo The assessments of the effects of VEGF-A modified RNA (1 or 10 mg), citrate/saline (2 mL) or sham procedure on capillary and arteriole density and fibrosis were undertaken in the Lanyu mini-pigs.

Capillary and arteriole density assay: Following study termination, tissue samples from the peri-infarct area were fixed in 4% paraformaldehyde at 4° C. for at least 24 hours and then paraffin embedded. After sectioning, deparaffinization and rehydration, antigen retrieval was performed by boiling in 10 mmol/L sodium citrate buffer (pH 6) for 10 minutes. Sections were then incubated with anti-cardiac troponin I (1:200, DSHB, Iowa, Iowa, USA), anti-isolectin (1:100, Invitrogen, Carlsbad, Calif., USA) and SM-22α (1:200, Abcam, Cambridge, UK) overnight. After washing three times, sections were incubated with the relevant Alexa Fluor 488 or 568 antibodies (Invitrogen). Nuclei were stained with 4',6-diamidino-2-phenylindole (DAPI, Sigma-Aldrich, St. Louis, Mo., USA). After mounting, capillary and arteriole densities were calculated by manually counting and averaging from images (200× magnification) taken at three randomly selected areas along the peri-infarct region.

Fibrosis measurement: Samples remote from the infarct/peri-infarct areas were processed as described above for the peri-infarct area samples. Fibrosis, as a function of collagen deposition, was determined using Masson's trichrome staining. Images from three randomly selected areas were taken using bright field microscopy (200× magnification) for each section and then quantified (AxioVision, Zeiss, Munich Germany) and averaged.

Results

FIG. 50A and FIG. 50B illustrate the effects of sham procedure or injection of VEGF-A modified RNA (1 or 10 mg) or citrate/saline (2 mL) on capillary and arteriole density in the peri-infarct (border) zone assessed two months following induction of myocardial infarction. As seen, the injection of VEGF-A modified RNA was associated with a dose-dependent and statistically significant increase in capillary and arteriole density vs the injection of citrate/saline.

Injection of VEGF-A modified RNA vs citrate/saline was demonstrated to statistically significantly attenuate collagen content (i.e., fibrosis) in tissue samples harvested remote from the infarcted area (FIG. 50C).

6.18. Example 18

Time Course of VEGF-A Protein Production Following Human VEGF-A Modified RNA Transfection In Vitro For investigating the time profile of human VEGF-A protein production following VEGF-A modified RNA transfection, 10,000 human aortic smooth muscle cells (hAoSMC, (Lonza, Bazel, Switzerland) or 20,000 human cardiomyocytes derived from induced-pluripotent cells (hiPS-CM, Cellular Dynamics, Madison, Wis., USA) were seeded into 96-well plates in smooth muscle cell basal medium supplemented with growth factors (SmGM-2, Lonza) or fully supplemented cardiomyocyte maintenance medium (Cellular Dynamics), respectively. The next day transfection was undertaken in serum-free medium and 250 ng VEGF-A modified RNA was mixed with Lipofectamine 2000 (Invitrogen, Carlsbad, Calif., USA) according the manufacturer's instructions and added to the cells. Lipofectamine 2000 mixed with water was used as transfection control. Medium was replaced with fresh medium every 8$^{th}$ hour and human VEGF-A protein was measured in the supernatant with ELISA at different time points.

The magnitude of the human VEGF-A protein produced from the VEGF-A modified RNA peaked at approximately 8 hours post-transfection in both human aortic smooth muscle cells and in human cardiomyocytes and then declined towards low levels (FIG. 51). At 32 hours post transfection, no or very low levels of protein were detected.

6.19. Example 19

Time Course of Epicardium-Derived Cell Expansion Post-Myocardial Infarction in the Mouse Male C57BL/6 mice were anaesthetized with isoflurane, intubated and connected to a ventilator and artificially ventilated with 2.5 to 3% isoflurane supplemented with air and oxygen (80/20%). Rectal temperature was maintained at 37.5° C. by a heated operation table and a heating lamp. Subsequently, the chest was shaved and ECG needle electrodes inserted in the paws for assessment of heart rate and ECG. An incision was made in the skin, the chest muscles carefully separated and the fourth intercostal space opened for chest retractor insertion. The pericardium was gently dissected and a 7-0 silk ligature was placed around the left anterior descending coronary artery just under the left atrium for permanent occlusion. Ischemia was confirmed through visual inspection (paleness of the left ventricle distal from suture) and ST-elevation of the ECG. Control animals were not subjected to artery occlusion. The ribs and skin was then closed with 6-0 absorbable sutures. Analgesic (buprenorphine, 0.05 mg/kg, 10 mL/kg) was given subcutaneously and the mice were allowed to recover in its cage on an electric heating pad. The mice were sacrificed on day 3, day 7 and on day 14 post-myocardial infarction (MI). The hearts were excised and then rinsed in saline before formalin fixation. Epicardium-derived cell (EPDC) activation was assessed by Wilm's tumor protein 1 (Wt-1) expression through immunohistochemistry.

Formalin-fixated hearts were transversely sliced into 1 mm slices from apex to base. The heart slices were dehydrated in ethanol and xylene, embedded in paraffin and finally sectioned into 4 µm slices. Immunohistochemistry for Wt-1 as a marker of EPDC was carried out in a Ventana Discovery XT autostainer using rabbit polyclonal antibodies against Wt-1 (dilution 1:200, Calbiochem, San Diego, Calif., USA). All reagents were Ventana products (Roche, Basel, Switzerland). Wt-1 positive (Wt-1$^+$) cells were evaluated blindly and by means of a manual scoring system. The scores were defined as, 0; no Wt-1$^+$ cells, 1; rare number of Wt-1$^+$ positive cells, 2; few Wt-1$^+$ positive cells in a single layer located at a specific level in the heart, 3; moderate number of Wt-1$^+$ positive cells located at several levels in the heart and 4; extensive number of Wt-1$^+$ positive cells in a thick layer located at several levels in the heart.

Few Wt-1$^+$ EPDCs were found in the epicardium of control, non-infarcted hearts (FIG. 52A). Following induction of MI, the Wt-1$^+$ EPDCs were activated and expanded in number reaching a peak 7 days post-MI (FIG. 52B).

7. SEQUENCE LISTING

7.1. SEQ ID NO: 1: Modified RNA encoding VEGF-A used in the Examples

5'$^{7Me}$G$_{ppp}$G$_{2'OMe}$GGAAAUAAGAGAGAAAAGAAGAGUAAGAAGAAAUAUAAGAGCCACCAUG
AACUUUCUGCUGUCUUGGGUGCAUUGGAGCCUUGCCUUGCUGCUCUACCUCCACCAUGCC
AAGUGGUCCCAGGCUGCACCCAUGGCAGAAGGAGGAGGGCAGAAUCAUCACGAAGUGGUG
AAGUUCAUGGAUGUCUAUCAGCGCAGCUACUGCCAUCCAAUCGAGACCCUGGUGGACAUC
UUCCAGGAGUACCCUGAUGAGAUCGAGUACAUCUUCAAGCCAUCCUGUGUGCCCCUGAUG
CGAUGCGGGGGCUGCUGCAAUGACGAGGGCCUGGAGUGUGUGCCCACUGAGGAGUCCAAC
AUCACCAUGCAGAUUAUGCGGAUCAAACCUCACCAAGGCCAGCACAUAGGAGAGAUGAGC
UUCCUACAGCACAACAAAUGUGAAUGCAGACCAAAGAAAGAUAGAGCAAGACAAGAAAAU
CCCUGUGGGCCUUGCUCAGAGCGGAGAAAGCAUUUGUUUGUACAAGAUCCGCAGACGUGU
AAAUGUUCCUGCAAAAACACAGACUCGCGUUGCAAGGCGAGGCAGCUUGAGUUAAACGAA
CGUACUUGCAGAUGUGACAAGCCGAGGCGGUGAUAAUAGGCUGGAGCCUCGGUGGCCAUG
CUUCUUGCCCCUUGGGCCUCCCCCAGCCCCUCCUCCCCUUCCUGCACCCGUACCCCCGU
GGUCUUUGAAUAAAGUCUGAGUGGGCGGCAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAAAAUCUAG$_{OH}$3' (SEQ ID NO: 1)

Where:
A, C, G & U = AMP, CMP, GMP & N1-methyl-pseudoUMP, respectively
Me = methyl
p = inorganic phosphate

7.1. SEQ ID NO: 2: Amino acid sequence of human VEGF-A isoform VEGF-165

MNFLLSWVHWSLALLLYLHHAKWSQAAPMAEGGGQNHHEVVKFMDVYQRSY
CHPIETLVDIFQEYPDEIEYIFKPSCVPLMRCGGCCNDEGLECVPTEESNITMQIMR
IKPHQGQHIGEMSFLQHNKCECRPKKDRARQENPCGPCSERRKHLFVQDPQTCK
CSCKNTDSRCKARQLELNERTCRCDKPRR (SEQ ID NO: 2)

7.3. Luciferase mRNA Construct
Luciferase mRNA Construct (Examples 5 and 10)

| | |
|---|---|
| Research Target Name | Luciferase |
| Research Polypeptide Name | Firefly luciferase |
| Note: In the following mRNA sequences, A, C, G & U = AMP, CMP, GMP & N1-methyl-pseudoUMP, respectively. | |
| Cap | Cap, vaccinia capping enzyme |
| 5' UTR | GGGAAAUAAGAGAGAAAAGAAGAGUAAGAA GAAAUAUAAGAGCCACC (SEQ ID NO: 3) |
| ORF of mRNA construct (excluding the stop codon) | AUGGAAGAUGCGAAGAACAUCAAGAAGGGAC CUGCCCCGUUUUACCCUUUGGAGGACGGUAC AGCAGGAGAACAGCUCCACAAGGCGAUGAAA CGCUACGCCCUGGUCCCCGGAACGAUUGCGU UUACCGAUGCACAUAUUGGAGGUAGACAUCAC AUACGCAGAAUACUUCGAAAUGUCGGUGAGG CUGGCGGAAGCGAUGAAGAGAUAUGGUCUUA ACACUAAUCACCGCAUCGUGGUGUGUUCGGA GAACUCAUUGCAGUUUUUCAUGCCGGUCCUU GGAGCACUUUUCAUCGGGGUCGCAGUCGCGC CAGCGAACGACAUCUACAAUGAGCGGGAACU CUUGAAUAGCAUGGGAAUCUCCCAGCCGACG GUCGUGUUUGUCUCCAAAAAGGGGCUGCAGA AAAUCCUCAACGUGCAGAAGAAGCUCCCCAU UAUUCAAAAGAUCAUCAUUAUGGAUAGCAAG ACAGAUUACCAAGGGUUCCAGUCGAUGUAUA CCUUUGUGACAUCGCAUUUGCCGCCAGGGUU UAACGAGUAUGACUUCGUCCCCGAGUCAUUU GACAGAGAUAAAACCAUCGCGCUGAUUAUGA AUUCCUCGGGUAGCACCGGUUUUGCCAAAGGG GGUGGCGUUGCCCCACCGCACUGCUUGUGUG CGGUUCUCGCACGCUAGGGAUCCUAUCUUUG GUAAUCAGAUCAUUCCCGACACAGCAAUCCU GUCCGUGGUACCUUUUCAUCACGGUUUUGGC AUGUUCACGACUCUCGGCUAUUUGAUUUGCG GUUUCAGGGUCGUACUUAUGUAUCGGUUCGA GGAAGAACUGUUUUUGAGAUCCUUGCAAGAU UACAAGAUCCAGUCGGCCCUCCUUGUGCCAA CGCUUUUCUCAUUCUUUGCGAAAUCGACACU UAUUGAUAAGUAUGACCUUUCCAAUCUGCAU GAGAUUGCCUCAGGGGGAGCGCCGCUUAGCA AGGAAGUCGGGGAGGCAGUGGCCAAGCGCUU CCACCUUCCCGGAAUUCGGCAGGGAUACGGG CUCACGGAGACAACAUCCGCGAUCCUUAUCA CGCCCGAGGGUGACGAUAAGCCGGGAGCCGU CGGAAAAGUGGUCCCCUUCUUUGAAGCCAAG GUCGUAGACCUCGACACGGGAAAAACCCUCG GAGUGAACCAGAGGGGCGAGCUCUGCGUGAG AGGGCCGAUGAUCAUGUCAGGUUACGUGAAU |

| | 7. SEQUENCE LISTING |
|---|---|
| | AACCCUGAAGCGACGAAUGCGCUGAUCGACA<br>AGGAUGGGUGGUUGCAUUCGGGAGACAUUGC<br>CUAUUGGGAUGAGGAUGAGCACUUCUUUAUC<br>GUAGAUCGACUUAAGAGCUUGAUCAAAUACA<br>AAGGCUAUCAGGUAGCGCCUGCCGAGCUCGA<br>GUCAAUCCUGCUCCAGCACCCCAACAUUUUC<br>GACGCCGGAGUGGCCGGGUUGCCCGAUGACG<br>ACGCGGGUGAGCUGCCAGCGGCCGUGGUAGU<br>CCUCGAACAUGGGAAAACAAUGACCGAAAAG<br>GAGAUCGUGGACUACGUAGCAUCACAAGUGA<br>CGACUGCGAAGAAACUGAGGGGAGGGGUAGU<br>CUUUGUGGACGAGGUCCCGAAAGGCUUGACU<br>GGGAAGCUUGACGCUCGCAAAAUCCGGGAAA<br>UCCUGAUUAAGGCAAAGAAAGGCGGGAAAAU<br>CGCUGUC (SEQ ID NO: 4) |
| 3' UTR | UGAUAAUAGGCUGGAGCCUCGGUGGCCAUGC<br>UUCUUGCCCCUUGGGCCUCCCCCCAGCCCCUC<br>CUCCCCUUCCUGCACCCGUACCCCCGUGGUCU<br>UUGAAUAAAGUCUGAGUGGGCGGC (SEQ ID NO: 5) |
| Corresponding amino acid sequence | MEDAKNIKKGPAPFYPLEDGTAGEQLHKAMKR<br>YALVPGTIAFTDAHIEVDITYAEYFEMSVRLAEA<br>MKRYGLNTNHRIVVCSENSLQFFMPVLGALFIGV<br>AVAPANDIYNERELLNSMGISQPTVVFVSKKGLQ<br>KILNVQKKLPIIQKIIIMDSKTDYQGFQSMYTFVT<br>SHLPPGFNEYDFVPESFDRDKTIALIMNSSGSTGL<br>PKGVALPHRTACVRFSHARDPIFGNQIIPDTAILS<br>VVPFHHGFGMFTTLGYLICGFRVVLMYRFEEELF<br>LRSLQDYKIQSALLVPTLFSFFAKSTLIDKYDLSN<br>LHEIASGGAPLSKEVGEAVAKRFHLPGIRQGYGL<br>TETTSAILITPEGDDKPGAVGKVVPFFEAKVVDL<br>DTGKTLGVNQRGELCVRGPMIMSGYVNNPEAT<br>NALIDKDGWLHSGDIAYWDEDEHFFIVDRLKSLI<br>KYKGYQVAPAELESILLQHPNIFDAGVAGLPDDD<br>AGELPAAVVVLEHGKTMTEKEIVDYVASQVTTA<br>KKLRGGVVFVDEVPKGLTGKLDARKIREILIKAK<br>KGGKIAV (SEQ ID NO: 6) |
| Poly(A) tail | 100 nt |

7.4. LacZ mRNA Construct
LacZ mRNA Construct (Examples 4, 8, and 10)

Note: In the following mRNA sequences, A, C, G & U = AMP, CMP, GMP & N1-methyl-pseudoUMP, respectively.

| | |
|---|---|
| Nucleotide sequence<br>(5' UTR, ORF, 3' UTR) | UCAAGCUUUUGGACCCUCGUACAGAAGCUAA<br>UACGACUCACUAUAGGGAAAUAAGAGAGAAA<br>AGAAGAGUAAGAAGAAAUAUAAGAGCCACCA<br>UGGCCUUGGCUGUCGUCCUGCAAAGAAGAGA<br>UUGGGAAAAUCCUGGAGUUACGCAACUGAAU<br>AGACUCGCCGCACAUCCACCGUUCGCGUCCU<br>GGCGAAAUAGCGAAGAAGCGCGGACCGACAG<br>ACCUUCGCAGCAGCUGCGCUCUCUCAACGGG<br>GAAUGGCGGUUCGCAUGGUUUCCGGCUCCUG<br>AGGCAGUCCCGGAAAGCUGGCUCGAGUGCGA<br>CCUCCCGGAAGCCGAUACGGUGGUGGUGCCG<br>UCAAAUUGGCAAAUGCAUGGAUACGACGCCC<br>CCAUCUACACCAACGUCACUUACCCUAUCACC<br>GUGAAUCCCCAUUCGUCCCGACUGAGAACC<br>CGACUGGAUGCUACAGCCUGACCUUUAACGU<br>GGACGAGUCGUGGCUGCAAGAAGGGCAGACU<br>CGCAUCAUUUUCGACGGAGUCAACUCCGCGU<br>UCCAUCUUUGGUGUAACGGACGGUGGGUGGG<br>AUACGGGCAGGACUCCAGGCUGCCGAGCGAA<br>UUCGACUUGUCAGCCUUCCUGCGCGCCGGCG<br>AAAACCGCCUGGCUGUCAUGGUCCUUAGAUG<br>GUCGGAUGGCUCGUACCUGGAGGAUCAGGAC<br>AUGUGGAGGAUGUCAGGGAUCUUCCGGGAUG<br>UCUCGCUGCUCCACAAGCCAACUACCCAGAU<br>CUCCGACUUUCAUGUGGCCACCCGCUUCAAC<br>GAUGACUUCAGCAGGGCGGUUCUGGAAGCCG<br>AGGUGCAAAUGUGCGGAGAACUGAGGGACUA<br>CCUCCGCGUGACUGUCUCGCUCUGGCAGGGU<br>GAAACCCAAGUGGCUUCAGGCACUGCACCGU<br>UCGGAGGAGAAAUCAUCGACGAACGGGGAGG |

-continued

```
AUACGCCGAUCGCGUCACCCUGCGCCUCAAU
GUGGAAAAUCCGAAACUGUGGUCGGCAGAAA
UCCCUAAUUUGUACCGGGCCGUGGUGGAGCU
GCACACCGCCGACGGAACUCUGAUCGAGGCC
GAGGCAUGCGAUGUGGGAUUCCGCGAGGUCC
GCAUCGAAAAUGGACUGCUUCUGCUUAAUGG
CAAACCGCUGCUCAUCCGCGGAGUGAACAGA
CACGAGCAUCACCCGCUGCACGGUCAGGUCA
UGGAUGAACAGACUAUGGUGCAAGACAUCCU
GCUGAUGAAACAAAACAACUUCAACGCCGUU
CGGUGCUCCCAUUACCCUAAUCACCCGUUGU
GGUAUACCCUUUGCGAUCGGUACGGCCUCUA
CGUGGUGGACGAAGCGAACAUCGAGACUCAC
GGAAUGGUCCCUAUGAACCGCCUCACUGACG
ACCCGAGGUGGCUCCCGGCAAUGUCGGAACG
AGUGACUCGGAUGGUGCAGAGGGACCGCAAC
CAUCCGUCGGUGAUAAUCUGGUCGCUGGGGA
ACGAAUCUGGCCACGGAGCUAACCACGAUGC
GCUGUACCGCUGGAUUAAGUCCGUGGACCCA
AGCCGGCCCGUCCAGUACGAAGGAGGUGGUG
CUGAUACCACUGCAACCGACAUCAUCUGCCC
AAUGUAUGCGCGGGUGGAUGAGGACCAACCU
UUCCCGGCGGUGCCAAAGUGGUCCAUCAAGA
AAUGGCUCUCGCUGCCCGGAGAAACGCGCCC
GCUGAUCCUGUGCGAAUAUGCGCACGCUAUG
GGAAAUUCACUGGGGGGAUUUGCGAAGUACU
GGCAGGCUUUUCGACAGUACCCGAGACUCCA
GGGUGGCUUCGUGUGGGACUGGGUUGACCAG
AGCCUCAUCAAAUACGAUGAAAACGGCAACC
CAUGGUCCGCUACGGCGGAGACUUUGGAGA
CACCCCUAACGAUCGCCAGUUCUGCAUGAAC
GGCCUGGUGUUCGCCGACAGAACUCCGCAUC
CAGCCCUUACUGAGGCUAAGCACCAACAACA
GUUCUUCCAGUUCAGACUGUCGGGGCAAACG
AUCGAAGUGACUUCCGAAUACCUCUUCCGGC
AUUCGGACAACGAGUUGCUGCACUGGAUGGU
CGCCCUGGAUGGAAAGCCCCUCGCCUCCGGA
GAAGUGCCGCUCGACGUGGCGCCGCAGGGAA
AGCAGUUGAUCGAGUUGCCGGAACUGCCACA
GCCCGAGUCAGCAGGACAGCUCUGGCUUACC
GUCAGAGUCGUGCAGCCAAAUGCCACCGCCU
GGUCGGAGGCAGGACAUAUUUCAGCCUGGCA
GCAGUGGCGCCUCGCCGAGAAUCUGAGCGUG
ACCUUGCCAGCAGCCUCACACGCCAUUCCGCA
UCUGACCACGUCCGAAAUGGACUUUUGUAUC
GAACUGGGGAAUAAGCGCUGGCAGUUCAAUC
GGCAAUCAGGCUUCCUGUCCCAGAUGUGGAU
UGGUGACAAGAAGCAGCUCCUGACCCCGCUG
CGCGAUCAGUUCACUCGCGCCCCACUUGACA
ACGACAUUGGCGUGAGCGAGGCCACGCGUAU
CGAUCCAAACGCUUGGGUGGAGCGCUGGAAG
GCGGCUGGCCACUAUCAGGCGGAGGCCGCGC
UCCUGCAGUGUACCGCGGAUACCCUCGCAGA
CGCCGUUCUGAUUACCACGGCGCAUGCCUGG
CAACACCAGGGAAAGACCCUGUUUAUCAGCC
GCAAAACUUACCGGAUCGAUGGCAGCGGCCA
AAUGGCGAUCACUGUGGACGUCGAGGUGGCA
UCAGACACUCCACACCCAGCACGGAUCGGAC
UCAAUUGCCAACUGGCUCAAGUGGCUGAGAG
AGUCAAUUGGCUGGGCCUCGGCCCCCAAGAG
AACUACCCUGAUCGGCUUACUGCCGCAUGCU
UUGACCGGUGGGAUCUGCCUCUGUCGGAUAU
GUACACCCCCUACGUGUUCCCAUCCGAGAAC
GGUCUGAGAUGCGGUACUAGGGAGUUGAACU
ACGGACCGCACCAAUGGAGGGGGACUUUCA
GUUCAACAUCUCAAGAUACAGCCAGCAGCAA
UUGAUGGAAACCUCGCACCGGCAUCUCUUGC
AUGCAGAGGAAGGGACCUGGCUGAACAUCGA
UGGAUUCCACAUGGGAAUUGGUGGGAUGAC
UCCUGGUCCCCUAGCGUGUCCGCGGAACUUC
AGCUGUCCGCCGGCCGGUACCACUACCAGCU
CGUGUGGUGUCAAAAGUGAUAAUAGGCUGGA
GCCUCGGUGGCCAUGCUUCUUGCCCCUUGGG
CCUCCCCCCAGCCCCUCCUCCCCUUCCUGCAC
CCGUACCCCCGUGGUCUUUGAAUAAAGUCUG
AGUGGGCGGCUCUAGA (SEQ ID NO: 7)
```

7. SEQUENCE LISTING

| | |
|---|---|
| ORF amino acid sequence | MALAVVLQRRDWENPGVTQLNRLAAHPPFASW<br>RNSEEARTDRPSQQLRSLNGEWRFAWFPAPEAV<br>PESWLECDLPEADTVVVPSNWQMHGYDAPIYTN<br>VTYPITVNPPFVPTENPTGCYSLTFNVDESWLQE<br>GQTRIIFDGVNSAFHLWCNGRWVGYGQDSRLPS<br>EFDLSAFLRAGENRLAVMVLRWSDGSYLEDQD<br>MWRMSGIFRDVSLLHKPTTQISDFHVATRFNDDF<br>SRAVLEAEVQMCGELRDYLRVTVSLWQGETQV<br>ASGTAPFGGEIIDERGGYADRVTLRLNVENPKLW<br>SAEIPNLYRAVVELHTADGTLIEAEACDVGFREV<br>RIENGLLLLNGKPLLIRGVNRHEHHPLHGQVMD<br>EQTMVQDILLMKQNNFNAVRCSHYPNHPLWYT<br>LCDRYGLYVVDEANIETHGMVPMNRLTDDPRW<br>LPAMSERVTRMVQRDRNHPSVIIWSLGNESGHG<br>ANHDALYRWIKSVDPSRPVQYEGGGADTTATDII<br>CPMYARVDEDQPFPAVPKWSIKKWLSLPGETRP<br>LILCEYAHAMGNSLGGFAKYWQAFRQYPRLQG<br>GFVWDWVDQSLIKYDENGNPWSAYGGDFGDTP<br>NDRQFCMNGLVFADRTPHPALTEAKHQQQFFQF<br>RLSGQTIEVTSEYLFRHSDNELLHWMVALDGKP<br>LASGEVPLDVAPQGKQLIELPELPQPESAGQLWL<br>TVRVVQPNATAWSEAGHISAWQQWRLAENLSV<br>TLPAASHAIPHLTTSEMDFCIELGNKRWQFNRQS<br>GFLSQMWIGDKKQLLTPLRDQFTRAPLDNDIGVS<br>EATRIDPNAWVERWKAAGHYQAEAALLQCTAD<br>TLADAVLITTAHAWQHQGKTLFISRKTYRIDSSG<br>QMAITVDVEVASDTPHPARIGLNCQLAQVAERV<br>NWLGLGPQENYPDRLTAACFDRWDLPLSDMYT<br>PYVFPSENGLRCGTRELNYGPHQWRGDFQFNISR<br>YSQQQLMETSHRHLLHAEEGTWLNIDGFHMGIG<br>GDDSWSPSVSAELQLSAGRYHYQLVWCQK<br>(SEQ ID NO: 8) |
| ORF nucleotide sequence | AUGGCCUUGGCUGUCGUCCUGCAAAGAAGAG<br>AUUGGGAAAAUCCUGGAGUUACGCAACUGAA<br>UAGACUCGCCGCACAUCCACCGUUCGCGUCC<br>UGGCGAAAUAGCGAAGAAGCGCGGACCGACA<br>GACCUUCGCAGCAGCUGCGCUCUCUCAACGG<br>GGAAUGGCGGUUCGCAUGGUUUCCGGCUCCU<br>GAGGCAGUCCCGGAAAGCUGGCUCGAGUGCG<br>ACCUCCCGGAAGCCGAUACGGUGGUGGUGCC<br>GUCAAAUUGGCAAAUGCAUGGAUACGACGCC<br>CCCAUCUACACCAACGUCACUUACCCUAUCAC<br>CGUGAAUCCCCCAUUCGUCCCGACUGAGAAC<br>CCGACUGGAUGCUACAGCCUGACCUUUAACG<br>UGGACGAGUCGUGGCUGCAAGAAGGGCAGAC<br>UCGCAUCAUUUUCGACGGAGUCAACUCCGCG<br>UUCCAUCUUUGGUGUAACGGACGGUGGGUGG<br>GAUACGGGCAGGACUCCAGGCUGCCGAGCGA<br>AUUCGACUUGUCAGCCUUCCUGCGCGCCGGC<br>GAAAACCGCCUGGCUGUCAUGGUCCUUAGAU<br>GGUCGGAUGGCUCGUACCUGGAGGAUCAGGA<br>CAUGUGGAGGAUGUCAGGGAUCUUCCGGGAU<br>GUCUCGCUGCUCCACAAGCCAACUACCCAGA<br>UCUCCGACUUUCAUGUGGCCACCCGCUUCAA<br>CGAUGACUUCAGCAGGGCGGUUCUGGAAGCC<br>GAGGUGCAAAUGUGCGGAGAACUGAGGGACU<br>ACCUCCGCGUGACUGUCUCGCUCUGGCAGGG<br>UGAAACCCAAGUGGCUUCAGGCACUGCACCG<br>UUCGGAGGAGAAAUCAUCGACGAACGGGGAG<br>GAUACGCCGAUCGCGUCACCCUGCGCCUCAA<br>UGUGGAAAAUCCGAAACUGUGGUCGGCAGAA<br>AUCCCUAAUUUGUACCGGGCCGUGGUGGAGC<br>UGCACACCGCCGACGGAACUCUGAUCGAGGC<br>CGAGGCAUGCGAUGUGGGAUUCCGCGAGGUC<br>CGCAUCGAAAAUGGACUGCUUCUGCUUAAUG<br>GCAAACCGCUGCUCAUCCGCGGAGUGAACAG<br>ACACGAGCAUCACCCGCUGCACGGUCAGGUC<br>AUGGAUGAACAGACUAUGGUGCAAGACAUCC<br>UGCUGAUGAAACAAAACAACUUCAACGCCGU<br>UCGGUGCUCCCAUUACCCUAAUCACCCGUUG<br>UGGUAUACCCUUUGCGAUCGGUACGGCCUCU<br>ACGUGGUGGACGAAGCGAACAUCGAGACUCA<br>CGGAAUGGUCCCAUGAACCGCCUCACUGAC<br>GACCCGAGGUGGCUCCCGGCAAUGUCGGAAC<br>GAGUGACUCGCGAUGGUGCAGAGGGACCGCAA<br>CCAUCCGUCGGUGAUAAUCUGGUCGCUGGGG |

7. SEQUENCE LISTING

```
AACGAAUCUGGCCACGGAGCUAACCACGAUG
CGCUGUACCGCUGGAUUAAGUCCGUGGACCC
AAGCCGGCCCGUCCAGUACGAAGGAGGUGGU
GCUGAUACCACUGCAACCGACAUCAUCUGCC
CAAUGUAUGCGCGGGUGGAUGAGGACCAACC
UUUCCCGGCGGUGCCAAAGUGGUCCAUCAAG
AAAUGGCUCUCGCUGCCCGGAGAAACGCGCC
CGCUGAUCCUGUGCGAAUAUGCGCACGCUAU
GGGAAAUUCACUGGGGGGAUUUGCGAAGUAC
UGGCAGGCUUUUCGACAGUACCCGAGACUCC
AGGGUGGCUUCGUGUGGGACUGGGUUGACCA
GAGCCUCAUCAAAUACGAUGAAAACGGCAAC
CCAUGGUCCGCGUACGGCGGAGACUUUGGAG
ACACCCCUAACGAUCGCCAGUUCUGCAUGAA
CGGCCUGGUGUU

```
<222> LOCATION: (1)..(845)
<223> OTHER INFORMATION: A = AMP, C = CMP, G = GMP, U = N1-methyl-
      pseudoUMP
<220> FEATURE:
<221> NAME/KEY: modified_base
<222> LOCATION: (2)..(2)
<223> OTHER INFORMATION: G2'OMe, wherein Me is methyl
<220> FEATURE:
<221> NAME/KEY: modified_base
<222> LOCATION: (845)..(845)
<223> OTHER INFORMATION: GOH 3'

<400> SEQUENCE: 1
ggggaaauaa gagagaaaag aagaguaaga agaaauauaa gagccaccau gaacuuucug     60
cugucuuggg ugcauuggag ccuugccuug cugcucuacc uccaccaugc caagugaucc    120
caggcugcac ccauggcaga aggaggaggg cagaaucauc acgaaguggu gaaguucaug    180
gaugucuauc agcgcagcua cugccaucca aucgagaccc ugguggacau cuuccaggag    240
uacccugaug agaucgagua caucuucaag ccauccugug ugcccgau gcgaugcggg       300 ggcugcugca augacgaggg ccuggagugu ugcccacug aggaguccaa caucaccaug      360
cagauuaugc ggaucaaacc ucaccaaggc cagcacauag gagagaugag cuuccuacag    420
cacaacaaau gugaaugcag accaaagaaa gauagagcaa acaagaaaaa ucccuguggg    480
ccuugcucag agcggagaaa gcauuguuu guacaagauc cgcagacgug uaaauguucc     540
ugcaaaaaca cagacucgcg uugcaaggcg aggcagcuug aguuaaacga acguacuugc    600
agaugugaca agccgaggcg ugauaauag gcuggagccu cgguggccau gcuucuugcc     660
ccuugggccu cccccagcc ccuccucccc uuccugcacc cguaccccg uggucuuuga      720 auaaagucug aguggcggc aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa    840
ucuag                                                                845

<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140
```

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
            165                 170                 175

Leu Glu Leu Asn Glu Arg Thr Cys Arg Cys Asp Lys Pro Arg Arg
        180                 185                 190

<210> SEQ ID NO 3
<211> LENGTH: 47
<212> TYPE: RNA
<213> ORGANISM: Artificial Sequence
<220> FEATURE:
<223> OTHER INFORMATION: Firefly luciferase 5' UTR
<220> FEATURE:
<221> NAME/KEY: misc_feature
<222> LOCATION: (1)..(47)
<223> OTHER INFORMATION: A = AMP, C = CMP, G = GMP, U = N1-methyl-
      pseudoUMP

<400> SEQUENCE: 3
gggaauaaag agagaaaaga agaguaagaa gaaauauaag agccacc          47

<210> SEQ ID NO 4
<211> LENGTH: 1650
<212> TYPE: RNA
<213> ORGANISM: Artificial Sequence
<220> FEATURE:
<223> OTHER INFORMATION: Firefly luciferase ORF of mRNA construct
      (excluding the stop codon)
<220> FEATURE:
<221> NAME/KEY: misc_feature
<222> LOCATION: (1)..(1650)
<223> OTHER INFORMATION: A = AMP, C = CMP, G = GMP, U = N1-methyl-
      pseudoUMP

<400> SEQUENCE: 4
auggaagaug cgaagaacau caagaaggga ccugccccgu uuuacccuuu ggaggacggu    60
acagcaggag aacagcucca caaggcgaug aaacgcuacg cccugguccc cggaacgauu   120
gcguuuaccg augcacauau ugagguagac aucacauacg cagaauacuu cgaaaugucg   180
gugaggcugg cggaagcgau gaagagauau ggucuuaaca cuaaucaccg caucguggug   240
uguucggaga acucauugca guuuuucaug ccgguccuug agcacuuuuu caucgggguc   300
gcagucgcgc cagcgaacga caucuacaau gagcgggaac ucuugaauag caugggaauc   360
ucccagccga cggucuguuu ugucuccaaa aagggggcugc agaaaauccu caacgugcag   420
aagaagcucc ccauuauuca aaagaucauc auuauggaua gcaagacaga uuaccaaggg   480
uuccagucga uguauaccuu ugugacaucg cauuugccgc cagggguuuaa cgaguaugac   540 uucgucccccg agucauuuga cagagauaaa accaucgcgc ugauuaugaa uuccucgggu   600
agcaccgguu ugccaaaggg ggugccguug ccccaccgca cugcuugugu gcgguucucg   660
cacgcuaggg auccuaucuu ugguaaucag aucauucccg acacagcaau ccuguccgug   720
guaccuuuuc aucacgguuu uggcauguuc acgacucucg cuauuugau uugcgguuuuc   780 agggucguac uuauguaucg guucgaggaa gaacuguuuu ugagauccuu gcaagauuac   840
aagauccagu cggcccuccu ugugccaacg cuuuucucau ucuuugcgaa ucgacacuuu   900
auugauaagu augaccuuuc caaucugcau gagauugccu cagggggagc gccgcuuagc   960
aaggaagucg gggaggcagu ggccaagcgc uuccaccuuc ccggaauucg cagggauac   1020 gggcucacga agacaacaauc cgcgauccuu aucacgcccg aggggugacga uaagccggga   1080 gccgucggaa aagugguccc cuucuuugaa gccaaggucg uagaccucga cacgggaaaa   1140

-continued

```
acccucggag ugaaccagag gggcgagcuc ugcgugagag ggccgaugau caugucaggu    1200
uacgugaaua acccugaagc gacgaaugcg cugaucgaca aggaugggug guugcauucg    1260
ggagacauug ccuauuggga ugaggaugag cacuucuuua ucguagaucg acuuaagagc    1320
uugaucaaau acaaaggcua ucagguagcg ccugccgagc ucgagucaau ccugcuccag    1380
caccccaaca uuuucgacgc cggaguggcc ggguugcccg augacgacgc gggugagcug    1440
ccagcggccg ugguaguccu cgaacauggg aaaacaauga ccgaaaagga gaucguggac    1500
uacguagcau cacaagugac gacugcgaag aaacugaggg gaggggguagu cuuuguggac    1560 gagguccccga aaggcuugac ugggaagcuu gacgcucgca aaauccggga aauccugauu    1620
aaggcaaaga aaggcgggaa aaucgcuguc                                   1650
```

<210> SEQ ID NO 5
<211> LENGTH: 119
<212> TYPE: RNA
<213> ORGANISM: Artificial Sequence
<220> FEATURE:
<223> OTHER INFORMATION: Firefly luciferase 3' UTR
<220> FEATURE:
<221> NAME/KEY: misc_feature
<222> LOCATION: (1)..(119)
<223> OTHER INFORMATION: A = AMP, C = CMP, G = GMP, U = N1-methyl-
      pseudoUMP

<400> SEQUENCE: 5

```
ugauaauagg cuggagccuc gguggccaug cuucuugccc cuugggccuc ccccagccc     60 cuccucccu uccugcaccc guaccccgu ggucuuugaa uaaagucuga gugggcggc    119
```

<210> SEQ ID NO 6
<211> LENGTH: 550
<212> TYPE: PRT
<213> ORGANISM: Artificial Sequence
<220> FEATURE:
<223> OTHER INFORMATION: Firefly luciferase

<400> SEQUENCE: 6

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
```

```
                    165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
            210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
        290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545                 550

<210> SEQ ID NO 7
<211> LENGTH: 3274
<212> TYPE: RNA
<213> ORGANISM: Artificial Sequence
```

```
<220> FEATURE:
<223> OTHER INFORMATION: LacZ nucleotide sequence (5' UTR, ORF, 3' UTR)
<220> FEATURE:
<221> NAME/KEY: misc_feature
<222> LOCATION: (1)..(3274)
<223> OTHER INFORMATION: A = AMP, C = CMP, G = GMP, U = N1-methyl-
      pseudoUMP

<400> SEQUENCE: 7
ucaagcuuuu ggacccucgu acagaagcua auacgacuca cuauagggaa auaagagaga      60
aaagaagagu aagaagaaau auaagagcca ccauggccuu ggcugucguc cugcaaagaa     120
gagauuggga aauccuggaa guuacgcaac ugaauagacu cgccgcacau ccaccguucg     180
cguccuggcg aaauagcgaa gaagcgcgga ccgacagacc uucgcagcag cugcgcucuc     240
ucaacgggga auggcgguuc gcauggumuc cggcuccuga ggcagucccg gaaagcuggc     300
ucgagugcga ccucccggaa gccgauacgg uggugguggc gucaaauugg caaaugcaug     360
gauacgacgc ccccaucuac accaacguca cuuacccuau caccgugaau cccccauucg     420
ucccgacuga aacccgacuu ggaugcuaca gccugaccuu uaacguggac gagucguggc     480
ugcaagaagg gcagacucgc aucauuuucg acggagucaa cuccgcguuc caucuuuggu     540
guaacggacg gugggggga uacggccagg acuccaggcu gccgagcgaa uucgacuugu     600
cagccuuccu gcgcgccggc gaaaaccgcc uggcugucau gguccuuaga uggucggaug     660
gcucguaccu ggaggaucag gacaugugga ggaugucagg gaucuccggg gaugucccgc     720
ugcuccacaa gccaacuacc cagaucuccg acuuucaugu ggccacccgc uucaacgaug     780
acuucagcag ggcgguucug gaagccgagg ugcaaaugug cggagaacug agggacuacc     840
uccgcgugac ugucucgcuc uggcagggug aaacccaagu ggcuucaggc acugaccgu     900 ucggaggaga aaucaucgac gaacggggag gauacgccga ucgcgucacc cugcgccuca     960 augugggaaaa uccgaaacug uggucggcag aaaucccuaa uuuguaccgg gccguggugg    1020
agcugcacac cgccgacgga acucugaucg aggccgaggc augcgaugug ggauccgcg     1080 aggaccgcau cgaaaauggga cugcuucugc uuaauggcaa accgcugcuc auccgcggag    1140
ugaacagaca cgagcaucac ccgcugcacg gucaggucau ggaugaacag acuaugguc    1200 aagacauccu gcugaugaaa caaaacaacu ucaacgccgu ucggugcucc cauuacccua    1260
aucccccguu ugguauacc cuuugcgauc ggauacgccu cuacguggug gacgaagcga     1320
acaucgagac ucacggaaug gucccuauga accgccucac ugacgacccg agguggcucc    1380 cggcaaugc ggaacgagug acucggauugg ugcagaggga ccgcaaccau ccgucgguga    1440
uaaucugguc gcuggggaac gaaucuggcc acggagcuaa ccacgaugcg cuguaccgcu    1500
ggauuaaguc gggacccca agccggcccg uccaguacga aggagguggu gcugauacca    1560
cugcaaccga caucaucugc ccaaugauaug cgcgggguga ugaggaccaa ccuuuccgg     1620 cggugccaaa gugguccauc aagaaauggc ucucgcugcc cggagaaacg cgccgcuga    1680 uccgugugcga auaugcgcac gcuaugggaa auucacuggg gggauuugcg aaguacuggc    1740
aggcuuuucg acaguacccg agacuccagg guggcuucgu ugggacugg guugaccaga    1800 gccucaucaa auacgaugaa aacggcaacc cauggccgc uacggcggaa gacuuuggag    1860
acaccccuaa cgaucgccag uucugcauga acggccuggu uucgccgac agaacuccgc    1920 auccagcccu uacugaggcu aagcaccaac aacaguucuu ccaguucaga cugucggggc    1980
aaacgaucga agugacuucc gaauaccucu uccggcauuc ggcaacgag uugcugcacu    2040 ggaguggucgc ccuggauga aagccccucg ccuccggaga agugccgcuc gacguggcgc    2100
```

```
cgcagggaaa gcaguugauc gaguugccgg aacugccaca gcccgaguca gcaggacagc  2160
ucuggcuuac cgucagaguc gugcagccaa augccaccgc cuggucggag gcaggacaua  2220
uuucagccug gcagcagugg cgccucgccg agaaucugag cgugaccuug ccagcagccu  2280
cacacgccau uccgcaucug accacguccg aaauggacuu uuguaucgaa cuggggaaua  2340
agcgcuggca guucaaucgg caaucaggcu uccuguccca gaugugauu ggugacaaga  2400 agcagcuccu gaccccgcug cgcgaucagu ucacucgcgc ccacuugac aacgacauug  2460 gcgugagcga ggccacgcgu aucgauccaa acgcuugggu ggagcgcugg aaggcggcug  2520
gccacuauca ggcggaggcc gcgcuccugc aguguaccgc ggauacccuc gcagacgccg  2580
uucugauuac cacggcgcau gccuggcaac accagggaaa gacccuguuu aucagccgca  2640
aaacuuaccg gaucgauggc agcggccaaa uggcgaucac ugggacguc gagguggcau  2700 cagacacucc acacccagca cggaucggac ucaauugcca acuggcucaa guggcugaga  2760
gagucaauug gcugggccuc ggcccccaag agaacuaccc ugaucggcuu acugccgcau  2820
gcuuugaccg gugggaucug ccucugucgg auauguacac ccccuacgug uucccauccg  2880
agaacggucu gagaugcggu acuagggagu gaacuacgg accgcaccaa uggagggggg  2940
acuuucaguu caacaucuca agauacagcc agcagcaauu gauggaaacc ucgcaccggc  3000
aucucuugca ugcagaggaa gggaccuggc ugaacaucga uggauuccac augggaauug  3060
gugggaguga cuccuggucc ccuagcgugu ccgcggaacu cagcugucc gccggccggu  3120 accacuacca gcucgugugg ugucaaaagu gauaauaggc uggagccucg guggccaugc  3180
uucuugcccc uugggccucc ccccagcccc uccuccccuu ccugcacccg uaccccgug  3240 gucuuugaau aaagucugag ugggcggcuc uaga                              3274
```

<210> SEQ ID NO 8
<211> LENGTH: 1019
<212> TYPE: PRT
<213> ORGANISM: Artificial Sequence
<220> FEATURE:
<223> OTHER INFORMATION: LacZ

<400> SEQUENCE: 8

```
Met Ala Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
                85                  90                  95

Thr Asn Val Thr Tyr Pro Ile Thr Val Asn Pro Pro Phe Val Pro Thr
            100                 105                 110

Glu Asn Pro Thr Gly Cys Tyr Ser Leu Thr Phe Asn Val Asp Glu Ser
        115                 120                 125

Trp Leu Gln Glu Gly Gln Thr Arg Ile Ile Phe Asp Gly Val Asn Ser
    130                 135                 140

Ala Phe His Leu Trp Cys Asn Gly Arg Trp Val Gly Tyr Gly Gln Asp
```

```
        145                 150                 155                 160
Ser Arg Leu Pro Ser Glu Phe Asp Leu Ser Ala Phe Leu Arg Ala Gly
                165                 170                 175

Glu Asn Arg Leu Ala Val Met Val Leu Arg Trp Ser Asp Gly Ser Tyr
            180                 185                 190

Leu Glu Asp Gln Asp Met Trp Arg Met Ser Gly Ile Phe Arg Asp Val
        195                 200                 205

Ser Leu Leu His Lys Pro Thr Thr Gln Ile Ser Asp Phe His Val Ala
    210                 215                 220

Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
                260                 265                 270

Glu Ile Ile Asp Glu Arg Gly Gly Tyr Ala Asp Arg Val Thr Leu Arg
            275                 280                 285

Leu Asn Val Glu Asn Pro Lys Leu Trp Ser Ala Glu Ile Pro Asn Leu
        290                 295                 300

Tyr Arg Ala Val Val Glu Leu His Thr Ala Asp Gly Thr Leu Ile Glu
305                 310                 315                 320

Ala Glu Ala Cys Asp Val Gly Phe Arg Glu Val Arg Ile Glu Asn Gly
                325                 330                 335

Leu Leu Leu Leu Asn Gly Lys Pro Leu Leu Ile Arg Gly Val Asn Arg
                340                 345                 350

His Glu His His Pro Leu His Gly Gln Val Met Asp Glu Gln Thr Met
            355                 360                 365

Val Gln Asp Ile Leu Leu Met Lys Gln Asn Asn Phe Asn Ala Val Arg
        370                 375                 380

Cys Ser His Tyr Pro Asn His Pro Leu Trp Tyr Thr Leu Cys Asp Arg
385                 390                 395                 400

Tyr Gly Leu Tyr Val Val Asp Glu Ala Asn Ile Glu Thr His Gly Met
                405                 410                 415

Val Pro Met Asn Arg Leu Thr Asp Asp Pro Arg Trp Leu Pro Ala Met
                420                 425                 430

Ser Glu Arg Val Thr Arg Met Val Gln Arg Asp Arg Asn His Pro Ser
            435                 440                 445

Val Ile Ile Trp Ser Leu Gly Asn Glu Ser Gly His Gly Ala Asn His
        450                 455                 460

Asp Ala Leu Tyr Arg Trp Ile Lys Ser Val Asp Pro Ser Arg Pro Val
465                 470                 475                 480

Gln Tyr Glu Gly Gly Gly Ala Asp Thr Thr Ala Thr Asp Ile Ile Cys
                485                 490                 495

Pro Met Tyr Ala Arg Val Asp Glu Asp Gln Pro Phe Pro Ala Val Pro
                500                 505                 510

Lys Trp Ser Ile Lys Lys Trp Leu Ser Leu Pro Gly Glu Thr Arg Pro
            515                 520                 525

Leu Ile Leu Cys Glu Tyr Ala His Ala Met Gly Asn Ser Leu Gly Gly
        530                 535                 540

Phe Ala Lys Tyr Trp Gln Ala Phe Arg Gln Tyr Pro Arg Leu Gln Gly
545                 550                 555                 560

Gly Phe Val Trp Asp Trp Val Asp Gln Ser Leu Ile Lys Tyr Asp Glu
                565                 570                 575
```

-continued

```
Asn Gly Asn Pro Trp Ser Ala Tyr Gly Gly Asp Phe Gly Asp Thr Pro
            580                 585                 590

Asn Asp Arg Gln Phe Cys Met Asn Gly Leu Val Phe Ala Asp Arg Thr
        595                 600                 605

Pro His Pro Ala Leu Thr Glu Ala Lys His Gln Gln Gln Phe Phe Gln
    610                 615                 620

Phe Arg Leu Ser Gly Gln Thr Ile Glu Val Thr Ser Glu Tyr Leu Phe
625                 630                 635                 640

Arg His Ser Asp Asn Glu Leu Leu His Trp Met Val Ala Leu Asp Gly
                645                 650                 655

Lys Pro Leu Ala Ser Gly Glu Val Pro Leu Asp Val Ala Pro Gln Gly
                660                 665                 670

Lys Gln Leu Ile Glu Leu Pro Glu Leu Pro Gln Pro Glu Ser Ala Gly
            675                 680                 685

Gln Leu Trp Leu Thr Val Arg Val Gln Pro Asn Ala Thr Ala Trp
        690                 695                 700

Ser Glu Ala Gly His Ile Ser Ala Trp Gln Gln Trp Arg Leu Ala Glu
705                 710                 715                 720

Asn Leu Ser Val Thr Leu Pro Ala Ala Ser His Ala Ile Pro His Leu
                725                 730                 735

Thr Thr Ser Glu Met Asp Phe Cys Ile Glu Leu Gly Asn Lys Arg Trp
                740                 745                 750

Gln Phe Asn Arg Gln Ser Gly Phe Leu Ser Gln Met Trp Ile Gly Asp
            755                 760                 765

Lys Lys Gln Leu Leu Thr Pro Leu Arg Asp Gln Phe Thr Arg Ala Pro
770                 775                 780

Leu Asp Asn Asp Ile Gly Val Ser Glu Ala Thr Arg Ile Asp Pro Asn
785                 790                 795                 800

Ala Trp Val Glu Arg Trp Lys Ala Ala Gly His Tyr Gln Ala Glu Ala
                805                 810                 815

Ala Leu Leu Gln Cys Thr Ala Asp Thr Leu Ala Asp Ala Val Leu Ile
                820                 825                 830

Thr Thr Ala His Ala Trp Gln His Gln Gly Lys Thr Leu Phe Ile Ser
            835                 840                 845

Arg Lys Thr Tyr Arg Ile Asp Gly Ser Gly Gln Met Ala Ile Thr Val
850                 855                 860

Asp Val Glu Val Ala Ser Asp Thr Pro His Pro Ala Arg Ile Gly Leu
865                 870                 875                 880

Asn Cys Gln Leu Ala Gln Val Ala Glu Arg Val Asn Trp Leu Gly Leu
                885                 890                 895

Gly Pro Gln Glu Asn Tyr Pro Asp Arg Leu Thr Ala Ala Cys Phe Asp
            900                 905                 910

Arg Trp Asp Leu Pro Leu Ser Asp Met Tyr Thr Pro Tyr Val Phe Pro
    915                 920                 925

Ser Glu Asn Gly Leu Arg Cys Gly Thr Arg Glu Leu Asn Tyr Gly Pro
    930                 935                 940

His Gln Trp Arg Gly Asp Phe Gln Phe Asn Ile Ser Arg Tyr Ser Gln
945                 950                 955                 960

Gln Gln Leu Met Glu Thr Ser His Arg His Leu Leu His Ala Glu Glu
                965                 970                 975

Gly Thr Trp Leu Asn Ile Asp Gly Phe His Met Gly Ile Gly Gly Asp
            980                 985                 990
```

```
Asp Ser Trp Ser Pro Ser Val Ser  Ala Glu Leu Gln Leu  Ser Ala Gly
        995                 1000                 1005

Arg Tyr  His Tyr Gln Leu Val  Trp Cys Gln Lys
   1010                  1015
```

<210> SEQ ID NO 9
<211> LENGTH: 3057
<212> TYPE: RNA
<213> ORGANISM: Artificial Sequence
<220> FEATURE:
<223> OTHER INFORMATION: LacZ ORF nucleotide sequence
<220> FEATURE:
<221> NAME/KEY: misc_feature
<222> LOCATION: (1)..(3057)
<223> OTHER INFORMATION: A = AMP, C = CMP, G = GMP, U = N1-methyl-pseudoUMP

<400> SEQUENCE: 9

```
auggccuugg cugucguccu gcaaagaaga gauugggaaa auccuggagu uacgcaacug      60
aauagacucg ccgcacaucc accguucgcg uccuggcgaa auagcgaaga agcgcggacc     120
gacagaccuu cgcagcagcu gcgcucucuc aacggggaau ggcgguucgc auggauuccg     180
gcuccugagg caguccccga aagcuggcuc gagugcgacc ucccggaagc cgauacggug     240
guggugccgu caaauuggca aaugcaugga uacgacgccc ccaucuacac caacgucacu     300
uacccuauca ccgugaauccc cccauucguc ccgacugaga acccgacugg augcuacagc     360
cugaccuuua cguggacga ucguggcug caagaagggc agacucgcau cauuucgac     420 ggagucaacu ccgcguucca ucuuuggugu aacggacggu gggugggaua cgggcaggac     480
uccaggcugc cgagcgaauu cgacuuguca gccuuccugc gcgccggcga aaccgccug     540 gcugucaugg uccuuagaug gucggauggc ucguaccugg aggaucagga caguggagg     600 augucaggga ucuuccggga uguucugcug cuccacaagc caacucccca gaucuccgac     660
uuucauguug ccaccccgcuu caacgaugac uucaggaggg cgguucugga gccgaggug     720 caaaugugcg agaacugag ggacuaccuc cgcgugacug ucgcucug gcaggggugaa     780 acccaaaggg cuucaggcac ucaccgucu ggaggagaaa ucaucgacga acggggagga     840 uacgcgauc gcgucacccu gcgccucaau uggaaaaauc cgaaacugug ucggcagaa     900 auccuaauu uguaccgggc cguggugag cugcacacgg ccgacggaac ucucgaugag     960
gccgaggcau gcgauguggg auuccgcgag guccgcaucg aaaauggacu gcuucugcuu    1020
aauggcaaac cgcugcucau ccgcggagug aacagacgag agacucacccc gcugcacggu    1080 caggucaugg augaacagac uauggugcaa gacauccugc ugaugaaaaa caacaacuuc    1140 aacgcguuc ggugcucccca uuacccuaau caccguugu gguauacccu uugcgaucgg    1200 uacgccucu acgguguga cgaagcgaac aucgagacuc acggaauggu cccuaugaac    1260
cgccucacug acgacccgag guggcucccg gcaaugucgg aacgagugac ucggaugug    1320 cagagggacc gcaaccaucc gucgugauuc auccggccgc uggggaacga aucuggccac    1380
ggagcuaacc acgaugcgcu guaccgcugg auuaagccg uggacccaag ccggcccguc    1440
caguacgaag gaggugguc ugauaccacu gcaaccgaca ucaucuggcc aauguauggcg    1500 cggguggaug aggaccaacc uuuccccgcg gugccaagu gguccaucaa gaauggcu    1560 uccgcugcgg agaaacgcg cccgcugauc cugugcgaau augcgacggc uauggggaau    1620
ucacuugggg gauuugcaaa guacuggcag gcuuucgac aguacccgag acuccagggu    1680
ggcuucgugu gggacugggu ugaccagagc cucaucaaau acgaugaaaa cggcaaccca    1740
```

```
uggccgcgu  acggcggaga  cuuuggagac  accccuaacg  aucgccaguu  cugcaugaac    1800
ggccuggugu  ucgccgacag  aacuccgcau  ccagcccuua  cugaggcuaa  gcaccaacaa    1860
caguucuucc  aguucagacu  gucggggcaa  acgaucgaag  ugacuuccga  auaccucuuc    1920
cggcauucgg  acaacgaguu  gcugcacugg  auggucgccc  uggauggaaa  gccccucgcc    1980
uccggagaag  ugccgcucga  cguggcgccg  cagggaaagc  aguugaucga  guugccggaa    2040
cugccacagc  ccgagucagc  aggacagcuc  uggcuuaccg  ucagagucgu  gcagccaaau    2100
gccaccgccu  ggucggaggc  aggacauauu  ucagccuggc  agcaguggcg  ccucgccgag    2160
aaucugagcg  ugaccuugcc  agcagccuca  cacgccauuc  cgcaucugac  cacguccgaa    2220
auggacuuuu  guaucgaacu  ggggaauaag  cgcuggcagu  ucaaucggca  aucaggcuuc    2280 cuguccccaga ugugggauugg ugacaagaag cagcuccuga ccccgcugcg cgaucaguuc    2340
acucgcgccc  cacuugacaa  cgacauuggc  gugagcgagg  ccacgcguau  cgauccaaac    2400
gcuugggugg  agcgcuggaa  ggcggcuggc  cacuaucagg  cggaggccgc  gcuccugcag    2460
uguaccgcgg  auacccucgc  agacgccguu  cugauuacca  cggcgcaugc  cuggcaacac    2520
cagggaaaga  cccuguuuau  cagccgcaaa  acuuaccgga  ucgauggcag  cggccaaaug    2580
gcgaucacug  uggacgucga  gguggcauca  gacacuccac  acccagcacg  gaucggacuc    2640
aauugccaac  uggcucaagu  ggcugagaga  gucaauuggc  ugggccucgg  cccccaagag    2700
aacuacccug  aucggcuuac  ugccgcaugc  uuugaccggu  gggaucugcc  ucugucggau    2760
auguacaccc  ccuacguguu  cccauccgag  aacggucuga  gaugcgguac  uagggaguug    2820
aacuacggac  cgcaccaaug  gaggggggac  uuucaguuca  acaucucaag  auacagccag    2880
cagcaauuga  uggaaaccuc  gcaccggcau  cucuugcaug  cagaggaagg  gaccuggcug    2940
aacaucgaug  gauccacau  gggaauuggu  gggaugacu  ccugguccccc  uagcgugucc    3000 gcggaacuuc  agcuguccgc  cggccgguac  cacuaccagc  ucguguggug  ucaaaag      3057
```

What is claimed is:

1. A composition comprising a modified mRNA encoding a VEGF-A polypeptide of SEQ ID NO: 2 and a citrate saline buffer, wherein the citrate saline buffer is substantially free of divalent cations.

2. The composition of claim 1, wherein the composition does not include a lipid-based complex.

3. The composition of claim 1, wherein the composition does not include a lipid-based complex nor calcium.

4. A formulation comprising a pharmaceutically acceptable amount of a modified mRNA encoding a VEGF-A polypeptide of SEQ ID NO: 2 and a citrate saline buffer, wherein the citrate saline buffer is substantially free of divalent cations.

5. The formulation of claim 4, wherein the citrate saline buffer is substantially free of calcium and magnesium.

6. The formulation of claim 4, wherein the citrate saline buffer contains no calcium or magnesium.

7. The formulation of claim 4, further comprising a pharmaceutically acceptable excipient.

8. The formulation of claim 7, wherein the pharmaceutically acceptable excipient is a solvent, dispersion medium, diluent, dispersion, suspension aid, surface active agent, isotonic agent, thickening or emulsifying agent, preservative, core-shell nanoparticle, polymer, peptide, protein, cell, hyaluronidase, or mixture thereof.

9. The formulation of claim 4, wherein the formulation does not include a lipid-based complex.

10. The formulation of claim 4, wherein the formulation does not include a lipid-based complex nor calcium.

11. A method of treating a human subject suffering from a disease responsive to VEGF-A therapy, comprising administering to the human subject the composition according to claim 1.

12. The method of claim 11, wherein the citrate saline buffer is substantially free of calcium and magnesium.

13. The method of claim 11, wherein the citrate saline buffer contains no calcium or magnesium.

14. The method of claim 11, wherein the composition further comprises a pharmaceutically acceptable excipient.

15. The method of claim 14, wherein the pharmaceutically acceptable excipient is a solvent, dispersion medium, diluent, dispersion, suspension aid, surface active agent, isotonic agent, thickening or emulsifying agent, preservative, core-shell nanoparticle, polymer, peptide, protein, cell, hyaluronidase, or mixture thereof.

16. The method of claim 11, wherein the disease is heart failure with reduced or preserved ejection fraction, kidney disease, a disease involving skin grafting and tissue grafting, post-MI cardiac dysfunction, ischemic heart disease, a vascular injury from trauma or surgery, a skin ulcer including a diabetic ulcer, critical limb ischemia, pulmonary hypertension, or peripheral arterial disease.

17. The method of claim 11, wherein the composition is administered to the human subject via an intramuscular route, via an intradermal route, via a subcutaneous route, via an intracardial route, via an epicardial route, through a portal vein catheter, through a coronary sinus catheter, or by direct administration into the area to be treated.

18. The method of claim 11, wherein the composition is administered to the human subject at a fixed-dosage in multiple administrations.

19. The method of claim 11, wherein the composition is administered to the human subject via an intracardial route, via an epicardial route, through a portal vein catheter, or through a coronary sinus catheter, and at a fixed-dosage in multiple administrations.

20. The method of claim 11, wherein the composition is administered to the human subject by direct administration into the area to be treated at a fixed-dosage in multiple administrations.

21. The method of claim 11, wherein the composition comprises a concentration of the modified mRNA of between 0.1 and 1 µg/µL formulated in the citrate saline buffer.

22. The method of claim 11, wherein the composition comprises a concentration of the modified mRNA of between 1 and 10 µg/µL formulated in the citrate saline buffer.

23. The method of claim 11, wherein the composition comprises a concentration of the modified mRNA of between 10 and 50 µg/µL formulated in the citrate saline buffer.

24. The method of claim 11, wherein the composition comprising the citrate saline buffer is less toxic to the human subject than a lipid-based composition or formulation.

25. The method of claim 11, wherein the composition does not include a lipid-based complex.

26. The method of claim 11, wherein the composition does not include a lipid-based complex nor calcium.

* * * * *